(12) United States Patent
Tsantrizos

(10) Patent No.: US 8,076,365 B2
(45) Date of Patent: Dec. 13, 2011

(54) VIRAL POLYMERASE INHIBITORS

(75) Inventor: Youla S. Tsantrizos, Montreal (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 630 days.

(21) Appl. No.: 12/063,468

(22) PCT Filed: Aug. 3, 2006

(86) PCT No.: PCT/CA2006/001292
§ 371 (c)(1),
(2), (4) Date: Mar. 6, 2008

(87) PCT Pub. No.: WO2007/019674
PCT Pub. Date: Feb. 22, 2007

(65) Prior Publication Data
US 2010/0168098 A1    Jul. 1, 2010

Related U.S. Application Data

(60) Provisional application No. 60/707,769, filed on Aug. 12, 2005.

(51) Int. Cl.
*A61K 31/415* (2006.01)
*C07D 235/02* (2006.01)

(52) U.S. Cl. ...................................... 514/394; 548/302.1

(58) Field of Classification Search .................. 514/394; 548/302.1
See application file for complete search history.

(56) References Cited

U.S. PATENT DOCUMENTS

| | | |
|---|---|---|
| 3,565,912 A | 2/1971 | Szmuszkovicz |
| 4,003,908 A | 1/1977 | Denzel et al. |
| 4,146,725 A | 3/1979 | Meyer et al. |
| 4,250,317 A | 2/1981 | Meyer et al. |
| 4,252,803 A | 2/1981 | Webb |
| 4,264,325 A | 4/1981 | Meyer et al. |
| 4,360,679 A | 11/1982 | Meyer et al. |
| 4,384,121 A | 5/1983 | Meyer |
| 4,432,886 A | 2/1984 | Meyer |
| 4,433,975 A | 2/1984 | Meyer |
| 4,590,200 A | 5/1986 | Cross et al. |
| 4,740,519 A | 4/1988 | Shroot et al. |
| 4,859,684 A | 8/1989 | Raeymaekers et al. |
| 4,898,863 A | 2/1990 | Brown et al. |
| 4,920,140 A | 4/1990 | Shroot et al. |
| 5,059,621 A | 10/1991 | Shroot et al. |
| 5,216,003 A | 6/1993 | Vazquez |
| 5,410,061 A | 4/1995 | Gilmore et al. |
| 5,482,956 A | 1/1996 | Lunkenheimer et al. |
| 5,527,819 A | 6/1996 | Williams et al. |
| 5,661,159 A | 8/1997 | Matsuo et al. |
| 5,817,689 A | 10/1998 | Kato et al. |
| 5,866,594 A | 2/1999 | Endo et al. |
| 5,912,260 A | 6/1999 | Kalindjian et al. |
| 5,932,743 A | 8/1999 | Collini et al. |
| 6,063,806 A | 5/2000 | Kamiya et al. |
| 6,069,156 A | 5/2000 | Oku et al. |
| 6,169,107 B1 | 1/2001 | Kitano et al. |
| 6,184,238 B1 | 2/2001 | Takano et al. |
| 6,228,868 B1 | 5/2001 | Gwaltney, II et al. |
| 6,358,992 B1 | 3/2002 | Pamukcu et al. |
| 6,399,644 B1 | 6/2002 | Wexler et al. |
| 6,448,281 B1 | 9/2002 | Beaulieu et al. |
| 6,455,525 B1 | 9/2002 | Singh et al. |
| 6,479,508 B1 | 11/2002 | Beaulieu et al. |
| 6,579,882 B2 | 6/2003 | Stewart et al. |
| 6,770,643 B2 | 8/2004 | Cox et al. |
| 6,770,666 B2 | 8/2004 | Hashimoto et al. |
| 6,794,404 B2 | 9/2004 | Beaulieu et al. |
| 6,841,566 B2 | 1/2005 | Beaulieu et al. |
| 6,897,207 B2 | 5/2005 | Cox et al. |
| 7,098,231 B2 | 8/2006 | Poupart et al. |
| 7,112,600 B1 | 9/2006 | Hashimoto et al. |
| 7,141,574 B2 | 11/2006 | Beaulieu et al. |
| 7,157,486 B2 | 1/2007 | Beaulieu et al. |
| 7,241,801 B2 | 7/2007 | Beaulieu et al. |
| 7,323,470 B2 | 1/2008 | Poupart et al. |
| 7,332,614 B2 | 2/2008 | Khodabocus et al. |

(Continued)

FOREIGN PATENT DOCUMENTS

CA    1111695    11/1981

(Continued)

OTHER PUBLICATIONS

International Search Report, Form PCT/ISA/210, for corresponding PCT/CA2006/001292.
Hijkata, M., et al., "Gene mapping of the putative structural region of the hepatitis C virus genome by in vitro processing analysis". Proc. Natl. Acad. Sci. USA, vol. 88, Jul. 1991, Biochemistry, pp. 5547-5551.
Hijkata, M., et al., "Two distinct proteinase activities required for the processing of a putative nonstructural precursor protein of hepatitis C virus". Journal of Virology, Aug. 1993, Vo. 67, No. 8, pp. 4665-4675.
Hishmat, O. H., et al; "Synthesis of Pharmacologically Active Indoles"; Bolletino Chimico Farmaceutico (1999), 183 (6), pp. 259-266 (XP-002233311).

(Continued)

Primary Examiner — Shengjun Wang
(74) Attorney, Agent, or Firm — Michael P. Morris; David A. Dow

(57) ABSTRACT

The present invention relates to compounds represented by formula (I) wherein A, B, D, E, $R^2$, $R^3$, $R^4$, $R^5$, $R^6$, $R^9$, a, b, d and e are as defined herein, their salt or ester and pharmaceutical compositions thereof useful in the treatment of hepatitis C viral (HCV) infection. Said compounds were found to have inhibitory activity against HCV polymerase, especially as inhibitors of HCV NS5B polymerase.

(I)

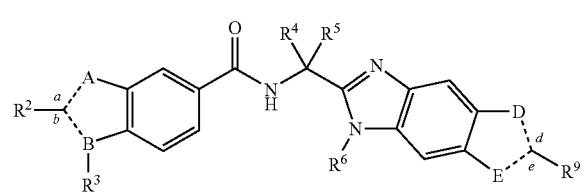

23 Claims, No Drawings

U.S. PATENT DOCUMENTS

| | | |
|---|---|---|
| 2001/0039286 A1 | 11/2001 | Dinnell et al. |
| 2002/0173527 A1 | 11/2002 | Astles |
| 2003/0050320 A1 | 3/2003 | Hashimoto et al. |
| 2003/0108862 A1 | 6/2003 | Kukolj et al. |
| 2003/0134853 A1 | 7/2003 | Priestley et al. |
| 2004/0082635 A1 | 4/2004 | Hashimoto et al. |
| 2004/0097438 A1 | 5/2004 | Hashimoto et al. |
| 2004/0110126 A1 | 6/2004 | Kukolj et al. |
| 2004/0171626 A1 | 9/2004 | Beaulieu et al. |
| 2004/0171833 A1 | 9/2004 | Buchwald et al. |
| 2004/0224955 A1 | 11/2004 | Beaulieu et al. |
| 2005/0032875 A1 | 2/2005 | Wolleb et al. |
| 2005/0209465 A1 | 9/2005 | Li et al. |
| 2005/0222236 A1 | 10/2005 | Tsantrizos et al. |
| 2006/0160798 A1 | 7/2006 | Beaulieu et al. |
| 2006/0183752 A1 | 8/2006 | Khodabocus et al. |
| 2006/0293306 A1 | 12/2006 | Beaulieu et al. |
| 2007/0142380 A1 | 6/2007 | Beaulieu et al. |
| 2007/0249629 A1 | 10/2007 | Beaulieu et al. |
| 2008/0119490 A1 | 5/2008 | Poupart et al. |
| 2009/0087409 A1 | 4/2009 | Beaulieu et al. |
| 2009/0170859 A1 | 7/2009 | Tsantrizos et al. |

FOREIGN PATENT DOCUMENTS

| | | |
|---|---|---|
| CA | 2150812 | 6/1994 |
| CA | 2158996 | 10/1994 |
| CA | 2143040 | 8/1995 |
| CA | 2124169 | 11/1995 |
| CA | 2164394 | 6/1996 |
| CA | 2223585 | 12/1996 |
| CA | 2241186 | 6/1997 |
| CA | 2389165 | 5/2001 |
| CA | 2363274 | 7/2001 |
| CA | 2412718 | 1/2002 |
| CA | 2448737 | 1/2003 |
| CA | 2449180 | 2/2003 |
| CH | 511873 | 8/1971 |
| DE | 2641060 | 3/1978 |
| DE | 3522230 | 1/1987 |
| DE | 19507913 | 9/1996 |
| EP | 10063 | 4/1980 |
| EP | 0011824 | 6/1980 |
| EP | 12291 | 6/1980 |
| EP | 14411 | 8/1980 |
| EP | 50957 | 5/1982 |
| EP | 73663 | 3/1983 |
| EP | 209707 | 1/1987 |
| EP | 242167 | 10/1987 |
| EP | 318084 | 5/1989 |
| EP | 353606 | 2/1990 |
| EP | 429240 | 5/1991 |
| EP | 439356 | 7/1991 |
| EP | 459334 | 12/1991 |
| EP | 539117 | 4/1993 |
| EP | 546713 | 6/1993 |
| EP | 549175 | 6/1993 |
| EP | 563910 | 10/1993 |
| EP | 583665 | 2/1994 |
| EP | 607439 | 7/1994 |
| EP | 615159 | 9/1994 |
| EP | 750226 | 12/1996 |
| EP | 0801059 | 10/1997 |
| EP | 987250 | 3/2000 |
| EP | 1142880 | 10/2001 |
| EP | 1162196 | 12/2001 |
| EP | 1256628 A2 | 11/2002 |
| FR | 1604809 | 4/1972 |
| FR | 2291749 | 6/1976 |
| GB | 1094903 | 12/1967 |
| GB | 1186504 | 4/1970 |
| GB | 1436089 | 5/1976 |
| GB | 1509527 | 5/1978 |
| GB | 2118552 | 11/1983 |
| GB | 2164648 | 3/1986 |
| GB | 2197320 | 5/1988 |
| GB | 2203420 | 10/1988 |
| JP | 6297858 | 10/1984 |
| JP | 60149502 | 8/1985 |
| JP | 61085360 | 4/1986 |
| JP | 3156444 | 7/1991 |
| JP | 5239036 | 9/1993 |
| JP | 6161064 | 6/1994 |
| JP | 6186703 | 7/1994 |
| JP | 6186705 | 7/1994 |
| JP | 6186706 | 7/1994 |
| JP | 6194794 | 7/1994 |
| JP | 6239841 | 8/1994 |
| JP | 7140604 | 6/1995 |
| JP | 7228530 | 8/1995 |
| JP | 9124632 | 5/1997 |
| JP | 09124632 A | 5/1997 |
| JP | 9328678 | 12/1997 |
| JP | 10067682 | 3/1998 |
| JP | 10114654 | 5/1998 |
| JP | 10204059 | 8/1998 |
| JP | 10265478 | 10/1998 |
| JP | 11021693 | 1/1999 |
| JP | 115003445 | 3/1999 |
| JP | 11177218 | 7/1999 |
| JP | 2001122855 | 5/2001 |
| WO | 9116313 | 10/1991 |
| WO | 9210097 | 6/1992 |
| WO | 9306828 | 4/1993 |
| WO | 9411349 | 5/1994 |
| WO | 9507263 | 3/1995 |
| WO | 9616938 | 6/1996 |
| WO | 9632379 | 10/1996 |
| WO | 9639391 | 12/1996 |
| WO | 9712613 | 4/1997 |
| WO | 9744319 | 11/1997 |
| WO | 9748697 | 12/1997 |
| WO | 9801436 | 1/1998 |
| WO | 9808847 | 3/1998 |
| WO | 9829408 | 7/1998 |
| WO | 9837069 | 8/1998 |
| WO | 9837079 | 8/1998 |
| WO | 9928297 | 6/1999 |
| WO | 9929660 | 6/1999 |
| WO | 9929661 | 6/1999 |
| WO | 9929843 A1 | 6/1999 |
| WO | 9951781 | 10/1999 |
| WO | 9961020 | 12/1999 |
| WO | 9965886 | 12/1999 |
| WO | 0006529 | 2/2000 |
| WO | 0006556 | 2/2000 |
| WO | 0006566 | 2/2000 |
| WO | 0010573 | 3/2000 |
| WO | 0013708 | 3/2000 |
| WO | 0018231 | 4/2000 |
| WO | 0026202 | 5/2000 |
| WO | 0027846 | 5/2000 |
| WO | 0130774 | 5/2001 |
| WO | 0132653 | 5/2001 |
| WO | 0147883 | 7/2001 |
| WO | 0147922 | 7/2001 |
| WO | 0151487 | 7/2001 |
| WO | 0185172 | 11/2001 |
| WO | 0187885 | 11/2001 |
| WO | 0190121 | 11/2001 |
| WO | 0204425 | 1/2002 |
| WO | 0206246 | 1/2002 |
| WO | 02057287 | 7/2002 |
| WO | 02057425 | 7/2002 |
| WO | 02059118 | 8/2002 |
| WO | 02069903 | 9/2002 |
| WO | 02070739 | 9/2002 |
| WO | 02098424 | 12/2002 |
| WO | 02100846 | 12/2002 |
| WO | 02100851 | 12/2002 |
| WO | 03/007945 | 1/2003 |
| WO | 03000254 | 1/2003 |
| WO | 03/010140 | 2/2003 |
| WO | 03/010141 | 2/2003 |
| WO | 03014377 | 2/2003 |
| WO | 03/018555 | 3/2003 |
| WO | 03026587 | 4/2003 |

| WO | 03040112 | 5/2003 |
| WO | 03101993 | 12/2003 |
| WO | 2004005286 | 1/2004 |
| WO | 2004/064925 | 8/2004 |
| WO | 2004065367 A1 | 8/2004 |
| WO | 2004087714 | 10/2004 |
| WO | 2005/012288 | 2/2005 |
| WO | 2005014543 | 2/2005 |
| WO | 2005/080388 | 9/2005 |

OTHER PUBLICATIONS

Hoofnagle, J.H.; 1997; Hepatology 26: 15S-20S.

Hulme, C., et al; "The Synthesis and Biological Evaluation of a Novel Series of Indole PDE4 Inhibitors I"; Bioorganic & Medicinal Chemistry Letters 8 (1998), pp. 1867-1872 (XP-002233861).

Ishiyama, T., Murata, M., Miyaura, N.; "Palladium(0)-Catalyzed Cross-Coupling Reaction of Alkoxydiboron with Haloarenes: A Direct Procedure for Arylboronic Esters;" J. Org. Chem. 1995, 60, 7508.

Kim, D. W., et al., "C-terminal domain of the hepatitis C virus NS3 protein contains an RNA helicase activity". Biochemical & Biophysical Research Communications, vol. 215, No. 1, 1995, pp. 160-166.

Kim, J.E., et al., "Subcellular localization of hepatitis C viral proteins in mammalian cells". Arch Virol., 1999, 144, pp. 329-343.

Kolykhalov, A.A. et al,"Hepatitis C Virus-Encoded Enzymatic Activities and Conserved RNA Elements in the 3' nontranslated Region are Essential for Virus Replication in Vivo", J. Virology, 2000, 74(4): 2046-2051.

Kwong, A. D., et al., "Hepatitis C virus NS3/4A protease". Antiviral Research, 40, 1998, pp. 1-18.

Lauer, G. and Walker, B., "Hepatitis C Virus Infection," N. Engl. J. Med., vol. 345(1), pp. 41-52 (Jul. 2001), at p. 46, col. 1, lines 23-25.

Lemon, S.H.; Honda, M.; "Internal Ribosome Entry Sites within the RNA Genomes of Hepatitis C Virus and Other Flaviviruses;" 1997; Semin. Virol. 8: 274-288.

Lesburg, C.A., et al., "Crystal structure of the RNA-dependent RNA polymerase from hepatitis C virus reveals a fully encircled active site". Nature Sructural Biology, vol. 6, No. 10, 1999, p. 937-943.

Levin, Jules, "Safety, Pharmacokinetics and Antiviral effects of Boehringer Ingelheim BILB 1941, a Novel HCV RNA Polymerase, After 5 days Oral treatment in Patients with Chronic Hepatitis C", www.natap.org/2007/EASL/EASL_48.htm EASL 42nd Mtg. of Euruopean Association for the Study of Liver Diseases, Barcelona, Spain Apr. 11-15, 2007.

Lindsay, K.L.; "Therapy of Hepatitis C: Overview;" 1997; Hepatology 26: 71S-77S.

Lohmann, V. et al, "Replication of Subgenomic Hepatitis C Virus RNAs in a Hepatoma Cell Line" Science, 1999, 285: 110-113.

Lohmann, V., et al., "Biochemical and kinetic analyses of NS5B RNA-dependent RNA polymerase of the hepatitis C virus". Virology, Article No. VY989311, Vo. 249, 1998, pp. 108-118.

Lohmann, V., et al., "Biochemical Properties of hepatitis C virus NS5B RNA-dependent RNA polymerase and identification of amino acid sequence motifs essential for enzymatic activity". Journal of Virology, Nov. 1997, Vo. 71, No. 11, pp. 8416-8428.

Love, R. A., et al., "The crystal structure of hepatitis C virus NS3 proteinase reveals a trypsin-like fold and a structural zinc binding site". Cell, vol. 87, 1996, pp. 331-342.

Luo, G., et al., "DeNovo initiation of RNA synthesis by the RNA-dependent RNA polymerase (NS5B) of hepatitis C virus". Journal of Virology, Jan. 2000, vol. 74, No. 2, pp. 851-863.

Mayer et al, "Solid-Phase Synthesis of Benzimidazoles"; Tetrahedron Letters 39 (1998) 6655-6658.

McKercher, G., et al., "Specific inhibitors of HCV polymerase identified using an NS5B with lower affinity for template/primer substrate". Nucleic Acids Research, 2004, vol. 32, No. 2, pp. 422-431.

Merlic, C.A. et al. "Benzannulation reactions of Fischer carbene compleses for the synthesis of indolocarbozoles" Tetrahedron, vol. 57, No. 24, p. 5199-5212, 2001.

Miller, J.A. et al, "Preparation of Unsymmetrical Biaryls via Ni-or Pd-Catalyzed Coupling of Aryl chlorides with Arylzincs". Tetrahdron Letters, vol. 39 (36), 1998, pp. 6441-6444.

Minato, Akio et al, "Palladium-Phosphine Complex Catalyzed Cross-Coupling Reaction of 1-Methyl-2-pyrrolyl-magnesium Bromide and-zinc chloride with organic halides" Tetrahedron Letters, vol. 22, No. 52, 1981 p. 5319.

Miyaura, N. et al. "Palladium Catalyzed Cross-Coupling Reactions of Organoboron Compounds", Chem. Rev. 1995, vol. 95, pp. 2457-2483.

Murata, M.; Oyama, T.; Watanabe, S., Masuda, Y. "Palladium-Catalyzed Borylation of Aryl Halides or Triflates with Dialkoxyborne: A Novel and Facile Synthetic Route to Arylboronates;" J. Org. Chem. 2000, 65, 164.

Negishi, S. Baba, "Novel Stereoselective Alkenyl-Aryl Coupling via Nickel-catalysed Reaction of Alkenylalanes with Aryl Halides;" J. Chem. Soc. Chem. Communications, 1976, 596-597.

Oh, J-W. et al., "A recombinant hepatitis C virus RNA-dependent RNA polymerase capable of copying the full-length viral RNA". Journal of Virology, Sep. 1999, Vo. 73, No. 9, pp. 7694-7702.

Perandones, F. et al; Synthesis of imidazol[4,5-b]pyridines from aminoimidazolecarbaldehydes, J. heterocyc. Chem. vol. 34, pp. 107-112, 1997.

Qin, W. et al., "Mutational analysis of the structure and function of hepatitis C virus RNA-dependent RNA polymerase". American Assoc. for the Study of Liver Diseases. Hepatology, vol. 33, No. 3, 2001, pp. 728,737.

Reed, K.E., et al., "Phosphorylation of the hepatitis C virus NS5A protein in vitro and in vivo: properties of the NS5A-associated kinase". Journal of Virology, Oct. 1997, vol. 71, No. 10, pp. 7187-7197.

Reed, K.E.; Rice, C.M.; "Overview of Hepatitis C Virus Genome Structure, Polyprotein Processing, and Protein Properties;" 1999; Curr. Top. Microbiol. Immunol. 242: pp. 55-84.

Reichard, O. et al, "Therapy of Hepatitis C: Alpha Interferon and Ribavirin;" 1997 Hepatology 26; pp. 108S-111S.

Rice, C.M.; 1996; "Flavivindae: the viruses and their replication"; pp. 931-960 in Fields Virology; Fields, B.N.; Knipe, D.M.; Howley, P.M. (eds.); Lippincott-Raven Publishers, Philadelphia, PA.

Rorrer, L.C. et al. "Convenient New Route to Tetradentate and Pentadentate Macrocyclic Tetraamide Ligands", Organic Letters, 1999, vol. 1, No. 8, pp. 1157-1159.

Roth, H. J., et al; "Synthesis of Indole and Carbazole Derivatives by Condensation of Alpha-hydroxyketones and Aromatic Amines"; Archiv der Pharmazie and Berichte der Deutschen Pharmazeutischen Gesellschaft (1972), 305(3), pp. 159-171 (XP-002233858).

Sakamoto, T., et al, "Indolylzinc Iodides by Oxidative addition of activ zinc to Iodoindoles" Tetrahedron Letters, vol. 34, No. 37, 1993, p. 5955.

Sarisky, R.T. "Non-nucleoside inhibitors of the HCV polymerase". Journal of Antimicrobial Chemotherapy, 2004, 54, pp. 14-16.

Sarrazin, C., et al., "SCH 503034, a Novel hepatitis C virus protease inhibitor, plus pegylated inteferon a-2b for genotype 1 nonresponders". Gastroenterolgy, 2007, 132, pp. 1270-1278.

Simons, J. N., et al., "Identification of two flavivirus-like genomes in the GB hepatitis agent". Proc. Natl, Acad. Sci, Medical Sciences, Vo. 92, Apr. 1995, pp. 3401-3405.

Stanforth, S.P. "Catalytic Cross-coupling Reactions in Biaryl Synthesis" Tetrahedron, vol. 54(3-4), 1998, pp. 263-303.

Sun, X-L., et al., "De Novo RNA synthesis catalyzed by HCV RNA-dependent RNA polymerase". Biochemical and Biophysical Research Communications, vol. 268, 2000, pp. 798-803.

Takehide, N. et al; "Benzo-Heterocyclic Derivative"; Patent Abstracts of Japan; Publication No. 09124632 A; May 13, 1997.

Tomei, L., et al., "Biochemical characterization of a hepatitis C virus RNA-dependent RNA polymerse mutant lacking the C-terminal hydrophobic sequence". Journal of General Virology, 2000, 81, pp. 759,767.

Watanabe, T. et al, "Synthesis of sterically hindered blaryis via the palladium-catalyzed cross-coupling reaction of aryliboronic acids of their esters with haloarenes" SYNLETT, vol. 3, p. 207-210, 1992.

Wu et al; "One-pot' nitro reduction-cyclisation solid phase route to benzimidazoles"; Tetrahedron Letters 41 (2000) 9871-9874.

Yamashita, T., et al., "RNA-dependent RNA polymerase activity of the soluble recombinant hepatitis C virus NS5B protein truncated at the C-terminal region". The Journal of Biological Chemistry, vol. 273, No. 25, Jun. 1999, pp. 15479-15486.

Yanagi, M., et al., "Transcripts from a single full-length cDNA clone of hepatitis C virus are infectious when directly transfected into the liver of a chimpanzee". PNAS, Vo. 94, Aug. 1997, pp. 8738-8743.

Youngdale, G. A. et al; "Synthesis and Antiinflammatory Activity of 5-Substituted 2,3-bis(p-methoxyphenyl) indoles"; J Med Chem (1969) 12, pp. 948-949 (XP-002233859).

Yuan, Z-H, et al., "Expression, purfication, and partial characterization of HCV RNA polymerase". Biochemical and Biophysical Research Communications, vol. 232, 1997, pp. 231-235.

Zhang, H-C., et al: "Efficient synthesis of 3-substituted 2-arylindoles via Suzuki coupling reactions in the solid phase"; Tetrahedron Letters, 42, 2001, pp. 4751-4754.

Zhang, J-H, et al., "A simple statistical parameter for use in evaluation and validation of high throughput screening assays". Journal of Biomolecular Screening, vol. 4, Nov. 1999, pp. 67-73.

Zhong, W., et al., "De Novo initiation of RNA synthesis by hepatitis C virus nonstructural protein 5B polymerase". Journal of Virology, Feb. 2000, Vo. 74, No. 4, pp. 2017-2022.

Zhong, W., et al., "Template/primer requirements and single nucleotide incorporation by hepatitis C virus nonstructural protein 5B polymerase". Journal of Virology, Oct. 2000, vol. 74, No. 19, pp. 9134-9143.

Afdhal, N, O'Brien C, Godofsky E, et al. Valpicitabine (NM283), alone or with PEG-interferon, compared to PEG interferon/ribavirin (PEGIFN/RBV) retreatment in patients with HCV-1 infection and prior non-response to PEBIFN/RBV: One-year results. Presented at the 42nd annual EASL meeting, Apr. 11-15, 2007, Barcelona, Spain.

Ago, H., et al., "Crystal structure of the RNA-dependent RNA polymerase of hepatitis C virus". Structure, 1999, V.7, No. 11, Research Article, pp. 1417-1426.

Amat, Mercedes, et al, "An Efficient Synthesis of 2-(2-Pyridyl)indoles by Palladium (0)-catalyzed heteroarylation", Tetrahedron Letters, vol. 34, No. 31, 1993, p. 5005.

Baba et al.; "A Novel Stereospecific Alkenyl'Alkenyl Cross-Coupling by a Palladium or Nickel-Catalyzed Reaction of Alkenylalanes with Alkenyl Halides" J. Am. Chem. Soc., 1976, 98, 6729-6731.

Bartenschlager, R.,et al., "Nonstructural protein 3 of the hepatitis C virus encodes a serine-type proteinase required for cleavage at the NS3/4 and NS4/5 junctions". Journal of Virology, Jul. 1993, p. 3835-3844.

Beaulieu et al. "Non-nucleoside inhibitors of the hepatitis C virus NS5B polymerase: discovery and preliminary SAR of benzimidazole derivatives." Bioorganic and Medicinal Chemistry Letters, 14 (2004) 119-124.

Beaulieu, P.L. et al; "Therapies for Hepatitis C Infection: Targeting the Non-Structural Proteins of HCV"; Curr. Med. Chem.-Anti-Infective Agents, 2002, vol. 1, No. 2, pp. 1-14.

Behrens, S-E., et al., "Identification and properties of the RNA-dependent RNA polymerase of hepatitis C virus". The EMBO Journal, vol. 15, No. 1, 1996, pp. 12-22.

Bressanelli, S., et al., "Crystal structure of the RNA-dependent RNA polymerase of hepatitis C virus". PNAS, Nov. 1999, Vo. 96, No. 23. pp. 13034-13039.

Bukh, J. et al., "Toward a surrogate model for hepatitis C virus: an infectious molecular clone of the GB virus-B hepatitis agent" Virology, vol. 262, 1999, pp. 470-478.

CA Abstract, CA 123: 33085, 1995.
CA Abstract, CA 126: 305540, 1997.

Carroll, S. S., et al., "Only a small fraction of purified hepatitis C RNA-dependent RNA polymerase is catalytically compentent: implications for viral replication and in vitro assays". Biochemistry, 2000, 39, pp. 8243-8249.

CAS Registry No. 115577-24-7 Registry Copyright 2001 ACS.
CAS Registry No. 214150-90-0 Registry Copyright 2001 ACS.
CAS Registry No. 214150-93-3 Registry Copyright 2001 ACS.
CAS Registry No. 66315-47-7 Registry Copyright 2001 ACS.
CAS Registry No. 66315-51-3 Registry Copyright 2001 ACS.
CAS Registry No. 66315-52-4 Registry Copyright 2001 ACS.
CAS Registry No. 66630-73-7 Registry Copyright 2001 ACS.
Chemical Abstract for DE 2642877: CA1977:453062.
Chemical Abstract for EP50957: CA1982:509865.
Chemical Abstract for EP73663: CA 1983:505247.
Chemical Abstract for WO 2000006556 A1: CA2000:98534.
Chemical Abstract for WO 2000026202 A1: CA2000:314687.
Chemical Abstract for WO 2000027846 A2: CA2000:335410.
Chemical Abstract for WO 2001/047883: CA2001:489367.
Chemical Abstract for WO 2001/087885: CA2001:851160.
Chemical Abstract for WO 9632379: CA 1996:746234.
Chemical Abstract for WO 9808847 A1: CA1998163594.
Chemical Abstract for WO 9829408 A1: CA1998:485053.
Chemical Abstract: CA 128:275074 for JP 10-067682, 1998.
Chemical Abstract: CA 129:45274 for JP 10 114654, 1998.
Chemical Abstract: CA 134:340435 for JP 2001 122855.
Chemical Abstract: CA 1968:418961.
Chemical Abstract: CA 1969:68209.
Chemical Abstract: CA 1986:514976.
Chemical Abstract: CA 1987:458985.
Chemical Abstract: CA 1990:234572.
Chemical Abstract: CA 384846-70-2, 1990.

Danieli, B. et al. "Application of the PD-catalyzed hetroarylation to the synthesis of 5-(indol2'-yl)pyridin-2-one and 5-(indo1-2'yl) pyran-2-one" Tetrahedron, vol. 54, No. 46, 1998, p. 14081.

DeFrancesco, R., et al., "RNA-dependent RNA polymerase of hepatitis C virus". Methods in Enzymology, vol. 275, 1998, pp. 58-67.

Deutsch, M. et al; "Old and emerging therapies in chronic hepatitis C: an update;" 2008, J. of Viral Hepatitis, 15, p. 2-11.

Erhardt et al, "Safety, Pharmacokinetics and Antiviral effects of Boehringer Ingelheim BILB 1941, a Novel HCV RNA Polymerase, After 5 days Oral treatment in Patients with Chronic Hepatitis C", Poster from EASL 42nd Mtg. of Euruopean Association for the Study of Liver Diseases, Barcelona, Spain Apr. 11-15, 2007.

Ferrari, E., et al., "Characterization of soluble hepatitis C virus RNA-dependent RNA polymerase expressed in *Escherichia coli*". Journal of Virology, 1990, vol. 73, No. 2., pp. 1649-1654.

Fuerstner, A. et al; "Titanium-Induced Zipper Reactions"; Angewandte Chemie, International Edition in English (1995), 34(6),pp. 678-681 (XP-002233857).

Gale, M.J.et al., "Evidence that hepatitis C virus resistance to interferon is mediated through repression of the PKR protein kinase by the nonstructural 5A protein". Virology, 230, 1997, Article No. VY978493, pp. 217-227.

Grakoui, A., et al., "A second hepatitis C virus-encoded proteinase". Proc. Natl. Acad. Sci, USA, vol. 90, Nov. 1993, Biochemistry, pp. 10583-10587.

Grakoui, A., et al., "Expression and identification of hepatitis C virus polyprotein cleavage products". Journal of Virology, 193, vol. 67, No. 3, pp. 1385-1395, 1993.

Hashimoto, et al., WO 2001047883; CA 135:76874,2001.

VIRAL POLYMERASE INHIBITORS

This application is a U.S. National Stage application of PCT/CA2006/001292 filed Aug. 3, 2006, which claims the benefit of U.S. Provisional Application Ser. No. 60/707,769 filed on Aug. 12, 2005.

FIELD OF THE INVENTION

The invention relates to inhibitors of RNA dependent RNA polymerases, particularly those viral polymerases within the Flaviviridae family, more particularly to HCV polymerase.

BACKGROUND OF THE INVENTION

About 30,000 new cases of hepatitis C virus (HCV) infection are estimated to occur in the United States each year (Kolykhalov, A. A.; Mihalik, K.; Feinstone, S. M.; Rice, C. M.; 2000; *J. Viral.* 74: 2046-2051). HCV is not easily cleared by the hosts' immunological defenses; as many as 85% of the people infected with HCV become chronically infected. Many of these persistent infections result in chronic liver disease, including cirrhosis and hepatocellular carcinoma (Hoofnagle, J. H.; 1997; *Hepatology* 26: 15S-20S). There are an estimated 170 million HCV carriers world-wide, and HCV-associated end-stage liver disease is now the leading cause of liver transplantation. In the United States alone, hepatitis C is responsible for 8,000 to 10,000 deaths annually. Without effective intervention, the number is expected to triple in the next 10 to 20 years. There is no vaccine to prevent HCV infection.

Currently, the only approved therapy for patients chronically infected with HCV is treatment with interferon or a combination of interferon and ribavirin. Recently, pegylated versions of interferon (peginterferon alpha-2a (Pegasys™, Roche) and peginterferon alpha-2b (PEG-Intron™, Schering)) have been approved for marketing in some countries for treatment of chronic hepatitis C infection, both alone and in combination with ribavirin. However, it has been reported that these therapies achieve a sustained response in fewer than 60% of cases.

HCV belongs to the family Flaviviridae, genus *Hepacivirus*, which comprises three genera of small enveloped positive-strand RNA viruses (Rice, C. M.; 1996; "Flaviviridae: the viruses and their replication"; pp. 931-960 in *Fields Virology*; Fields, B. N.; Knipe, D. M.; Howley, P. M. (eds.); Lippincott-Raven Publishers, Philadelphia Pa.). The 9.6 kb genome of HCV consists of a long open reading frame (ORF) flanked by 5' and 3' non-translated regions (NTR's). The HCV 5' NTR is 341 nucleotides in length and functions as an internal ribosome entry site for cap-independent translation initiation (Lemon, S. H.; Honda, M.; 1997; *Semin. Virol.* 8: 274-288). The HCV polyprotein is cleaved co- and post-translationally into at least 10 individual polypeptides (Reed, K. E.; Rice, C. M.; 1999; *Curr. Top. Microbiol. Immunol.* 242: 55-84). Cleavage of the structural proteins in the N-terminal portion of the polyprotein is mediated by signal peptidases. Two viral proteases mediate downstream cleavages to produce non-structural (NS) proteins that function as components of the HCV RNA replicase. The NS2-3 protease spans the C-terminal half of the NS2 and the N-terminal one-third of NS3 and catalyses cis cleavage of the NS2/3 site. The same portion of NS3 also encodes the catalytic domain of the NS3-4A serine protease that cleaves at four downstream sites. The C-terminal two-thirds of NS3 is highly conserved amongst HCV isolates, with RNA-binding, RNA-stimulated NTPase, and RNA unwinding activities. Although NS4B and the NS5A phosphoprotein are also likely components of the replicase, their specific roles are unknown. The C-terminal polyprotein cleavage product, NS5B, is the elongation subunit of the HCV replicase possessing RNA-dependent RNA polymerase (RdRp) activity (Behrens, S. E.; Tomei, L.; DeFrancesco, R.; 1996; *EMBO J.* 15: 12-22; and Lohmann, V.; Körner, F.; Herian, U.; Bartenschlager, R.; 1997; *J. Virol.* 71: 8416-8428). It has been recently demonstrated that mutations destroying NS5B activity abolish infectivity of RNA in a chimp model (Kolykhalov, A. A.; Mihalik, K.; Feinstone, S. M.; Rice, C. M.; 2000; *J. Virol.* 74: 2046-2051).

The development of new and specific anti-HCV treatments is a high priority, and virus-specific functions essential for replication are the most attractive targets for drug development. The absence of RNA dependent RNA polymerases in mammals, and the fact that this enzyme appears to be essential to viral replication, would suggest that the NS5B polymerase is an ideal target for anti-HCV therapeutics. WO 01/47883, WO 02/04425, WO 03/000254, WO 03/007945, WO 03/010140, WO 03/010141, WO 2004/065367, WO 2004/064925, WO 2004/087714 and WO 2005/014543 report inhibitors of NS5B proposed for treatment of HCV.

SUMMARY OF THE INVENTION

The present invention provides a novel series of compounds having inhibitory activity against HCV polymerase. In particular, compounds according to this invention inhibit RNA synthesis by the RNA dependent RNA polymerase of HCV, especially the enzyme NS5B encoded by HCV. Furthermore, the compounds of the invention have activity as inhibitors in a cell-based HCV RNA replication assay. A further advantage of compounds provided by this invention is their low to very low or even non-significant activity against other polymerases. Further objects of this invention arise for the one skilled in the art from the following description and the examples.

Included in the scope of the invention is a compound represented by formula (I):

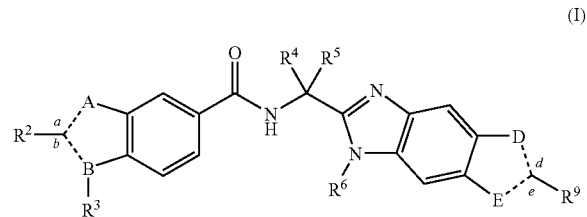

(I)

wherein:
either A is N or $CR^1$ and B is N, wherein bond a is a double bond and bond b is a single bond; or
A is $NR^1$ and B is C, wherein bond a is a single bond and bond b is a double bond;
$R^1$ is H, $(C_{1-6})$alkyl or a group of formula $-CH_2C(=O)N(R^{11})R^{12}$;
wherein $R^{11}$ is selected from H, $-O-(C_{1-6})$alkyl, $-SO_2-(C_{1-6})$alkyl, $(C_{1-6})$alkyl, $(C_{3-7})$cycloalkyl, $(C_{3-7})$cycloalkyl-$(C_{1-4})$alkyl-, $(C_{2-6})$alkenyl, $(C_{2-6})$alkynyl, aryl, Het, aryl-$(C_{1-4})$alkyl- and Het-$(C_{1-4})$alkyl-; wherein each of the $(C_{1-6})$alkyl, $(C_{3-7})$cycloalkyl, $(C_{3-7})$cycloalkyl-$(C_{1-4})$alkyl-, $(C_{2-6})$alkenyl, $(C_{2-6})$alkynyl, aryl, Het, aryl-$(C_{1-4})$alkyl- and Het-$(C_{1-4})$alkyl- is optionally substituted with $R^{15}$; and $R^{12}$ is selected from H, $(C_{1-6})$alkyl, $(C_{3-7})$cycloalkyl and $(C_{3-7})$cycloalkyl-$(C_{1-4})$alkyl-; wherein each of the $(C_{1-6})$alkyl, $(C_{3-7})$cycloalkyl and $(C_{3-7})$cycloalkyl-$(C_{1-4})$alkyl- is optionally substituted with one or more substituents each independently selected from —OH, halo, —COOH, —COO$(C_{1-6})$alkyl, $(C_{1-6})$alkyl, —O—$(C_{1-6})$alkyl, —NH$_2$, —NH$(C_{1-6})$alkyl and —N(($C_{1-6}$)alkyl)$_2$; or the groups $R^{11}$ and $R^{12}$ may be covalently bonded together along with the N to which they are attached to form a 4-, 5-, 6- or 7-membered saturated, unsaturated or aromatic N-containing heterocycle or a 8-, 9-, 10- or 11-membered saturated, unsaturated or aromatic N-containing bicyclic heteropolycycle, each of the heterocycle and heteropolycycle optionally containing from 1 to 3 additional heteroatoms selected from O, N, and S and each of the heterocycle and heteropolycycle being optionally substituted with $R^{15}$;

wherein $R^{15}$ is one to four substituents each independently selected from halo, oxo, $(C_{1-6})$alkyl, $(C_{1-6})$haloalkyl, —CO$(C_{1-6})$alkyl, —COOH, —COO$(C_{1-6})$alkyl, —CONH$_2$, —CONH$(C_{1-6})$alkyl, —CON(($C_{1-6}$)alkyl)$_2$, —OH, —SH, —NH$_2$, —NH$(C_{1-6})$alkyl, —N(($C_{1-6}$)alkyl)$_2$, —NHCO$(C_{1-6})$alkyl, —N($(C_{1-6})$alkyl)-CO$(C_{1-6})$alkyl, —NHCO—O$(C_{1-6})$alkyl, —N($(C_{1-6})$alkyl)-CO—O$(C_{1-6})$alkyl, —O—$(C_{1-6})$alkyl, —S—$(C_{1-6})$alkyl, —SO—$(C_{1-6})$alkyl, —SO$_2$—$(C_{1-6})$alkyl, nitro, cyano, azido, aryl, aryl-$(C_{1-6})$alkyl-, Het and Het-$(C_{1-6})$alkyl-;

wherein the $(C_{1-6})$alkyl is optionally substituted with —OH, —O—$(C_{1-6})$alkyl, —COOH, —COO$(C_{1-6})$alkyl, —CONH$_2$, —CONH$(C_{1-6})$alkyl, —CON(($C_{1-6})$alkyl)$_2$, —NH$_2$, —NH$(C_{1-6})$alkyl or —N(($C_{1-6})$alkyl)$_2$; and wherein the Het is optionally substituted with $(C_{1-6})$alkyl, $(C_{3-7})$cycloalkyl or $(C_{3-7})$cycloalkyl-$(C_{1-4})$alkyl-;

$R^2$ is selected from H, $(C_{1-6})$alkyl, $(C_{2-6})$alkenyl, $(C_{3-7})$cycloalkyl, aryl and Het; wherein the aryl and Het are each optionally substituted with $R^{21}$;

wherein $R^{21}$ is one, two or three substituents each independently selected from —OH, —SH, —CN, —NH$_2$, —NH$(C_{1-6})$alkyl, —N(($C_{1-6})$alkyl)$_2$, halo, $(C_{1-6})$alkyl, $(C_{1-6})$haloalkyl, $(C_{3-6})$cycloalkyl, —O—$(C_{1-6})$alkyl, —O—$(C_{1-6})$haloalkyl, —S—$(C_{1-6})$alkyl, —S—$(C_{1-6})$haloalkyl, —SO—$(C_{1-6})$alkyl-, SO—$(C_{1-6})$haloalkyl, —SO$_2$—$(C_{1-6})$alkyl, —SO$_2$—$(C_{1-6})$haloalkyl, aryl, Het, —CONH$_2$, —CONH$(C_{1-6})$alkyl and —CON(($C_{1-6})$alkyl)$_2$; wherein the —O—$(C_{1-6})$alkyl is optionally substituted with Het or aryl;

wherein each of the Het and aryl is optionally substituted with one to four substituents each independently selected from halo, aryl, Het, —N($R^{210}$)$R^{211}$, —N($R^{210}$)—C(═O)—$(C_{1-6})$alkyl and —C(═O)—N($R^{210}$)$R^{211}$;

wherein the aryl and Het are each optionally substituted with one to four substituents each independently selected from $(C_{1-6})$alkyl, halo, —N($R^{210}$)$_2$, —N($R^{210}$)—C(═O)—$(C_{1-6})$alkyl and —C(═O)—N($R^{210}$)$_2$;

$R^{210}$ is selected independently in each instance from H and $(C_{1-6})$alkyl; and $R^{211}$ is selected independently in each instance from H, $(C_{1-6})$alkyl, $(C_{3-7})$cycloalkyl and aryl; or $R^{210}$ and $R^{211}$ are linked, together with the N to which they are attached, to form a 5- or 6-membered saturated or unsaturated heterocycle, wherein said heterocycle is optionally substituted with one or two substituents each independently selected from $(C_{1-6})$alkyl and oxo;

$R^3$ is $(C_{5-6})$cycloalkyl, optionally substituted with from one to four halo substituents;

$R^4$ and $R^5$ are each independently selected from $(C_{1-6})$alkyl; or $R^4$ and $R^5$ are covalently bonded together along with the carbon atom to which they are attached to form $(C_{3-7})$cycloalkyl, $(C_{5-7})$cycloalkenyl or a 4-, 5- or 6-membered heterocycle having from 1 to 3 heteroatoms each independently selected from O, N, and S;

wherein the $(C_{3-7})$cycloalkyl, $(C_{5-7})$cycloalkenyl and 4-, 5- or 6-membered heterocycle are each optionally substituted with $(C_{1-4})$alkyl;

$R^6$ is H or $(C_{1-6})$alkyl;

either D is $CR^7$ and E is selected from O, S and $NR^8$, wherein bond d is a double bond and bond e is a single bond; or D is selected from O, S and $NR^7$ and E is $CR^8$, wherein bond d is a single bond and bond e is a double bond;

wherein $R^7$ and $R^8$ are each independently selected from H, $(C_{1-6})$alkyl and halo; and $R^9$ is —COOH, —CONH$_2$, —CONH$(C_{1-6})$alkyl, —CON(($C_{1-6})$alkyl)$_2$, tetrazolyl, —CONHSO$_2$$R^{90}$, or —CONHSO$_2$N($R^{91}$)$R^{90}$, wherein $R^{90}$ is selected from $(C_{1-6})$alkyl, $(C_{3-7})$cycloalkyl, $(C_{3-7})$cycloalkyl-$(C_{1-4})$alkyl-, aryl, aryl-$(C_{1-4})$alkyl, Het, and Het-$(C_{1-4})$alkyl; and $R^{91}$ is selected from H and $(C_{1-6})$alkyl;

wherein Het is defined as a 4- to 7-membered heterocycle having 1 to 4 heteroatoms each independently selected from O, N and S, which may be saturated, unsaturated or aromatic, and which is optionally fused to at least one other cycle to form a 7 to 14-membered heteropolycycle having wherever possible 1 to 5 heteroatoms, each independently selected from O, N and S, the heteropolycycle being saturated, unsaturated or aromatic;

or a salt thereof, an ester thereof, or a derivative thereof.

Included within the scope of this invention are derivatives of compounds of the formula (I) as described hereinbefore, comprising at least one of a detectable label, an affinity tag and a photoreactive group.

Another aspect of this invention provides a compound of formula (I) or a pharmaceutically acceptable salt or ester thereof, as a medicament.

Still another aspect of this invention provides a pharmaceutical composition comprising a therapeutically effective amount of a compound of formula (I) or a pharmaceutically acceptable salt or ester thereof; and one or more pharmaceutically acceptable carriers.

According to an embodiment of this aspect, the pharmaceutical composition according to this invention additionally comprises at least one other antiviral agent.

The invention also provides the use of a pharmaceutical composition as described hereinabove for the treatment of a hepatitis C viral infection in a mammal having or at risk of having the infection.

A further aspect of the invention involves a method of treating a hepatitis C viral infection in a mammal having or at risk of having the infection, the method comprising administering to the mammal a therapeutically effective amount of a compound of formula (I), a pharmaceutically acceptable salt or ester thereof, or a composition thereof as described hereinabove.

Another aspect of the invention involves a method of treating a hepatitis C viral infection in a mammal having or at risk of having the infection, the method comprising administering to the mammal a therapeutically effective amount of a combination of a compound of formula (I) or a pharmaceutically acceptable salt or ester thereof, and at least one other antiviral agent; or a composition thereof.

Also within the scope of this invention is the use of a compound of formula (I) as described herein, or a pharmaceutically acceptable salt or ester thereof, for the treatment of a hepatitis C viral infection in a mammal having or at risk of having the infection.

Another aspect of this invention provides the use of a compound of formula (I) as described herein, or a pharmaceutically acceptable salt or ester thereof, for the manufacture of a medicament for the treatment of a hepatitis C viral infection in a mammal having or at risk of having the infection.

An additional aspect of this invention refers to an article of manufacture comprising a composition effective to treat a hepatitis C viral infection; and packaging material comprising a label which indicates that the composition can be used to treat infection by the hepatitis C virus; wherein the composition comprises a compound of formula (I) according to this invention or a pharmaceutically acceptable salt or ester thereof.

Still another aspect of this invention relates to a method of inhibiting the replication of hepatitis C virus comprising exposing the virus to an effective amount of the compound of formula (I) according to this invention, or a salt or ester thereof, under conditions where replication of hepatitis C virus is inhibited.

Further included in the scope of the invention is the use of a compound of formula (I), or a salt or ester thereof, to inhibit the replication of hepatitis C virus.

DETAILED DESCRIPTION OF THE INVENTION

Definitions

As used herein, the following definitions apply unless otherwise noted:

The term "derivative thereof" as used herein is intended to mean a compound to which at least one of a detectable label, an affinity tag and a photoreactive group is linked.

The term "detectable label" as used herein is intended to mean any group that may be linked to a compound according to the present invention such that when the compound is associated with the polymerase target, such label allows recognition either directly or indirectly of the compound such that it can be detected, measured and quantified. Examples of such "labels" include, but are not limited to, fluorescent labels, chemiluminescent labels, colorimetric labels, enzymatic markers, radioactive isotopes and affinity tags such as biotin. Such labels are attached to the compound by well known methods.

The term "affinity tag" as used herein is intended to mean a ligand that may be linked to a compound of the present invention such that the strong affinity of the ligand for a receptor can be used to extract from a solution the entity to which the ligand is attached. Examples of such ligands include, but are not limited to, biotin or a derivative thereof, a histidine polypeptide, a polyarginine, an amylose sugar moiety or a defined epitope recognizable by a specific antibody. Such affinity tags are attached to the compound by well-known methods.

The term "photoreactive group" as used herein is intended to mean a group that is transformed, upon activation by light, from an inert group to a reactive species, such as a free radical. Such a group may be used as, for example, a photoaffinity label. Examples of such groups include, but are not limited to, benzophenones, azides, and the like.

The term "substituent", as used herein and unless specified otherwise, is intended to mean an atom, radical or group which may be bonded to a carbon atom, a heteroatom or any other atom which may form part of a molecule or fragment thereof, which would otherwise be bonded to at least one hydrogen atom. Substituents contemplated in the context of a specific molecule or fragment thereof are those which give rise to chemically stable compounds, such as are recognized by those skilled in the art.

The term "$(C_{1-n})$alkyl" as used herein, wherein n is an integer, either alone or in combination with another radical, is intended to mean acyclic, straight or branched chain alkyl radicals containing from 1 to n carbon atoms. "$(C_{1-6})$alkyl" includes, but is not limited to, methyl, ethyl, propyl(n-propyl), butyl(n-butyl), 1-methylethyl (iso-propyl), 1-methylpropyl(sec-butyl), 2-methylpropyl(iso-butyl), 1,1-dimethylethyl (tert-butyl), pentyl and hexyl. The abbreviation Me denotes a methyl group; Et denotes an ethyl group, Pr denotes a propyl group and Bu denotes a butyl group.

The term "$(C_{2-n})$alkenyl", as used herein, wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl(vinyl), 1-propenyl, 2-propenyl, and 1-butenyl. Unless specified otherwise, the term "$(C_{2-n})$alkenyl" is understood to encompass individual stereoisomers where possible, including but not limited to (E) and (Z) isomers, and mixtures thereof. When a $(C_{2-n})$ alkenyl group is substituted, it is understood to be substituted on any carbon atom thereof which would otherwise bear a hydrogen atom, unless specified otherwise.

The term "$(C_{2-n})$alkynyl", as used herein, wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, and 1-butynyl. When a $(C_{2-n})$alkynyl group is substituted, it is understood to be substituted on any carbon atom thereof which would otherwise bear a hydrogen atom, unless specified otherwise.

The term "$(C_{3-m})$cycloalkyl" as used herein, wherein m is an integer, either alone or in combination with another radical, is intended to mean a cycloalkyl substituent containing from 3 to m carbon atoms and includes, but is not limited to, cyclopropyl, cyclobutyl, cyclopentyl, cyclohexyl and cycloheptyl.

The term "$(C_{3-m})$cycloalkyl-$(C_{1-n})$alkyl-" as used herein, wherein n and m are both integers, either alone or in combination with another radical, is intended to mean an alkyl radical having 1 to n carbon atoms as defined above which is itself substituted with a cycloalkyl radical containing from 3 to m carbon atoms as defined above. Examples of $(C_{3-7})$ cycloalkyl-$(C_{1-6})$alkyl- include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl and 2-cyclohexylethyl. When a $(C_{3-m})$cycloalkyl-$(C_{1-n})$alkyl- group is substituted, it is understood that substituents may be attached to either the cycloalkyl or the alkyl portion thereof or both, unless specified otherwise.

The term "$(C_{5-n})$cycloalkenyl" as used herein, wherein n is an integer, either alone or in combination with another radical, is intended to mean an unsaturated cyclic radical containing five to n carbon atoms. Examples include, but are not limited to, cyclopentenyl and cyclohexenyl.

The term "aryl" as used herein, either alone or in combination with another radical, is intended to mean a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, 1-naphthyl, 2-naphthyl, tetrahydronaphthyl and dihydronaphthyl.

The term "aryl-$(C_{1-n})$alkyl-" as used herein, wherein n is an integer, either alone or in combination with another radical, is intended to mean an alkyl radical having 1 to n carbon atoms as defined above which is itself substituted with an aryl radical as defined above. Examples of aryl-$(C_{1-n})$alkyl- include, but are not limited to, phenylmethyl(benzyl), 1-phenylethyl, 2-phenylethyl and phenylpropyl. When an aryl-$(C_{1-n})$alkyl- group is substituted, it is understood that substituents may be attached to either the aryl or the alkyl portion thereof or both, unless specified otherwise.

The term "Het" as used herein, either alone or in combination with another radical, is intended to mean a 4- to 7-membered heterocycle having 1 to 4 heteroatoms each independently selected from O, N and S, which may be saturated, unsaturated or aromatic, and which is optionally fused to at least one other cycle to form a 7- to 14-membered heteropolycycle having wherever possible 1 to 5 heteroatoms, each independently selected from O, N and S, the heteropolycycle being saturated, unsaturated or aromatic, unless specified otherwise. When a Het group is substituted, it is understood that substituents may be attached to any carbon atom or heteroatom thereof which would otherwise bear a hydrogen atom, unless specified otherwise.

The term "Het-$(C_{1-n})$alkyl-" as used herein and unless specified otherwise, wherein n is an integer, either alone or in combination with another radical, is intended to mean an alkyl radical having 1 to n carbon atoms as defined above which is itself substituted with a Het substituent as defined above. Examples of Het-$(C_{1-n})$alkyl- include, but are not limited to, thienylmethyl, furylmethyl, piperidinylethyl, 2-pyridinylmethyl, 3-pyridinylmethyl, 4-pyridinylmethyl, quinolinylpropyl, and the like. When an Het-$(C_{1-n})$alkyl- group is substituted, it is understood that substituents may be attached to either the Het or the alkyl portion thereof or both, unless specified otherwise.

The term "heteroatom" as used herein is intended to mean O, S or N.

The term "heterocycle" as used herein and unless specified otherwise, either alone or in combination with another radical, is intended to mean a 3- to 7-membered saturated, unsaturated or aromatic heterocycle containing from 1 to 4 heteroatoms each independently selected from O, N and S; or a monovalent radical derived by removal of a hydrogen atom therefrom. Examples of such heterocycles include, but are not limited to, azetidine, pyrrolidine, tetrahydrofuran, tetrahydrothiophene, thiazolidine, oxazolidine, pyrrole, thiophene, furan, pyrazole, imidazole, isoxazole, oxazole, isothiazole, thiazole, triazole, tetrazole, piperidine, piperazine, azepine, diazepine, pyran, 1,4-dioxane, 4-morpholine, 4-thiomorpholine, pyridine, pyridine-N-oxide, pyridazine, pyrazine and pyrimidine.

The term "heteropolycycle" as used herein and unless specified otherwise, either alone or in combination with another radical, is intended to mean a heterocycle as defined above fused to one or more other cycle, including a carbocycle, a heterocycle or any other cycle; or a monovalent radical derived by removal of a hydrogen atom therefrom. Examples of such heteropolycycles include, but are not limited to, indole, benzimidazole, benzothiophene, benzofuran, benzodioxole, benzothiazole, quinoline, isoquinoline, and naphthyridine.

The term "halo" as used herein is intended to mean a halogen substituent selected from fluoro, chloro, bromo or iodo.

The term "$(C_{1-n})$haloalkyl" as used herein, wherein n is an integer, either alone or in combination with another radical, is intended to mean an alkyl radical having 1 to n carbon atoms as defined above wherein one or more hydrogen atoms are each replaced by a halo substituent. Examples of $(C_{1-n})$haloalkyl include but are not limited to chloromethyl, chloroethyl, dichloroethyl, bromomethyl, bromoethyl, dibromoethyl, fluoromethyl, difluoromethyl, trifluoromethyl, fluoroethyl and difluoroethyl.

The terms "—O—$(C_{1-n})$alkyl" or "$(C_{1-n})$alkoxy" as used herein interchangeably, wherein n is an integer, either alone or in combination with another radical, is intended to mean an oxygen atom further bonded to an alkyl radical having 1 to n carbon atoms as defined above. Examples of —O—$(C_{1-n})$alkyl include but are not limited to methoxy ($CH_3O$—), ethoxy ($CH_3CH_2O$—), propoxy ($CH_3CH_2CH_2O$—), 1-methylethoxy (iso-propoxy; $(CH_3)_2CH$—O—) and 1,1-dimethylethoxy (tert-butoxy; $(CH_3)_3C$—O—). When an —O—$(C_{1-n})$alkyl radical is substituted, it is understood to be substituted on the $(C_{1-n})$alkyl portion thereof.

The terms "—S—$(C_{1-n})$alkyl" or "$(C_{1-n})$alkylthio" as used herein interchangeably, wherein n is an integer, either alone or in combination with another radical, is intended to mean an sulfur atom further bonded to an alkyl radical having 1 to n carbon atoms as defined above. Examples of —S—$(C_{1-n})$alkyl include but are not limited to methylthio ($CH_3S$—), ethylthio ($CH_3CH_2S$—), propylthio ($CH_3CH_2CH_2S$—), 1-methylethylthio (isopropylthio; $(CH_3)_2CH$—S—) and 1,1-dimethylethylthio (tert-butylthio; $(CH_3)_3C$—S—). When —S—$(C_{1-n})$alkyl radical, or an oxidized derivative thereof, such as an —SO—$(C_{1-n})$alkyl radical or an —$SO_2$—$(C_{1-n})$alkyl radical, is substituted, each is understood to be substituted on the $(C_{1-n})$alkyl portion thereof.

The term "oxo" as used herein is intended to mean an oxygen atom attached to a carbon atom as a substituent by a double bond (=O).

The term "thioxo" as used herein is intended to mean an sulfur atom attached to a carbon atom as a substituent by a double bond (=S).

The term "COOH" as used herein is intended to mean a carboxyl group (—C(=O)—OH). It is well known to one skilled in the art that carboxyl groups may be substituted by functional group equivalents. Examples of such functional group equivalents contemplated in this invention include, but are not limited to, esters, amides, imides, boronic acids, phosphonic acids, phosphoric acids, tetrazoles, triazoles, N-acylsulfamides ($RCONHSO_2NR_2$), and N-acylsulfonamides ($RCONHSO_2R$).

The term "functional group equivalent" as used herein is intended to mean an atom or group that may replace another atom or group which has similar electronic, hybridization or bonding properties.

The term "protecting group" as used herein is intended to mean protecting groups that can be used during synthetic transformation, including but not limited to examples which are listed in Greene, "Protective Groups in Organic Chemistry", John Wiley & Sons, New York (1981), and more recent editions thereof.

The following designation

is used in sub-formulas to indicate the bond which is connected to the rest of the molecule as defined.

The term "salt thereof" as used herein is intended to mean any acid and/or base addition salt of a compound according to the invention, including but not limited to a pharmaceutically acceptable salt thereof.

The term "pharmaceutically acceptable salt" as used herein is intended to mean a salt of a compound according to the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, for example, S. M. Birge et al., J. Pharm. Sci., 1977, 66, pp. 1-19.

The term "pharmaceutically-acceptable acid addition salt" as used herein is intended to mean those salts which retain the biological effectiveness and properties of the free bases and which are not biologically or otherwise undesirable, formed with inorganic acids including but not limited to hydrochloric acid, hydrobromic acid, sulfuric acid, sulfamic acid, nitric acid, phosphoric acid and the like, and organic acids including but not limited to acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid and the like.

The term "pharmaceutically-acceptable base addition salt" as used herein is intended to mean those salts which retain the biological effectiveness and properties of the free acids and which are not biologically or otherwise undesirable, formed with inorganic bases including but not limited to ammonia or the hydroxide, carbonate, or bicarbonate of ammonium or a metal cation such as sodium, potassium, lithium, calcium, magnesium, iron, zinc, copper, manganese, aluminum and the like. Particularly preferred are the ammonium, potassium, sodium, calcium, and magnesium salts. Salts derived from pharmaceutically-acceptable organic nontoxic bases include but are not limited to salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins and the like. Particularly preferred organic nontoxic bases are isopropylamine, diethylamine, ethanolamine, trimethylamine, dicyclohexylamine, choline, and caffeine.

The term "ester thereof" as used herein is intended to mean any ester of a compound according to the invention in which any of the —COON substituents of the molecule is replaced by a —COOR substituent, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl, each of which being optionally further substituted. The term "ester thereof" includes but is not limited to pharmaceutically acceptable esters thereof.

The term "pharmaceutically acceptable ester" as used herein is intended to mean esters of the compound according to the invention in which any of the COOH substituents of the molecule are replaced by a —COOR substituents, in which the R moiety of the ester is selected from alkyl (including, but not limited to, methyl, ethyl, propyl, 1-methylethyl, 1,1-dimethylethyl, butyl); alkoxyalkyl (including, but not limited to methoxymethyl); acyloxyalkyl (including, but not limited to acetoxymethyl); arylalkyl (including, but not limited to, benzyl); aryloxyalkyl (including, but not limited to, phenoxymethyl); and aryl (including, but not limited to phenyl) optionally substituted with halo, $(C_{1-4})$alkyl or $(C_{1-4})$alkoxy. Other suitable esters can be found in Design of Prodrugs, Bundgaard, H. Ed. Elsevier (1985). Such pharmaceutically acceptable esters are usually hydrolyzed in vivo when injected into a mammal and transformed into the acid form of the compound according to the invention. With regard to the esters described above, unless otherwise specified, any alkyl moiety present preferably contains 1 to 16 carbon atoms, more preferably 1 to 6 carbon atoms. Any aryl moiety present in such esters preferably comprises a phenyl group. In particular the esters may be a $(C_{1-16})$alkyl ester, an unsubstituted benzyl ester or a benzyl ester substituted with at least one halo, $(C_{1-6})$alkyl, $(C_{1-6})$alkoxy, nitro or trifluoromethyl.

The term "mammal" as used herein is intended to encompass humans, as well as non-human mammals which are susceptible to infection by hepatitis C virus including domestic animals, such as cows, pigs, horses, dogs and cats, and non-domestic animals.

The term "treatment" as used herein is intended to mean the administration of a compound or composition according to the present invention to alleviate or eliminate symptoms of the hepatitis C disease and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood.

Preferred Embodiments

Unless stated otherwise, all groups and substituents have the definitions as defined hereinbefore and hereinafter. In the following, the preferred embodiments, groups and substituents according to this invention are described.

A B D and E:

In one embodiment of the present invention are provided compounds wherein A is NR¹, B is C, bond a is a single bond and bond b is a double bond, such that the compounds have the general formula (Ia') below:

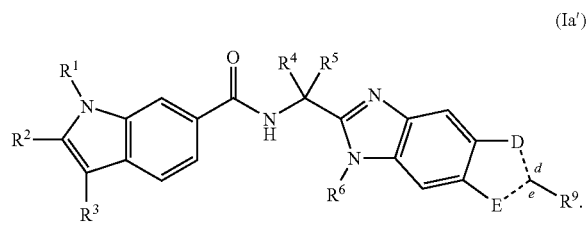
(Ia')

In an alternative embodiment of the present invention are provided compounds wherein A is CR¹, B is N, bond a is a double bond and bond b is a single bond, such that the compounds have the general formula (Ib') below:

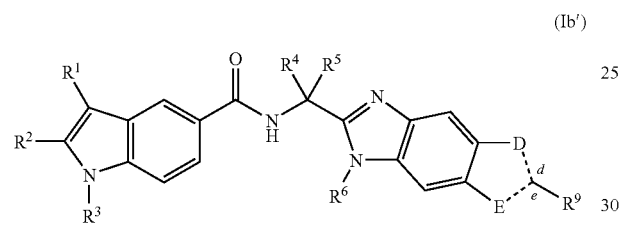
(Ib')

In another alternative embodiment of the present invention are provided compounds wherein A is N, B is N, bond a is a double bond and bond b is a single bond, such that the compounds have the general formula (Ic') below:

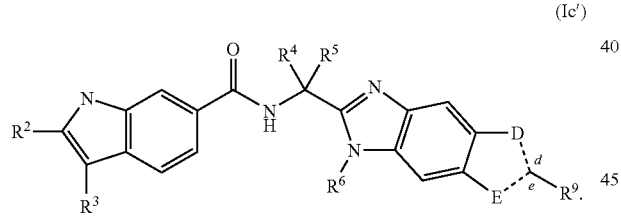
(Ic')

In yet another alternative embodiment of the present invention are provided compounds wherein D is selected from O, S and NR⁷ and E is CR⁸, wherein bond d is a single bond and bond e is a double bond, such that the compounds have the general formula (Id') below:

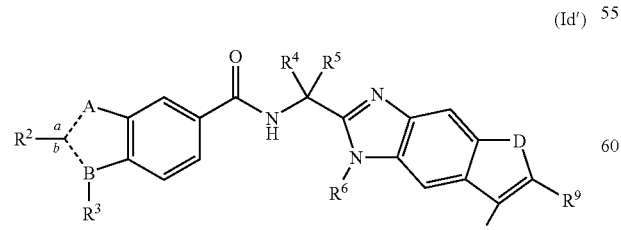
(Id')

In still another alternative embodiment of the present invention are provided compounds wherein D is CR⁷ and E is selected from O, S and NR⁸, wherein bond d is a double bond and bond e is a single bond, such that the compounds have the general formula (Ie') below:

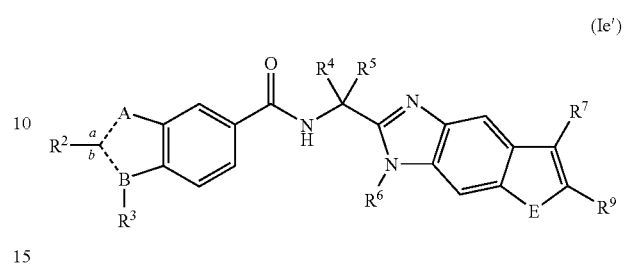
(Ie')

Therefore, the invention preferably provides compounds of the general formulas (If') to (Ik') below:

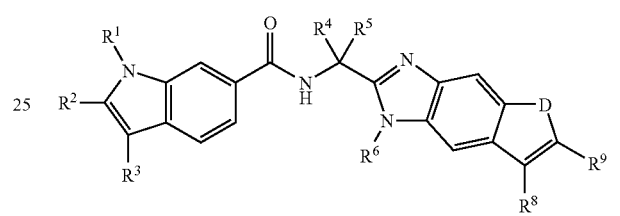
(If')

(Ig')

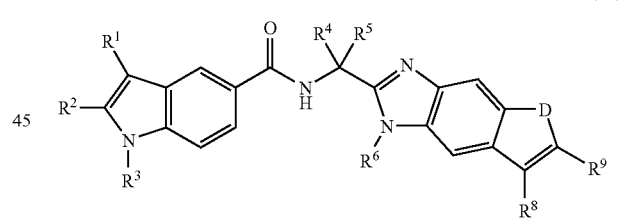
(Ih')

(Ii')

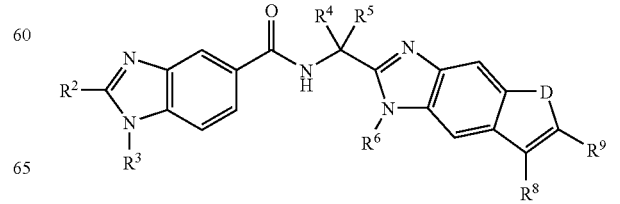
(Ij')

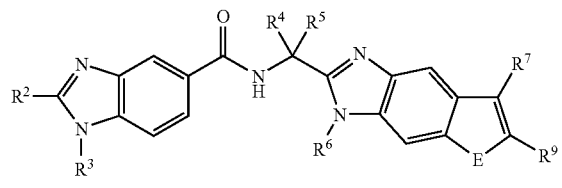
(Ik')
More preferably, the invention provides compounds of the general formulas (Ia) to (Is) below:
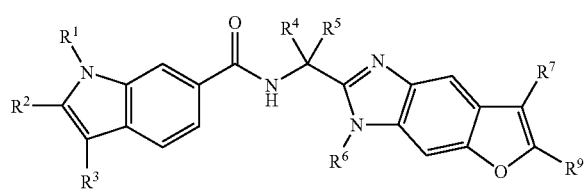
(Ia)
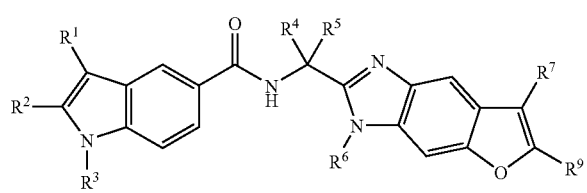
(Ib)
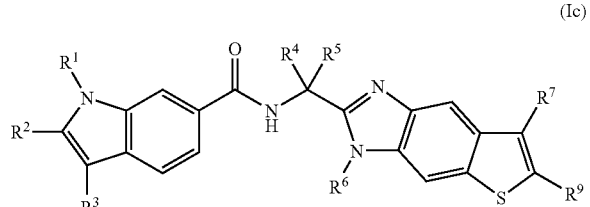
(Ic)
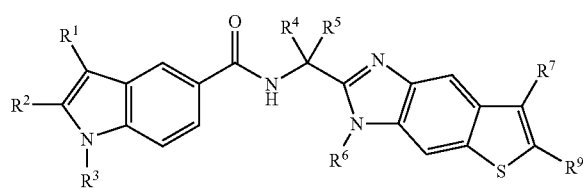
(Id)
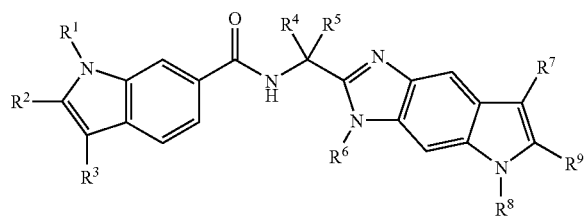
(Ie)
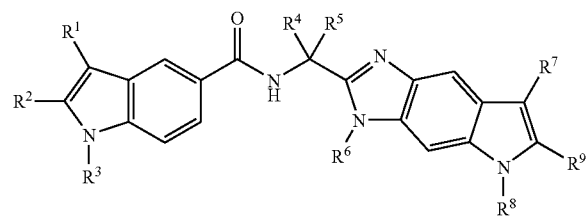
(If)
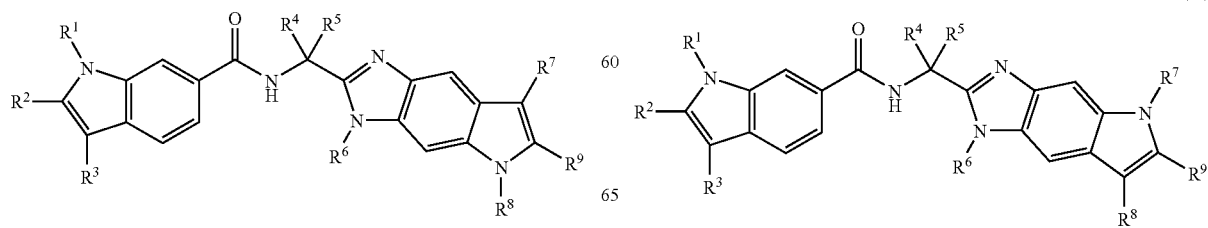

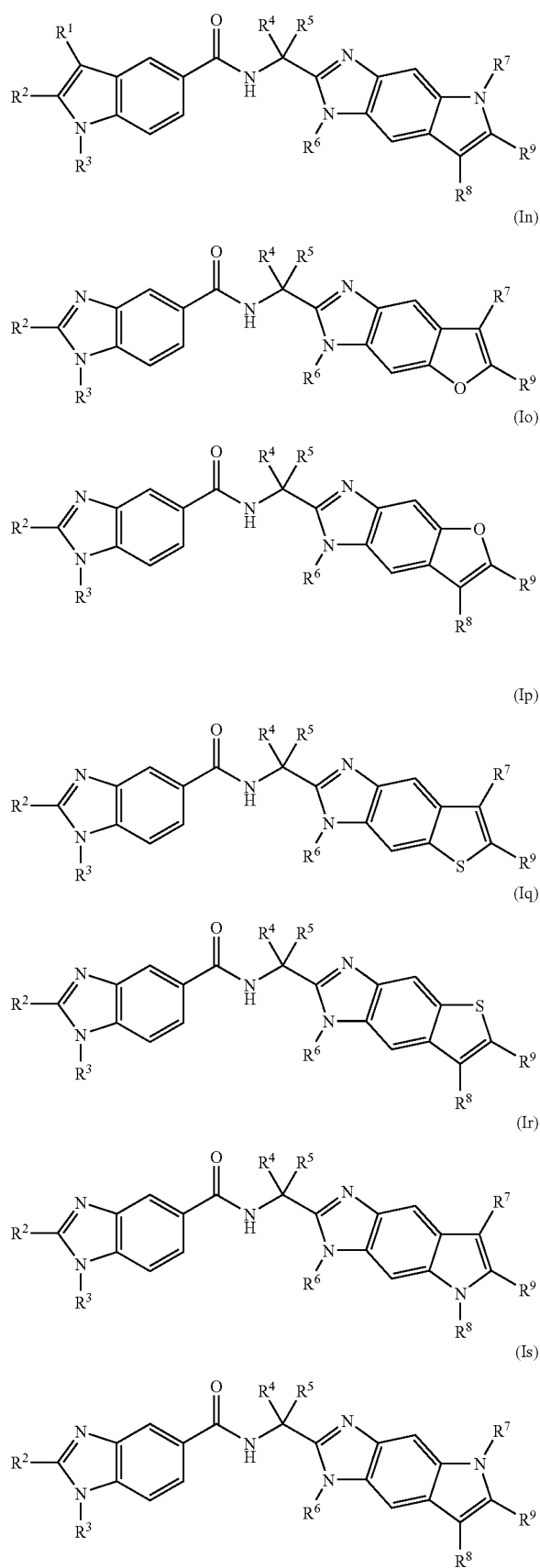

Any and each individual definition of A, B, D and E as set out herein may be combined with any and each individual definition of $R^1$, $R^2$, $R^3$, $R^4$, $R^5$, $R^6$, $R^7$, $R^8$ and $R^9$ as set out herein.

$R^1$:

According to a preferred embodiment of this invention $R^1$ is selected from H and $(C_{1-6})$alkyl.

More preferably, $R^1$ is selected from H and methyl.

Most preferably in this embodiment, $R^1$ is methyl.

According to another preferred embodiment of this invention, $R^1$ is a group of formula —$CH_2C(=O)N(R^{11})R^{12}$;

wherein $R^{11}$ is selected from H, $(C_{1-6})$alkyl, $(C_{3-7})$cycloalkyl, $(C_{3-7})$cycloalkyl-$(C_{1-4})$alkyl-, aryl, Het, aryl-$(C_{1-4})$alkyl- and Het-$(C_{1-4})$alkyl-; wherein Het is a 5- or 6-membered saturated, unsaturated or aromatic heterocycle containing 1 or 2 heteroatoms each independently selected from N, O and S, or Het is a 9- or 10-membered saturated, unsaturated or aromatic bicyclic heteropolycycle containing 1 or 2 heteroatoms each independently selected from N, O and S;

each of the $(C_{1-6})$alkyl, $(C_{3-7})$cycloalkyl, $(C_{3-7})$cycloalkyl-$(C_{1-4})$alkyl-, aryl, Het, aryl-$(C_{1-4})$alkyl- and Het-$(C_{1-4})$alkyl- being optionally substituted with $R^{15}$; and $R^{12}$ is selected from H, $(C_{1-6})$alkyl, $(C_{3-7})$cycloalkyl and $(C_{3-7})$cycloalkyl-$(C_{1-4})$alkyl-; wherein each of the $(C_{1-6})$alkyl, $(C_{3-7})$cycloalkyl and $(C_{3-7})$cycloalkyl-$(C_{1-4})$alkyl- is optionally substituted with one or more substituents each independently selected from —OH, halo, —COOH, —COO$(C_{1-6})$alkyl, $(C_{1-6})$alkyl, —O—$(C_{1-6})$alkyl, —$NH_2$, —NH$(C_{1-6})$alkyl and —N$((C_{1-6})$alkyl$)_2$; or the groups $R^{11}$ and $R^{12}$ may be covalently bonded together along with the N to which they are attached to form a 5-, 6- or 7-membered saturated, unsaturated or aromatic N-containing heterocycle or a 8-, 9-, 10- or 11-membered saturated, unsaturated or aromatic N-containing bicyclic heteropolycycle, each of the heterocycle and heteropolycycle optionally containing from 1 to 3 additional heteroatoms each independently selected from O, N, and S and each of the heterocycle and heteropolycycle being optionally substituted with $R^{15}$;

wherein $R^{15}$ is as defined herein.

More preferably in this embodiment, $R^{11}$ is selected from H, methyl, ethyl, propyl, 1-methylethyl, butyl, 1-methylpropyl, 2-methylpropyl, 1,1-dimethylethyl, cyclobutyl, cyclopentyl, cyclohexyl, $(C_{4-6})$cycloalkylmethyl, $(C_{4-6})$cycloalkylethyl, phenyl, phenylmethyl, phenylethyl, Het, Het-methyl- and Het-ethyl-; wherein Het is a 5- or 6-membered saturated, unsaturated or aromatic heterocycle containing 1 or 2 heteroatoms each independently selected from N, O and S, or Het is a 9- or 10-membered saturated, unsaturated or aromatic bicyclic heteropolycycle containing 1 or 2 heteroatoms each independently selected from N, O and S;

each of the methyl, ethyl, propyl, 1-methylethyl, butyl, 1-methylpropyl, 2-methylpropyl, 1,1-dimethylethyl, cyclobutyl, cyclopentyl, cyclohexyl, $(C_{4-6})$cycloalkylmethyl, $(C_{4-6})$cycloalkylethyl; phenyl, phenylmethyl, phenylethyl, Het, Het-methyl- and Het-ethyl- being optionally substituted with $R^{15}$; and $R^{12}$ is selected from H, methyl, ethyl, propyl, 1-methylethyl, cyclopropyl and cyclopropylmethyl; or the groups $R^{11}$ and $R^{12}$ may be covalently bonded together along with the N to which they are attached to form

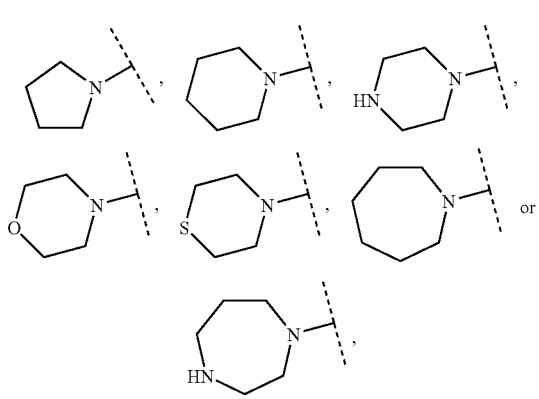

each of which being optionally substituted with $R^{15}$;
wherein $R^{15}$ is as defined herein.

Preferably, $R^{15}$ is one to three substituents each independently selected from fluorine, chlorine, bromine, methyl, ethyl, propyl, —COOH, —COO($C_{1-3}$)alkyl, —CONH$_2$, —CONH($C_{1-3}$)alkyl, —CON(($C_{1-3}$)alkyl)$_2$, —OH, —NH$_2$, —NH($C_{1-3}$)alkyl, —N(($C_{1-3}$)alkyl)$_2$, —O—($C_{1-3}$)alkyl, nitro, cyano, azido, phenyl, phenylmethyl,

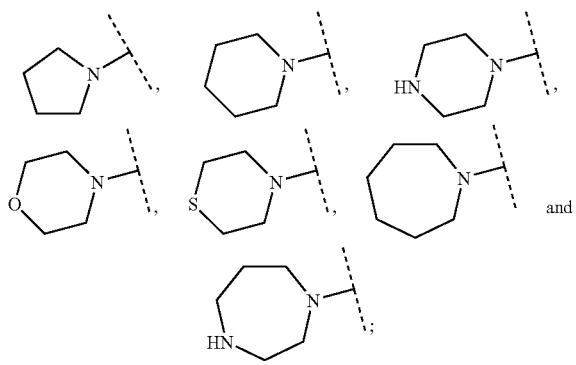

wherein each of the methyl, ethyl and propyl are optionally substituted with —OH, —O—($C_{1-3}$)alkyl, —COOH, —COO($C_{1-3}$)alkyl, —CONH$_2$, —CONH($C_{1-3}$)alkyl, —CON(($C_{1-3}$)alkyl)$_2$, —NH, —NH($C_{1-3}$)alkyl or —N(($C_{1-3}$)alkyl)$_2$; and wherein each of the

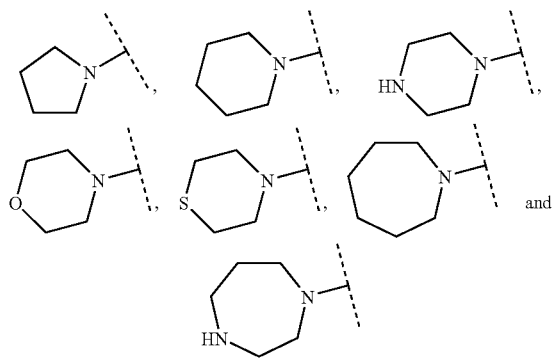

are optionally substituted with ($C_{1-3}$)alkyl.

Therefore, preferably in this embodiment, $R^1$ is selected from

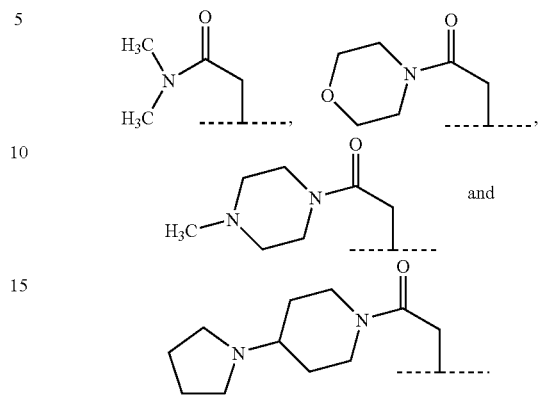

Any and each individual definition of $R^1$ as set out herein may be combined with any and each individual definition of A, B, D, E, $R^2$, $R^3$, $R^4$, $R^5$, $R^6$, $R^7$, $R^8$ and $R^9$ as set out herein.

$R^2$:

In a preferred embodiment, $R^2$ is H, ($C_{1-6}$)alkyl, ($C_{2-6}$)alkenyl or ($C_{3-7}$)cycloalkyl. More preferably within this embodiment, $R^2$ is H, methyl, ethyl, propyl, 1-methylethyl, ethenyl, propenyl, 1-methylethenyl, cyclopropyl, cyclobutyl, cyclopentyl or cyclohexyl. Alternatively more preferably within this embodiment, $R^2$ is H or ($C_{1-3}$)alkyl.

In an alternative preferred embodiment, $R^2$ is aryl or Het, wherein Het is a 5- or 6-membered aromatic heterocycle having 1 to 4 heteroatoms each independently selected from O, N and S;

wherein the aryl and Het are unsubstituted or substituted with $R^{21}$, wherein $R^{21}$ is as defined herein.

More preferably $R^2$ is phenyl or Het, wherein Het is selected from

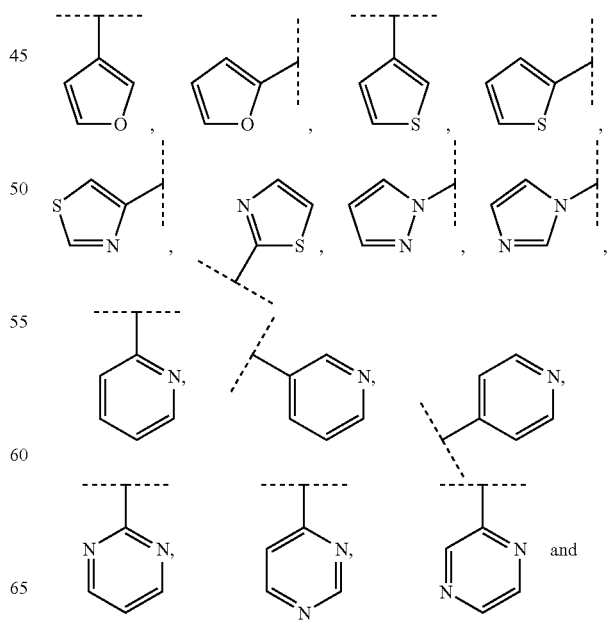

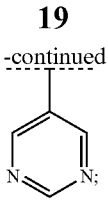

and wherein the phenyl and Het are unsubstituted or substituted with $R^{21}$, wherein $R^{21}$ is as defined herein.

Most preferably $R^2$ is phenyl or Het, wherein Het is selected from

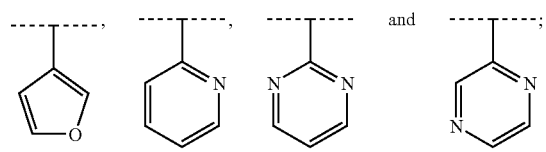

and wherein the phenyl and Het are unsubstituted or substituted with $R^{21}$, wherein $R^{21}$ is as defined herein.

Preferably, $R^{21}$ is one, two or three substituents each independently selected from $(C_{1-3})$alkyl, $(C_{1-3})$haloalkyl, $(C_{3-6})$cycloalkyl, —CN, —NH$_2$, —NH$(C_{1-3})$alkyl, —N$((C_{1-3})$alkyl$)_2$, halo, —O—$(C_{1-3})$alkyl, —O—$(C_{1-3})$haloalkyl, —S—$(C_{1-3})$alkyl, —S—$(C_{1-3})$haloalkyl, —SO—$(C_{1-3})$alkyl-, SO—$(C_{1-3})$haloalkyl, —SO$_2$—$(C_{1-3})$alkyl and —SO$_2$—$(C_{1-3})$haloalkyl.

More preferably, $R^{21}$ is one, two or three substituents each independently selected from fluoro, chloro, bromo, methyl, ethyl, propyl, 1-methylethyl, trifluoromethyl, cyclopropyl, cyclobutyl, cyclopentyl, cyclohexyl, methoxy, ethoxy, propoxy, 1-methylethoxy, methylthio, ethylthio, propylthio, 1-methylethylthio, amino, N-methylamino, N,N-dimethylamino and cyano.

Most preferably, $R^{21}$ is one or two substituents each independently selected from methoxy, fluoro, chloro and bromo.

Therefore, preferably, $R^2$ is selected from:

H, propyl,

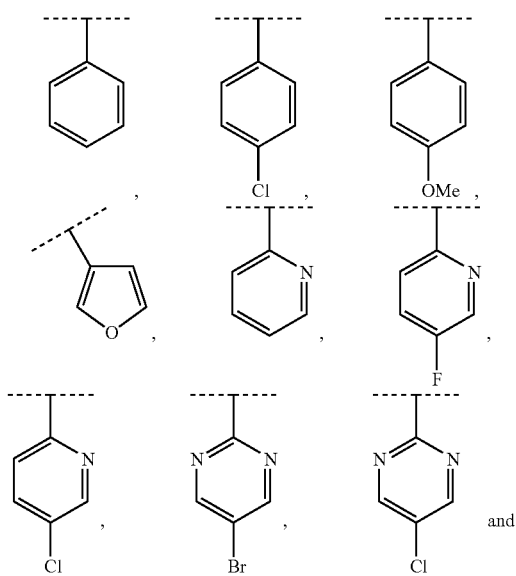

and

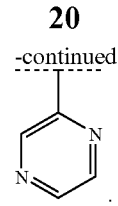

In an alternative embodiment, when $R^2$ is phenyl substituted with $R^{21}$, $R^{21}$ is —O—$(C_{1-6})$alkyl substituted with phenyl wherein the phenyl is optionally substituted with one to four substituents each independently selected from halo, phenyl, Het, —N$(R^{210})R^{211}$, —N$(R^{210})$—C(=O)—$(C_{1-6})$alkyl and —C(=O)—N$(R^{210})R^{211}$; wherein the Het is a 5- or 6-membered monocyclic saturated heterocycle; and wherein the phenyl and Het are each optionally substituted with one to four substituents each independently selected from $(C_{1-6})$alkyl, halo, —N$(R^{210})_2$, —N$(R^{210})$—C(=O)—$(C_{1-6})$alkyl and —C(=O)—N$(R^{210})_2$;

$R^{210}$ is selected independently in each instance from H and $(C_{1-6})$alkyl; and $R^{211}$ is selected independently in each instance from H, $(C_{1-6})$alkyl, $(C_{3-7})$cycloalkyl and aryl; or $R^{210}$ and $R^{211}$ are linked, together with the N to which they are attached, to form a 5- or 6-membered saturated or unsaturated heterocycle, wherein said heterocycle is optionally substituted with one or two substituents each independently selected from $(C_{1-6})$alkyl and oxo;

and $R^{21}$ is additionally optionally one or two substituents each independently selected from $(C_{1-3})$alkyl, $(C_{1-3})$haloalkyl, $(C_{3-6})$cycloalkyl, —CN, —NH$_2$, —NH$(C_{1-3})$alkyl, —N$((C_{1-3})$alkyl$)_2$, halo, —O—$(C_{1-3})$alkyl, —O—$(C_{1-3})$haloalkyl, —S—$(C_{1-3})$alkyl, —S—$(C_{1-3})$haloalkyl, —SO—$(C_{1-3})$alkyl-, SO—$(C_{1-3})$haloalkyl, —SO$_2$—$(C_{1-3})$alkyl and —SO$_2$—$(C_{1-3})$haloalkyl.

In a more preferable alternative embodiment, when $R^2$ is phenyl substituted with $R^{21}$, $R^{21}$ is —O—$(C_{1-6})$alkyl substituted with phenyl wherein the phenyl is optionally substituted with one to four substituents each independently selected from halo, phenyl, Het, —N$(R^{210})R^{211}$, —N$(R^{210})$—C(=O)—$(C_{1-6})$alkyl and —C(=O)—N$(R^{210})R^{211}$; wherein the Het is a 5- or 6-membered monocyclic saturated heterocycle; and wherein the phenyl and Het are each optionally substituted with one to four substituents each independently selected from $(C_{1-6})$alkyl, halo, —N$(R^{210})_2$, —N$(R^{210})$—C(=O)—$(C_{1-6})$alkyl and —C(=O)—N$(R^{210})_2$;

$R^{210}$ is selected independently in each instance from H and $(C_{1-6})$alkyl; and $R^{211}$ is selected independently in each instance from H, $(C_{1-6})$alkyl, $(C_{3-7})$cycloalkyl and aryl; or $R^{210}$ and $R^{211}$ are linked, together with the N to which they are attached, to form a 5- or 6-membered saturated or unsaturated heterocycle, wherein said heterocycle is optionally substituted with one or two substituents each independently selected from $(C_{1-6})$alkyl and oxo;

and $R^{21}$ is additionally optionally one or two substituents each independently selected from methoxy, fluoro, chloro and bromo.

More preferably in this embodiment, R² is selected from:

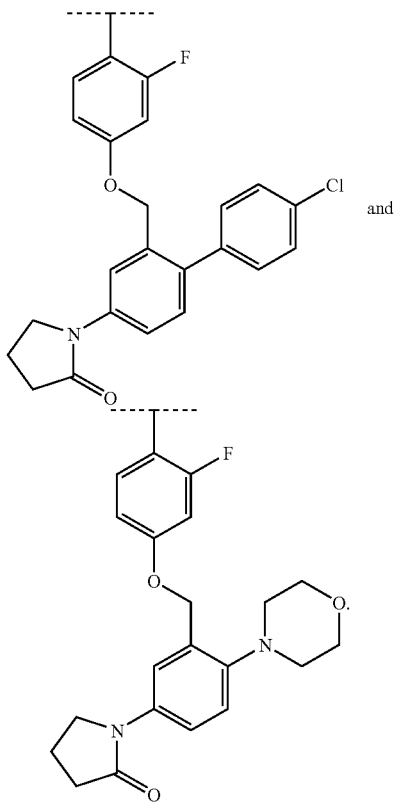

and

Any and each individual definition of R² as set out herein may be combined with any and each individual definition of A, B, D, E, R¹, R³, R⁴, R⁵, R⁶, R⁷, R⁸ and R⁹ as set out herein.

R³:
Preferably, R³ is cyclopentyl or cyclohexyl, each being optionally substituted with one or two fluoro substituents.
More preferably, R³ is cyclopentyl, cyclohexyl or 4,4-difluorocyclohexyl.
Any and each individual definition of R³ as set out herein may be combined with any and each individual definition of A, B, D, E, R¹, R², R⁴, R⁵, R⁶, R⁷, R⁸ and R⁹ as set out herein.

R⁴ and R⁵:
Preferably, R⁴ and R⁵ are each independently selected from (C$_{1-3}$)alkyl; or R⁴ and R⁵ are covalently bonded together along with the carbon atom to which they are attached to form (C$_{3-6}$)cycloalkyl, (C$_{5-6}$)cycloalkenyl or a 5- or 6-membered saturated or unsaturated heterocycle having 1 or 2 heteroatoms each independently selected from O and N; wherein the (C$_{3-6}$)cycloalkyl, (C$_{5-6}$)cycloalkenyl and 5- or 6-membered heterocycle are each optionally substituted with (C$_{1-4}$)alkyl.

More preferably, the group

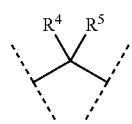

is selected from:

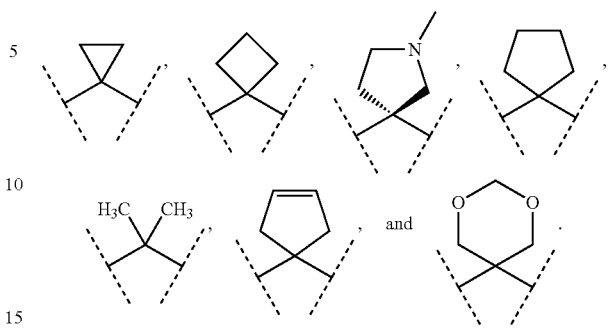

and

Most preferably, the group

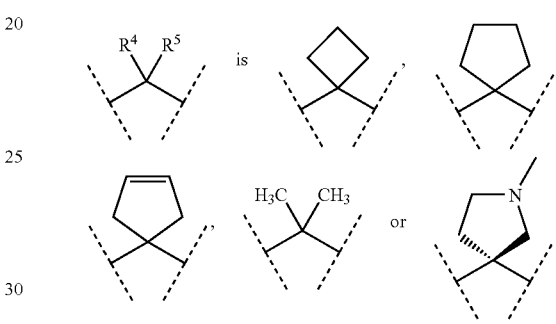

Any and each individual definition of R⁴ and R⁶ as set out herein may be combined with any and each individual definition of A, B, D, E, R¹, R², R³, R⁶, R⁷, R⁸ and R⁹ as set out herein.

R⁶:
Preferably, R⁶ is H, methyl or ethyl.
More preferably, R⁶ is H or methyl.
Most preferably, R⁶ is methyl.
Any and each individual definition of R⁶ as set out herein may be combined with any and each individual definition of A, B, D, E, R¹, R², R³, R⁴, R⁵, R⁶, R⁷, R⁸ and R⁹ as set out herein.

R⁷:
Preferably R⁷ is H or (C$_{1-6}$)alkyl.
More preferably R⁷ is H, methyl or ethyl.
Most preferably, R⁷ is H or methyl.
Any and each individual definition of R⁷ as set out herein may be combined with any and each individual definition of A, B, D, E, R¹, R², R³, R⁴, R⁵, R⁶, R⁸ and R⁹ as set out herein.

R⁸:
Preferably R⁸ is H or (C$_{1-6}$)alkyl.
More preferably R⁸ is H, methyl or ethyl.
Most preferably, R⁸ is H or methyl.
Any and each individual definition of R⁸ as set out herein may be combined with any and each individual definition of A, B, D, E, R¹, R², R³, R⁴, R⁵, R⁶, R⁷ and R⁹ as set out herein.

Preferably, when D is CR⁷ and E is NR⁸ or when D is NR⁷ and E is CR⁸, at least one of R⁷ and R⁸ is H.

R⁹:
Preferably, R⁹ is —COOH, —CONH₂, or —CONH(C$_{1-6}$)alkyl.
More preferably, R⁹ is —COOH, —CONH₂, or —CONHCH₃.
Most preferably, R⁹ is —COOH.

Any and each individual definition of $R^9$ as set out herein may be combined with any and each individual definition of A, B, D, E, $R^1$, $R^2$, $R^3$, $R^4$, $R^5$, $R^6$, $R^7$ and $R^8$ as set out herein.

Preferably provided are compounds selected from the general formulas (If′) to (Ik′):

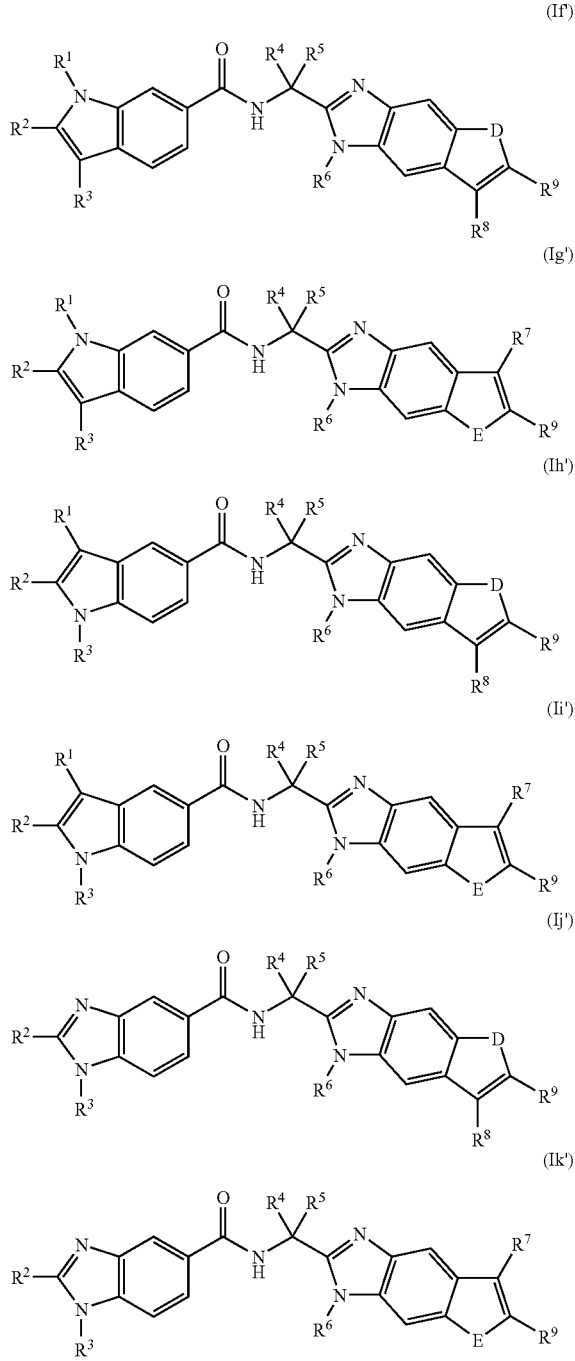

wherein:
$R^1$ is selected from H and methyl or $R^1$ is a group of formula —CH$_2$C(=O)N($R^{11}$)$R^{12}$;
wherein $R^{11}$ is selected from H, (C$_{1-6}$)alkyl, (C$_{3-7}$)cycloalkyl, (C$_{3-7}$)cycloalkyl-(C$_{1-4}$)alkyl-, aryl, Het, aryl-(C$_{1-4}$)alkyl- and Het-(C$_{1-4}$)alkyl-; wherein Het is a 5- or 6-membered saturated, unsaturated or aromatic heterocycle containing 1 or 2 heteroatoms each independently selected from N, O and S, or Het is a 9- or 10-membered saturated, unsaturated or aromatic bicyclic heteropolycycle containing 1 or 2 heteroatoms each independently selected from N, O and S;

each of the (C$_{1-6}$)alkyl, (C$_{3-7}$)cycloalkyl, (C$_{3-7}$)cycloalkyl-(C$_{1-4}$)alkyl-, aryl, Het, aryl-(C$_{1-4}$)alkyl- and Het-(C$_{1-4}$)alkyl- being optionally substituted with $R^{15}$; and $R^{12}$ is selected from H, (C$_{1-6}$)alkyl, (C$_{3-7}$)cycloalkyl and (C$_{3-7}$)cycloalkyl-(C$_{1-4}$)alkyl-; wherein each of the (C$_{1-6}$)alkyl, (C$_{3-7}$)cycloalkyl and (C$_{3-7}$)cycloalkyl-(C$_{1-4}$)alkyl- is optionally substituted with one or more substituents each independently selected from —OH, halo, —COON, —COO(C$_{1-6}$)alkyl, (C$_{1-6}$)alkyl, —O—(C$_{1-6}$)alkyl, —NH$_2$, —NH(C$_{1-4}$)alkyl and —N((C$_{1-4}$)alkyl)$_2$; or the groups $R^{11}$ and $R^{12}$ may be covalently bonded together along with the N to which they are attached to form a 5-, 6- or 7-membered saturated, unsaturated or aromatic N-containing heterocycle or a 8-, 9-, 10- or 11-membered saturated, unsaturated or aromatic N-containing bicyclic heteropolycycle, each of the heterocycle and heteropolycycle optionally containing from 1 to 3 additional heteroatoms each independently selected from O, N, and S and each of the heterocycle and heteropolycycle being optionally substituted with $R^{15}$;

wherein $R^{15}$ is one to three substituents each independently selected from fluorine, chlorine, bromine, methyl, ethyl, propyl, —COOH, —COO(C$_{1-3}$)alkyl, —CONH$_2$, —CONH(C$_{1-3}$)alkyl, —CON((C$_{1-3}$)alkyl)$_2$, —OH, —NH$_2$, —NH(C$_{1-3}$)alkyl, —N((C$_{1-3}$)alkyl)$_2$, —O—(C$_{1-3}$)alkyl, nitro, cyano, azido, phenyl, phenylmethyl,

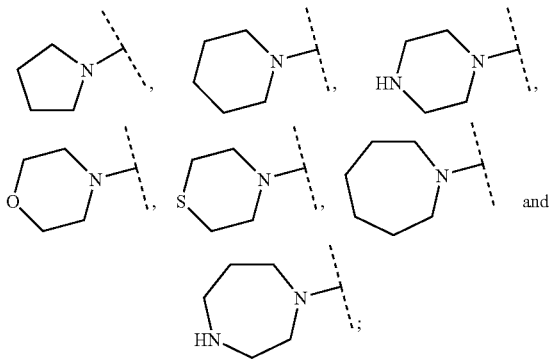

wherein each of the methyl, ethyl and propyl are optionally substituted with —OH, —O—(C$_{1-3}$)alkyl, —COOH, —COO(C$_{1-3}$)alkyl, —CONH$_2$, —CONH(C$_{1-3}$)alkyl, —CON((C$_{1-3}$)alkyl)$_2$, —NH$_2$, —NH(C$_{1-3}$)alkyl or —N((C$_{1-3}$)alkyl)$_2$; and wherein each of the

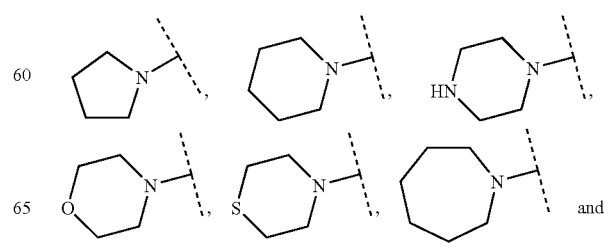

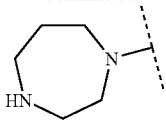
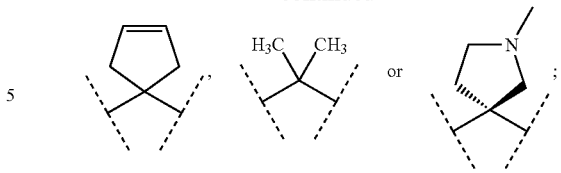

are optionally substituted with $(C_{1-3})$alkyl;

$R^2$ is H, $(C_{1-6})$alkyl, $(C_{2-6})$alkenyl, $(C_{3-7})$cycloalkyl, aryl or Het, wherein Het is a 5- or 6-membered aromatic heterocycle having 1 to 4 heteroatoms each independently selected from O, N and S; the aryl and Het being optionally substituted with $R^{21}$ wherein $R^{21}$ is one, two or three substituents each independently selected from $(C_{1-3})$alkyl, $(C_{1-3})$haloalkyl, $(C_{3-6})$cycloalkyl, —CN, —NH$_2$, —NH$(C_{1-3})$alkyl, —N$((C_{1-3})$alkyl$)_2$, halo, —O—$(C_{1-3})$alkyl, —S—$(C_{1-3})$alkyl, —S—$(C_{1-3})$haloalkyl, —SO—$(C_{1-3})$alkyl, SO—$(C_{1-3})$haloalkyl, —SO$_2$—$(C_{1-3})$alkyl and —SO$_2$—$(C_{1-3})$haloalkyl;

$R^3$ is cyclopentyl or cyclohexyl, each being optionally substituted with one or two fluoro substituents;

$R^4$ and $R^5$ are each independently selected from $(C_{1-3})$alkyl; or $R^4$ and $R^5$ are covalently bonded together along with the carbon atom to which they are attached to form $(C_{3-6})$cycloalkyl, $(C_{5-6})$cycloalkenyl or a 5- or 6-membered saturated or unsaturated heterocycle having 1 or 2 heteroatoms each independently selected from O and N; wherein the $(C_{3-6})$cycloalkyl, $(C_{5-6})$cycloalkenyl and 5- or 6-membered heterocycle are each optionally substituted with $(C_{1-4})$alkyl;

$R^6$ is H, methyl or ethyl;

D is selected from O, S and NR$^7$;

E is selected from O, S and NR$^8$;

$R^7$ is H or $(C_{1-6})$alkyl;

$R^8$ is H or $(C_{1-6})$alkyl; and $R^9$ is COOH, CONH$_2$, or CONH$(C_{1-6})$alkyl.

More preferably, $R^1$ is methyl;

$R^2$ is phenyl or Het, wherein Het is selected from

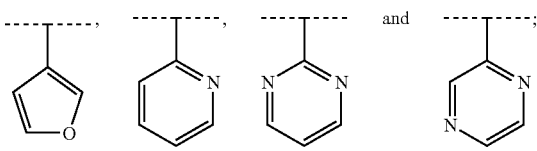

and wherein the phenyl and Het are unsubstituted or substituted with $R^{21}$, wherein $R^{21}$ is one or two substituents each independently selected from methoxy, fluoro, chloro and bromo;

$R^3$ is cyclopentyl, cyclohexyl or 4,4-difluorocyclohexyl;

the group

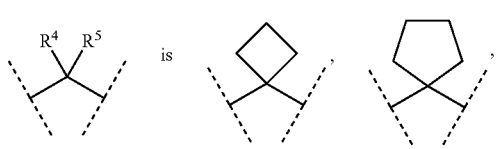

$R^6$ is H or methyl;

$R^7$ is H or methyl;

$R^8$ is H or methyl; and $R^9$ is COOH, CONH$_2$, or CONHCH$_3$.

Included within the scope of this invention is each single compound of formula (I) as presented in Tables 1 to 5.

In general, all tautomeric and isomeric forms and mixtures thereof, for example, individual geometric isomers, stereoisomers, enantiomers, diastereomers, racemates, racemic or non-racemic mixtures of stereoisomers, mixtures of diastereomers, or mixtures of any of the foregoing forms of a chemical structure or compound is intended, unless the specific stereochemistry or isomeric form is specifically indicated in the compound name or structure.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the present invention from this disclosure and the knowledge in the art.

Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof.

These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

Pharmaceutical Composition

Compounds of the present invention may be administered to a mammal in need of treatment for hepatitis C viral infection as a pharmaceutical composition comprising a therapeutically effective amount of a compound according to the invention or a pharmaceutically acceptable salt or ester thereof; and one or more conventional non-toxic pharmaceutically-acceptable carriers, adjuvants or vehicles. The specific formulation of the composition is determined by the solubility and chemical nature of the compound, the chosen route of administration and standard pharmaceutical practice. The pharmaceutical composition according to the present invention may be administered orally or systemically.

For oral administration, the compound, or a pharmaceutically acceptable salt or ester thereof, can be formulated in any orally acceptable dosage form including but not limited to aqueous suspensions and solutions, capsules or tablets. For systemic administration, including but not limited to administration by subcutaneous, intracutaneous, intravenous, intramuscular, intra-articular, intrasynovial, intrasternal, intrathecal, and intralesional injection or infusion techniques, it is preferred to use a solution of the compound, or a pharmaceutically acceptable salt or ester thereof, in a pharmaceutically acceptable sterile aqueous vehicle.

Pharmaceutically acceptable carriers, adjuvants, vehicles, excipients and additives as well as methods of formulating pharmaceutical compositions for various modes of administration are well-known to those of skill in the art and are described in pharmaceutical texts such as Remington: The Science and Practice of Pharmacy, 21st Edition, Lippincott Williams & Wilkins, 2005; and L. V. Allen, N. G. Popovish and H. C. Ansel, Pharmaceutical Dosage Forms and Drug Delivery Systems, 8th ed., Lippincott Williams & Wilkins, 2004.

The dosage administered will vary depending upon known factors, including but not limited to the activity and pharmacodynamic characteristics of the specific compound employed and its mode, time and route of administration; the age, diet, gender, body weight and general health status of the recipient; the nature and extent of the symptoms; the severity and course of the infection; the kind of concurrent treatment; the frequency of treatment; the effect desired; and the judgment of the treating physician. In general, the compound is most desirably administered at a dosage level that will generally afford antivirally effective results without causing any harmful or deleterious side effects.

A daily dosage of active ingredient can be expected to be about 0.001 to about 1000 milligrams per kilogram of body weight, with the preferred dose being about 0.01 to about 50 mg/kg. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Combination Therapy

Combination therapy is contemplated wherein a compound according to the invention, or a pharmaceutically acceptable salt or ester thereof, is co-administered with at least one additional antiviral agent. The additional agents may be combined with compounds of this invention to create a single dosage form. Alternatively these additional agents may be separately administered, concurrently or sequentially, as part of a multiple dosage form.

When the pharmaceutical composition of this invention comprises a combination of a compound according to the invention, or a pharmaceutically acceptable salt or ester thereof, and one or more additional antiviral agent, both the compound and the additional agent should be present at dosage levels of between about 10 to 100%, and more preferably between about 10 and 80% of the dosage normally administered in a monotherapy regimen. In the case of a synergistic interaction between the compound of the invention and the additional antiviral agent or agents, the dosage of any or all of the active agents in the combination may be reduced compared to the dosage normally administered in a monotherapy regimen.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, $\alpha$-, $\beta$-, $\delta$-, $\omega$-, and $\tau$-interferons, while examples of class II interferons include, but are not limited to, $\gamma$-interferons.

Inhibitors of HCV NS3 protease include agents (compounds or biologicals) that are effective to inhibit the function of HCV NS3 protease in a mammal. Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700 and WO 2006/007708 (all by Boehringer Ingelheim), WO 02/060926, WO 03/053349, WO 03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune) and WO 2005/051980 (Schering), and the candidates identified as VX-950, ITMN-191 and SCH 503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 and WO 2006/007693 (all by Boehringer Ingelheim), WO 2005/049622 (Japan Tobacco), WO 2005/014543 (Japan Tobacco), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates XTL-2125, HCV 796, R-1626 and NM 283.

Inhibitors of another target in the HCV life cycle include agents (compounds or biologicals) that are effective to inhibit the formation and/or replication of HCV other than by inhibiting the function of the HCV NS3 protease. Such agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

HIV inhibitors include agents (compounds or biologicals) that are effective to inhibit the formation and/or replication of HIV. This includes but is not limited to agents that interfere with either host or viral mechanisms necessary for the formation and/or replication of HIV in a mammal. HIV inhibitors include, but are not limited to:
- NRTIs (nucleoside or nucleotide reverse transcriptase inhibitors; including but not limited to zidovudine, didanosine, zalcitabine, stavudine, lamivudine, emtricitabine, abacavir, and tenofovir);
- NNRTIs (non-nucleoside reverse transcriptase inhibitors; including but not limited to nevirapine, delavirdine, efavirenz, capravirine, etravirine, rilpivirine, GW695634 and BILR 355);
- protease inhibitors (including but not limited to ritonavir, tipranavir, saquinavir, nelfinavir, indinavir, amprenavir, fosamprenavir, atazanavir, lopinavir, VX-385 and TMC-114);
- entry inhibitors including but not limited to CCR5 antagonists (including but not limited to maraviroc (UK-427, 857), SCH-417690, GW873140 and TAK-652), CXCR4 antagonists (including but not limited to AMD-11070), fusion inhibitors (including but not limited to enfuvirtide (T-20)) and others (including but not limited to PRO-542 and BMS-488043);
- integrase inhibitors (including but not limited to c-1605, BMS-538158 and JTK-303);
- TAT inhibitors;
- maturation inhibitors (including but not limited to PA-457); and
- immunomodulating agents (including but not limited to levamisole).

HAV inhibitors include agents (compounds or biologicals) that are effective to inhibit the formation and/or replication of HAV. This includes but is not limited to agents that interfere with either host or viral mechanisms necessary for the formation and/or replication of HAV in a mammal. HAV inhibitors include but are not limited to Hepatitis A vaccines.

HBV inhibitors include agents (compounds or biologicals) that are effective to inhibit the formation and/or replication of HBV in a mammal. This includes but is not limited to agents that interfere with either host or viral mechanisms necessary for the formation and/or replication of HBV in a mammal. HBV inhibitors include, but are not limited to, agents that inhibit the HBV viral DNA polymerase and HBV vaccines.

Therefore, according to one embodiment, the pharmaceutical composition of this invention additionally comprises a therapeutically effective amount of one or more antiviral agents.

A further embodiment provides the pharmaceutical composition of this invention wherein the one or more antiviral agent comprises at least one other anti-HCV agent.

According to a more specific embodiment of the pharmaceutical composition of this invention, the at least one other anti-HCV agent comprises at least one immunomodulatory agent.

According to another more specific embodiment of the pharmaceutical composition of this invention, the at least one other anti-HCV agent comprises at least one other inhibitor of HCV polymerase.

According to yet another more specific embodiment of the pharmaceutical composition of this invention, the at least one other anti-HCV agent comprises at least one inhibitor of HCV NS3 protease.

According to still another more specific embodiment of the pharmaceutical composition of this invention, the at least one other anti-HCV agent comprises at least one inhibitor of another target in the HCV life cycle.

Methodology and Synthesis

The synthesis of compounds according to this invention is preferably accomplished following the general procedure outlined in Scheme 1 below.

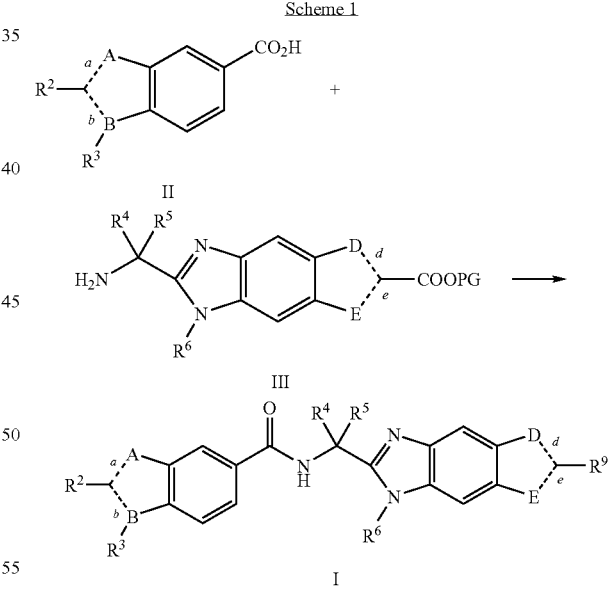

Compounds of formula I, wherein A, B, D, E, a, b, d, e, $R^2$, $R^3$, $R^4$, $R^5$, $R^6$ and $R^9$ are defined as hereinbefore, are preferably prepared by coupling carboxylic acids of general formula II with amines of general formula III, as illustrated in Scheme 1 above, using carboxyl-activating reagents well known by those skilled in the art. Such reagents include, but are not limited to, TBTU, HATU, BOP, BrOP, EDAC, DCC, isobutyl chloroformate and the like. Alternatively, carboxylic acids of general formula II may be converted to the corresponding acid chlorides using standard reagents, then coupled with amine derivatives of the general formula III. In the cases where —COOPG is an ester-protected carboxylic acid moiety, a saponification reaction is carried out (using protocols well known by those skilled in the art) to obtain the free carboxylic acid ($R^9$ is COOH). Alternatively, compounds of formula (I) wherein $R^9$ is other than COOH may be produced from the protected or unprotected carboxylic acid using well known procedures.

Intermediate carboxylic acids of formula II may be prepared by procedures described in WO 02/04425, WO 03/007945, WO 03/010140, WO 03/010141, WO 2004/064925 or WO 2004/065367, or by procedures described in the examples below.

Intermediate amines of formula III may be prepared according to the general procedures outlined in Scheme 2 below.

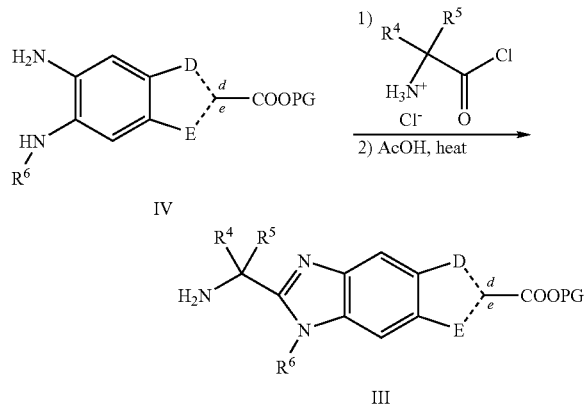

Scheme 2

IV

III

Amine intermediates of general formula III in Scheme 1 may be prepared from the corresponding diamine precursors of general formula IV by coupling with the appropriate α,α-disubstituted amino acid chloride hydrochlorides. Preparation of the appropriate α,α-disubstituted amino acid chloride hydrochlorides from the corresponding α,α-disubstituted amino acids may be carried out as described in WO 03/007945 or WO 03/010141, or by using the procedure, or an adaptation thereof, described by E. S. Uffelman et al. (*Org. Lett.* 1999, 1, 1157). The amide intermediate formed in the coupling reaction is then cyclized by heating with acetic acid, to provide amine intermediates of general formula III.

Preparation of the diamine precursors of general formula IV in Scheme 2 is preferably carried out by applying the procedures as outlined in the examples, including any adaptation of these procedures, and/or applying additional synthetic steps known to the person skilled in the art.

EXAMPLES

The present invention is illustrated in further detail by the following non-limiting examples. As is well known by a person skilled in the art, reactions are performed in a nitrogen or argon atmosphere where necessary to protect reaction components from air or moisture. Temperatures are given in degrees Celsius. Flash chromatography is performed on silica gel. Solution percentages or ratios express a volume to volume relationship, unless stated otherwise. Mass spectral analyses are recorded using electrospray mass spectrometry. Analytical HPLC was carried out under standard conditions using a Combiscreen ODS-AQ C18 reverse phase column, YMC, 50×4.6 mm i.d., 5 μM, 120 Å at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
|---|---|---|---|
| 0 | 3.0 | 95 | 5 |
| 0.5 | 3.0 | 95 | 5 |
| 6.0 | 3.0 | 50 | 50 |
| 10.5 | 3.5 | 0 | 100 |

Abbreviations or symbols used herein are included in the following:

| | |
|---|---|
| AcOH: | acetic acid; |
| $Ac_2O$: | acetic anhydride; |
| BOC or Boc: | tert-butyloxycarbonyl; |
| BOP: | benzotriazole-1-yloxy-tris(dimethylamino)phosphonium hexafluorophosphate; |
| BroP: | Bromo tris(dimethylamino)phosphonium hexafluorophosphate; |
| Bu: | butyl; |
| DAST: | (diethylamino)sulfur trifluoride; |
| DCC: | 1,3-Dicyclohexyl carbodiimide; |
| DCM: | dichloromethane; |
| DIBAL-H: | di-iso-butylaluminum hydride; |
| DME: | dimethoxyethane; |
| DMF: | N,N-dimethylformamide; |
| DMSO: | dimethylsulfoxide; |
| $EC_{50}$: | 50% effective concentration; |
| EDAC: | see EDC; |
| EDC: | 1-(3-dimethylaminopropyl)-3-ethyl carbodiimide hydrochloride; |
| $ES^-$: | electro spray (negative ionization); |
| $ES^+$.: | electro spray (positive ionization); |
| Et: | ethyl; |
| $Et_3N$: | triethylamine; |
| $Et_2O$: | diethyl ether; |
| EtOAc: | ethyl acetate; |
| EtOH: | ethanol; |
| HATU: | O-(7-azabenzotriazol-1-yl)-N,N,$N^l$,$N^l$-tetramethyluronium hexafluorophosphate; |
| HBTU: | O-Benzotriazol-1-yl-N,N,N',N'-tetramethyluronium hexafluorophosphate; |
| HOAT: | 1-hydroxy-7-azabenzotriazole; |
| HOBt: | 1-Hydroxybenzotriazole; |
| HPLC: | high performance liquid chromatography; |
| $^iPr$ or i-Pr: | iso-propyl; |
| Me: | methyl; |
| MeCN: | acetonitrile; |
| MeI: | iodomethane; |
| MeOH: | methanol; |
| MS (ES): | electrospray mass spectrometry; |
| NMP: | N-methyl-2-pyrrolidinone; |
| NMR: | nuclear magnetic resonance spectroscopy; |
| Ph: | phenyl; |
| PG: | protecting group; |
| Pr: | propyl; |
| RT: | room temperature (approximately 25° C.); |
| TBME: | tert-butylmethyl ether; |
| TBTU: | 2(1H-benzotriazol-1-yl)-N,N,N',N'-tetramethyluronium tetrafluoroborate; |
| tBu: | tert.-butyl; |
| Tf: | trifluoromethylsulfonyl; |
| TfO: | trifluoromethylsulfonate; |
| TFA: | trifluoroacetic acid; |
| THF: | tetrahydrofuran; |
| TLC: | thin layer chromatography; |
| TMS: | trimethylsilyl; |

Example 1

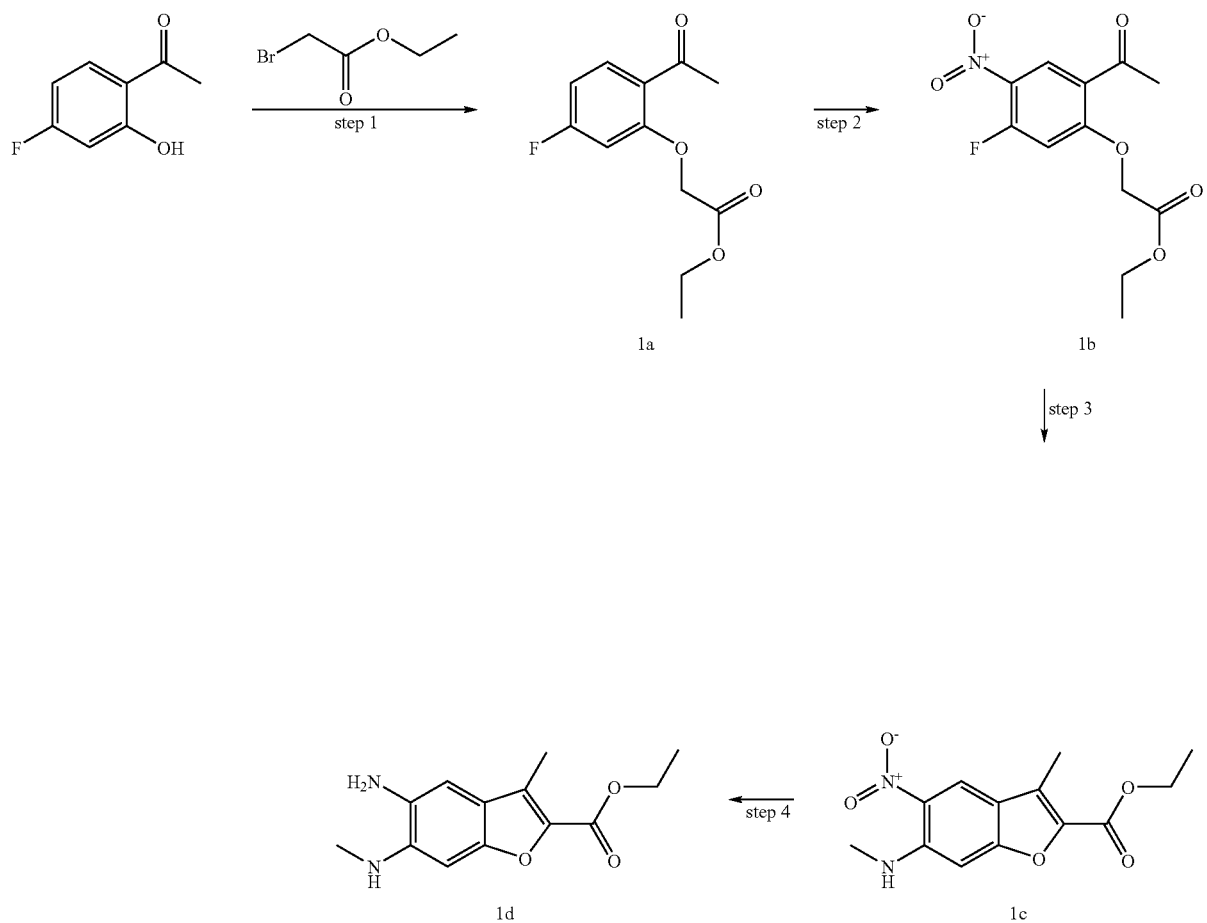

Step 1:

To a solution of 4-fluoro-2-hydroxyacetophenone (1.0 g, 6.5 mmol) and ethyl bromoacetate (0.80 mL, 7.2 mmol) in DMF (10.0 mL), was added potassium carbonate (2.7 g, 19.5 mmol). The mixture was heated to 60° C. for 2 h, then cooled to RT, diluted with EtOAc (40 mL) and quenched with $H_2O$ (15 mL). The two layers were separated, and the organic layer was washed twice with water, once with brine, dried over $MgSO_4$, filtered and concentrated. The compound was purified by flash column chromatography on silica gel using a solvent gradient of EtOAc in hexane (from 0% to 20%) to provide compound 1a (1.4 g, 90% yield).

Step 2:

To a solution of compound 1a (0.5 g, 2.1 mmol) in 2 mL of concentrated $H_2SO_4$ at −5° C., was added a solution of nitric acid (0.23 mL) in $H_2SO_4$ (0.5 mL). After 10 minutes, the mixture was poured onto ice, and the slurry was extracted with $CH_2Cl_2$ (3×15 mL). The organic layers were combined, washed with saturated $NaHCO_3$(aq) and brine, dried over $MgSO_4$, filtered and concentrated. Compound 1b was used in the next step without purification (0.49 g, 83% yield).

Step 3:

To a solution of compound 1b (0.32 g, 1.1 mmol) in $CH_3CN$ (5 mL), was added $Et_3N$ (0.30 mL, 2.2 mmol) and $MeNH_2$ (2.0 M in THF, 1.00 mL, 2.0 mmol). The reaction mixture was stirred at RT for 1.5 h, then was concentrated under vacuum. The crude material was dissolved in DMF (5 mL), and cesium carbonate (1.4 g, 4.3 mmol) was added. The mixture was stirred at 65° C. for 18 h, then was diluted with EtOAc (25 mL), and quenched with saturated $NH_4Cl$ (aq) (15 mL). The layers were separated, and the aqueous layer was extracted twice with EtOAc. The organic layers were combined, washed with brine, dried over $MgSO_4$, filtered and concentrated. The crude material was purified by flash column chromatography on silica gel using a solvent gradient of EtOAc in hexanes (from 10% to 25%) to give compound 1c (0.12 g, 39% yield).

Step 4:

To a suspension of compound 1c (0.08 g, 0.3 mmol) in EtOH/EtOAc/THF (5 mL/0.50 mL/0.50 mL), was added $Pd(OH)_2$ (20% on carbon, 0.01 g). The reaction mixture was stirred under an $H_2$ atmosphere for 18 h, then filtered through Celite™ (the solid was washed with EtOAc) and the filtrate was concentrated under vacuum to give compound 1d (0.054 g, 75% yield).

Example 2

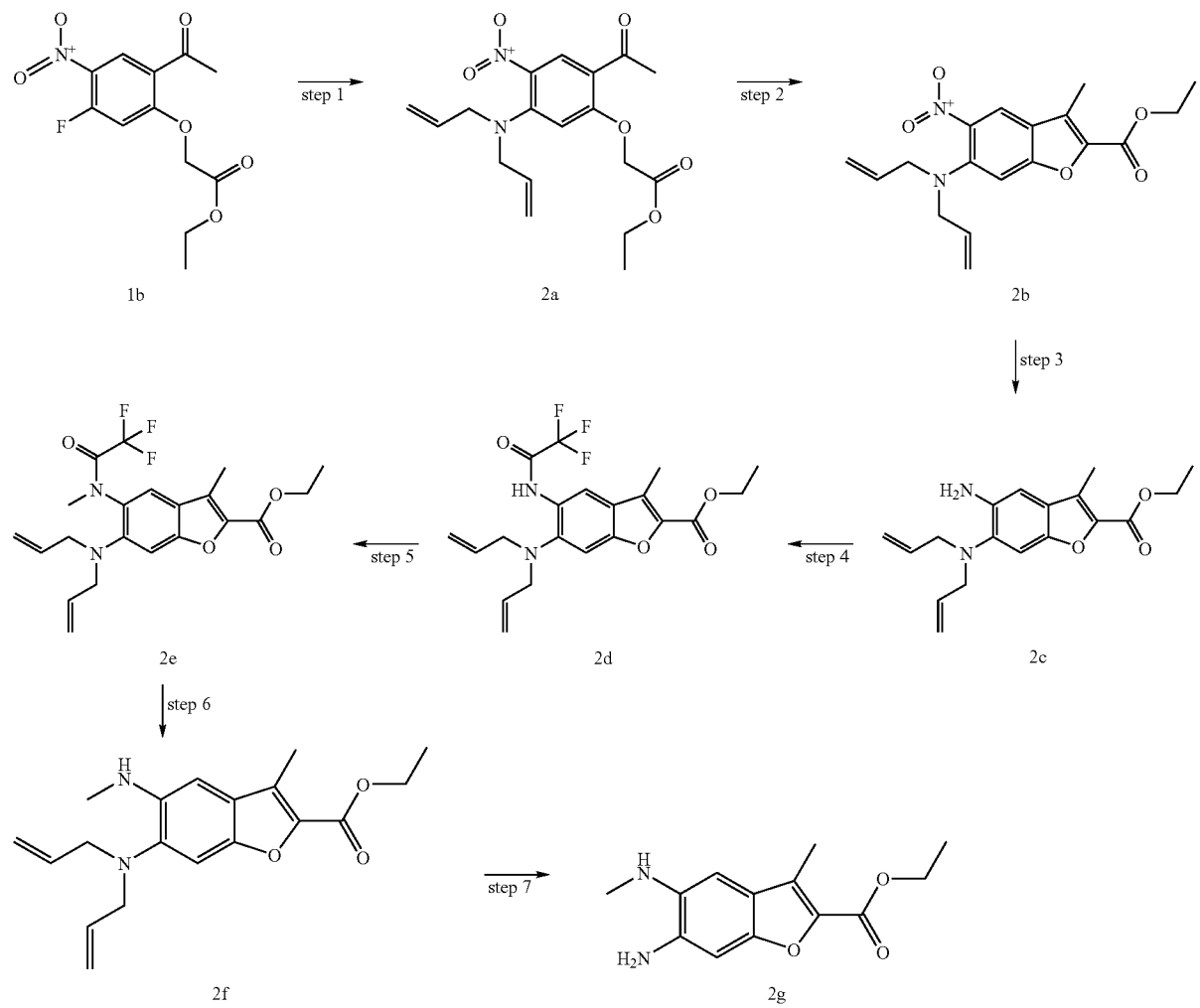

Step 1:
  To a solution of compound 1b (Example 1, step 2) (2.0 g, 7.0 mmol) in CH$_3$CN (30 mL), was added Et$_3$N (1.9 mL, 13.5 mmol) and diallylamine (1.6 mL, 12.6 mmol). The reaction mixture was stirred at RT for 1.5 h, and then concentrated under vacuum. The residue was diluted with EtOAc (40 mL), washed with saturated aqueous NaHCO$_3$ (40 mL), dried over MgSO$_4$, filtered and concentrated. The crude material 2a (2.5 g, ~100%) was used in the next step without purification.

Step 2:
  To a solution of compound 2a (2.4 g, 6.7 mmol) in DMF (40 mL), was added cesium carbonate (2.6 g, 8.0 mmol). The reaction mixture was stirred at 50° C. for 18 h, then cooled to RT, diluted with EtOAc (60 mL) and quenched with saturated NH$_4$Cl (aq). The layers were separated, and the aqueous layer was extracted twice with EtOAc. The organic layers were then combined, washed with NH$_4$Cl, water (twice) and brine, dried over MgSO$_4$, filtered and concentrated. The crude material 2b (1.4 g, 59% yield) was used in the next step without any purification.

Step 3:
  To a solution of compound 2b (1.35 g, 3.9 mmol) in ethanol (40 mL), was added tin chloride dihydrate (2.2 g, 9.8 mmol). The reaction mixture was heated to 65° C. for 2 h, then cooled to RT and poured into ice/water. The reaction was quenched with NaHCO$_3$, and the mixture was extracted with EtOAc (3×). The organic layers were combined, washed with brine, dried over MgSO$_4$, filtered and concentrated. The crude material 2c (0.85 g, 69% yield) was used in the next step without any purification.

Step 4:
  To a solution of compound 2c (0.85 g, 2.7 mmol) in CH$_2$Cl$_2$ (15 mL) at 0° C. was added trifluoroacetic anhydride (0.42 mL, 3.0 mmol). The reaction mixture was stirred at 0° C. for 20 min, then diluted with EtOAc (40 mL) and quenched with water and with saturated NaHCO$_3$ (aq). The layers were separated, and the aqueous layer was extracted twice with EtOAc. The organic layers were then combined, washed with brine, dried over MgSO$_4$, filtered and concentrated. The crude material 2d (0.98 g, 89% yield) was used in the next step without any purification.

Step 5:
  To a solution of compound 2d (0.10 g, 0.24 mmol) in acetone (5 mL), was added K$_2$CO$_3$ (0.082 g, 0.59 mmol) and MeI (0.020 mL, 0.32 mmol). The reaction mixture was stirred at RT for 6 h, then diluted with EtOAc (50 mL), filtered through Celite™ and concentrated. The crude material 2e (0.10 g) was used in the next step without any purification.

Step 6:

To a solution of compound 2e (0.10 g, 0.24 mmol) in MeOH (5 mL), was added NaBH$_4$ (pellets, 0.027 g, 0.73 mmol) in one portion. The reaction mixture was stirred for 1 h, then diluted with EtOAc (40 mL) and quenched with water. Brine was added to the mixture and the layers were separated. The aqueous layer was extracted once with EtOAc and the organic layers were combined, washed twice with brine, dried over MgSO$_4$, filtered and concentrated. The residue was purified by flash column chromatography on silica gel using a solvent gradient of EtOAc in hexanes (from 0% to 10%) to give compound 2f (0.062 g, 78% yield) as a yellow oil.

Step 7:

To a degassed solution of compound 2f (0.062 g, 0.19 mmol) in THF (3 mL), was added poly(methylhydrosiloxane) (0.060 g), tetrakis(triphenylphosphine)palladium (0.219 g, 0.189 mmol) and zinc chloride (0.103 g, 0.756 mmol). The reaction mixture was stirred at RT for 4 h, then diluted with EtOAc (40 mL) and washed with saturated NaHCO$_3$ (aq). The aqueous layer was extracted twice with EtOAc and the organic layers were combined, washed with brine, dried over MgSO$_4$, filtered and concentrated. The residue was purified by flash column chromatography on silica gel using a solvent gradient of EtOAc in hexanes (from 10% to 100%) to give compound 2g (0.026 g, 55% yield).

Example 3

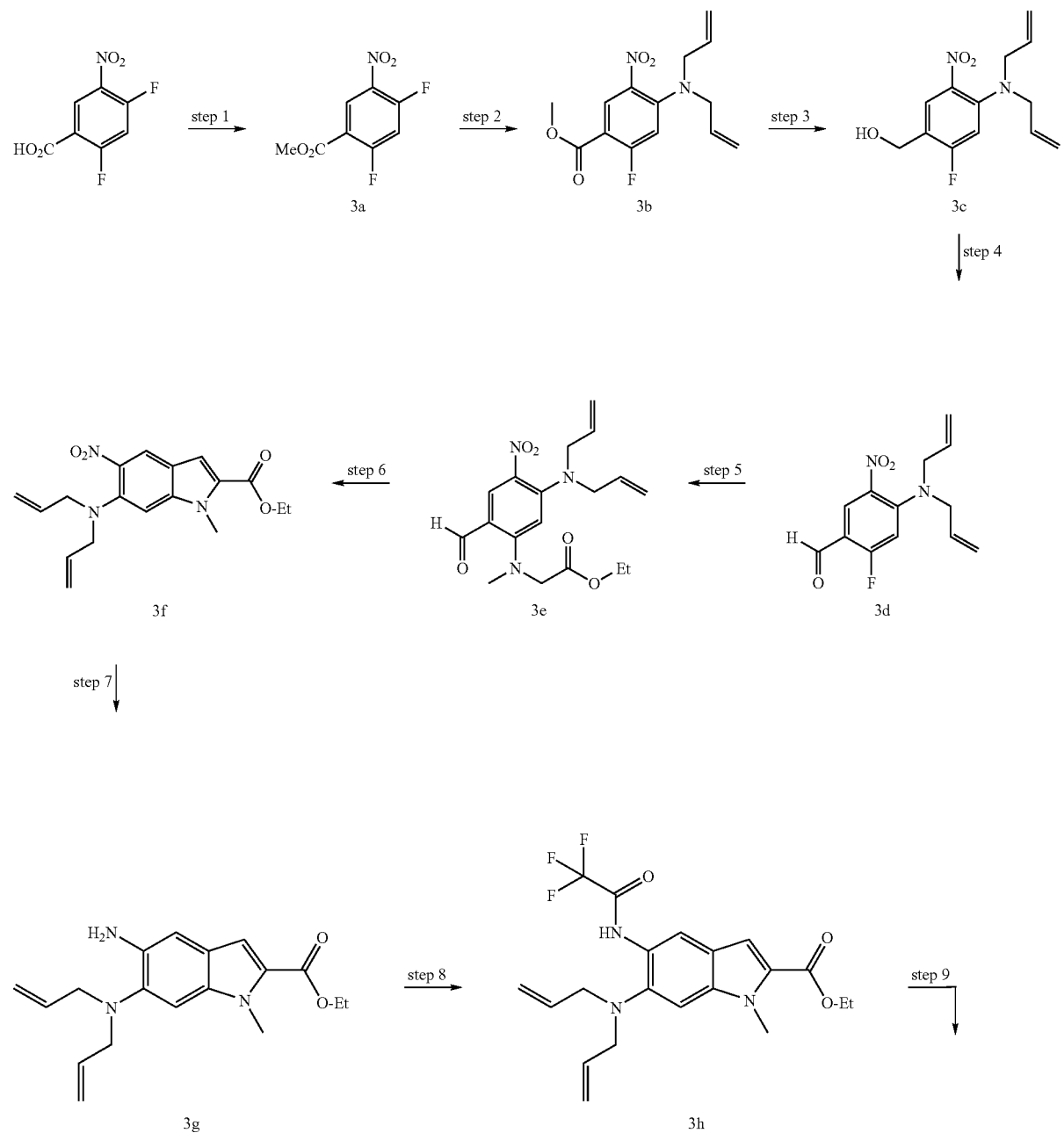

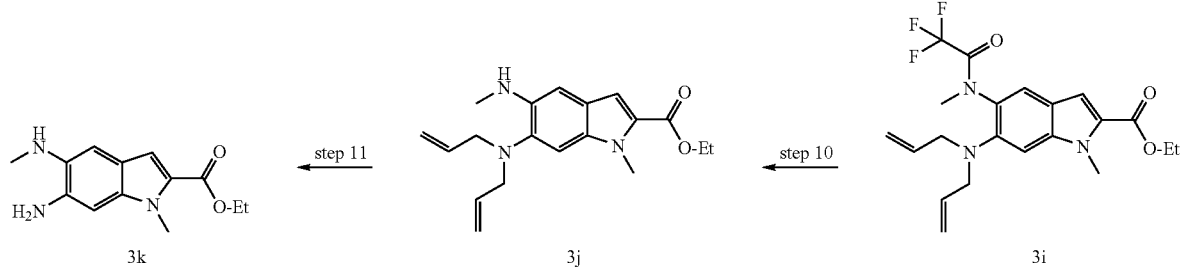

-continued

Step 1:

To a solution of 2,4-difluoro-5-nitrobenzoic acid (4.96 g, 24.4 mmol, 1 eq) in MeOH (100 mL), was added a solution of 4N HCl in 1,4-dioxane (9 mL). The reaction mixture was heated to reflux for 16 h, then cooled to RT and the MeOH was evaporated under vacuum. The residue was dissolved in EtOAc (50 mL) and the organic phase was washed with aqueous saturated NaHCO$_3$ (25 mL) and brine (25 mL), then dried over MgSO$_4$, filtered and concentrated. A quantitative yield of the ester 3a was obtained as a yellow solid (5.30 g, 24.4 mmol).

Step 2:

A solution of ester 3a (3.0 g, 14 mmol) in THF (53 mL) was cooled in an ice bath, and triethylamine (3.85 mL, 27.6 mmol, 2 eq) and diallyl amine (2.4 mL, 19 mmol, 1.4 eq) were added. The reaction mixture was allowed to stir for 2 h, then was diluted with EtOAc (75 mL) and washed with HCl (0.1N, 50 mL), saturated aqueous NaHCO$_3$ (50 mL) and brine (50 mL). The combined organic phase was dried over MgSO$_4$, filtered, and concentrated under reduced pressure to give compound 3b (4.00 g) as a yellow oil, in a mixture with the bis allyl amine adduct (<10% of side product). The mixture was used in the subsequent reaction.

Step 3:

To a cooled (−78° C.) solution of compound 3b (4.00 g, 13.6 mmol, 1 eq) in THF (45 mL), was added DIBAL-H (1M solution in CH$_2$Cl$_2$, 32.6 mL, 2.4 eq). The reaction mixture was allowed to stir at −78° C. for 1 h, then at 0° C. for 30 min. A solution of 1N HCl (20 mL), cooled to 0° C., was added to the reaction mixture very slowly with stirring. The solution was warmed to RT and extracted with EtOAc (3×50 mL). The combined organic layers were washed with brine (50 mL), dried over MgSO$_4$, filtered and concentrated. Purification of the crude product by flash chromatography using 20% EtOAc in hexanes afforded the alcohol 3c (3.30 g, 12.4 mmol, 91% yield) as a bright yellow oil.

Step 4:

To a cooled (0° C.) solution of compound 3c (2.35 g, 8.83 mmol, 1 eq) in CH$_2$Cl$_2$ (50 mL), was added Dess-Martin reagent (4.12 g, 9.7 mmol, 1.1 eq) portion wise. The reaction mixture was allowed to warm to RT over the course of 1 h, then a mixture of NaHCO$_3$/Na$_2$S$_2$O$_3$ (0.5 M, 1:1 ratio, 30 mL) was added and stirring was continued for 1 h. The product was extracted with CH$_2$Cl$_2$ (3×30 mL) and the combined organic extracts were then washed with a 1:1 mixture of water and saturated aqueous NaHCO$_3$ (30 mL), dried over MgSO$_4$, filtered and concentrated. The crude residue was purified by flash chromatography (10% EtOAc in hexanes) to provide aldehyde 3d (2.00 g, 7.57 mmol, 86% yield) as a yellow solid.

Step 5:

To a solution of compound 3d (2.00 g, 7.57 mmol, 1 eq) in DMSO (25 mL), was added triethylamine (2.64 mL, 18.9 mmol, 2.5 eq) and sarcosine ethyl ester hydrochloride (1.51 g, 9.84 mmol, 1.3 eq). The reaction mixture was stirred at ambient temperature for 72 h and the reaction was quenched by the addition of 0.1N HCl and the mixture was acidified to pH 3. The product was extracted with EtOAc (3×40 mL) and the combined organic layers were washed with brine (50 mL), dried over MgSO$_4$, filtered and concentrated. The product was purified by flash chromatography using a gradient of EtOAc in hexanes (from 10% to 100%) to provide compound 3e (1.40 g, 3.87 mmol, 51% yield).

It will be apparent to those skilled in the art that the analogous methyl ester can be made by replacing the sarcosine ethyl ester hydrochloride in this step with sarcosine methyl ester hydrochloride.

Step 6:

To a solution of compound 3e (636 mg, 1.76 mmol, 1.0 eq) in ethanol (20 mL), was added sodium ethoxide (21 wt % in ethanol, 0.741 mL, 1.3 eq). The mixture was stirred at RT for 15 min, then concentrated under vacuum and diluted with water (20 mL), and the product was extracted with EtOAc (3×20 mL). The combined organic layers were washed with water (20 mL) and brine (20 mL), dried over MgSO$_4$, filtered and concentrated. The crude material was purified by flash chromatography using a gradient of EtOAc in hexanes (from 15% to 50%). The desired product 3f (465 mg, 1.35 mmol, 77% yield) was obtained as an orange solid.

Step 7:

Intermediate 3f (742 mg, 2.16 mmol, 1.0 eq) was placed in a sealed tube and dissolved in ethanol (15 mL). To this solution was added tin chloride dihydrate (2.04 g, 98%, 8.86 mmol, 4.1 eq), and the tube was sealed and heated to 70° C. for 16 h. After cooling, the reaction mixture was added slowly to a vigorously stirred solution of saturated aqueous NaHCO$_3$ (50 mL). The resulting mixture was filtered through a Büchner funnel, the filtrate was extracted with EtOAc (3×) and the combined organic layers were washed with saturated aqueous NaHCO$_3$ (30 mL) and brine (30 mL). The combined organic extracts were dried over MgSO$_4$, filtered and concentrated. The residue was purified by flash chromatography using 10% EtOAc in hexanes as eluent to give aniline 3g (480 mg, 1.53 mmol, 71% yield) as a thick yellow oil.

Step 8:

A solution of compound 3g (480 mg, 1.53 mmol, 1 eq) in CH$_2$Cl$_2$ was cooled to 0° C. and trifluoroacetic anhydride (0.238 mL, 1.69 mmol, 1.1 eq) was added. The reaction mixture was stirred at 0° C. for 20 min, then was diluted with water (15 mL) and the product was extracted with EtOAc (3×15 mL). The combined organic layers were washed with saturated aqueous NaHCO$_3$ (20 mL) and brine (20 mL) and the organic phase was dried over MgSO$_4$, filtered and concentrated. The crude reaction mixture was purified by flash chromatography using a solvent gradient of from 5% to 10% EtOAc/hexanes to give intermediate 3h (590 mg, 1.44 mmol, 94% yield) as a yellow solid.

Step 9:
To a cooled solution (0° C.) of compound 3h (590 mg, 1.44 mmol, 1.0 eq) in DMF (9.0 mL), NaH (60% dispersion in mineral oil, 63.4 mg, 1.59 mmol, 1.1 eq) was added. The reaction mixture was stirred at 0° C. for 10 minutes, then at RT for an additional 15 minutes, then was re-cooled to 0° C. and MeI (90 μL, 1.44 mmol, 1 eq) was added. The reaction mixture was allowed to slowly warm to RT and the reaction was quenched by the addition of methanol (0.500 mL) after 90 minutes. The mixture was diluted with EtOAc (15 mL) and washed with NaHCO₃ (20 mL) and the product was extracted with EtOAc (3×15 mL). The combined organics were washed with brine (20 mL), dried over MgSO₄ and filtered and concentrated. Purification of the residue by flash chromatography using a gradient of from 5% to 10% EtOAc in hexanes, afforded compound 3i (600 mg, 1.42 mmol, 98% yield) as a clear pale yellow oil.
Step 10:

mmol, 1.4 eq), polymethylhydrosiloxane (400 mg) and palladium tetrakis triphenyl phosphine (136 mg, 0.118 mmol, 0.1 eq) were added. The mixture was again degassed under argon and allowed to stir at RT for an additional 16 h. The mixture was then diluted with EtOAc (15 mL), water (15 mL), and saturated aqueous NaHCO₃ (15 mL). The product was extracted with EtOAc (3×10 mL) and the extract was washed with water (15 mL) and brine (15 mL). The combined organic layers were dried over MgSO₄, filtered and concentrated. Purification by flash chromatography using a solvent gradient of EtOAc in hexanes (from 40% to 50% EtOAc) afforded compound 3k (190 mg, 0.768 mmol, 68% yield) as a brown solid.

Example 4

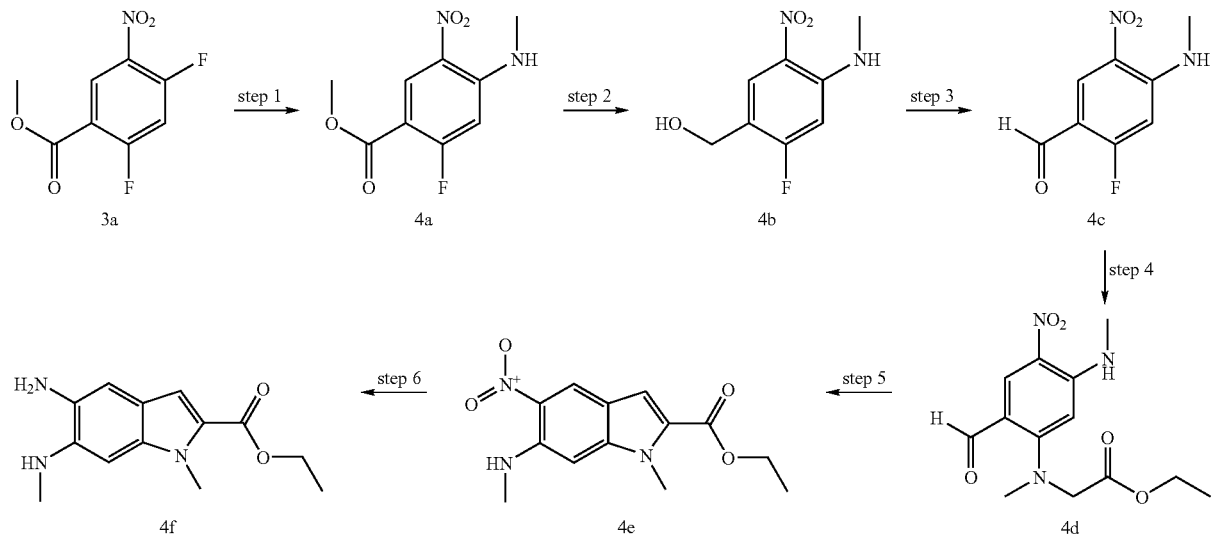

To a stirred solution of indole 3i (618 mg, 1.46 mmol, 1 eq) in dry MeOH (10 mL), was added NaBH₄ pellets (271 mg, 7.328 mmol, 5 eq) portion-wise. When evolution of gas had ceased, the mixture was stirred for a further 30 minutes (total reaction time of 1 h). The reaction mixture was concentrated under reduced pressure, diluted with water (20 mL) and extracted with EtOAc (3×20 mL). The combined organic layers were washed with brine (20 mL), dried over MgSO₄, filtered and concentrated. The crude product was purified by flash chromatography using 10% EtOAc in hexanes to yield compound 3j (375 mg, 1.15 mmol, 78% yield) as a sticky oil, which was used immediately in the next step.
Step 11:
The indole intermediate 3j (370 mg, 1.13 mmol, 1 eq), ZnCl₂ (209 mg, 1.54 mmol, 1.4 eq), polymethylhydrosiloxane (400 mg) and palladium tetrakis triphenyl phosphine (136 mg, 0.118 mmol, 0.1 eq) were dissolved in THF (15 mL) and the mixture was degassed under a stream of argon for 15 min and allowed to stir at RT for 72 h. The crude reaction mixture was diluted with water and the product was extracted with EtOAc (3×). The combined organic layers were washed with saturated aqueous NaHCO₃ and brine and the organic phase was dried over MgSO₄, filtered and concentrated. The residue was redissolved in THF (15 mL) and ZnCl₂ (209 mg, 1.54

Step 1:
To a cooled solution (0° C.) of ester 3a (Example 3, step 1) (1.63 g, 7.52 mmol, 1 eq.) in THF (7 mL), was added triethylamine (1.05 mL, 7.52 mmol, 1 eq.) and a solution of methylamine in THF (2N, 5.65 mL, 11.2 mmol, 1.5 eq.). The reaction mixture was allowed to stir for 1 h at 0° C., then was diluted with EtOAc (100 mL), and washed with H₂O (40 mL) and brine. The organic phase was dried over MgSO₄ and concentrated. The crude material 4a (1.70 g, 99% yield) was used in the next step without purification.
Step 2:
The methyl ester 4a was reduced to alcohol 4b using DIBAL-H in dichloromethane using the method described in Example 3, step 3.
Step 3:
Alcohol 4b was oxidized to the corresponding aldehyde 4c using Dess-Martin periodinane in dichloromethane using the method described in Example 3, step 4.
Step 4:
To a solution of 4c (524 mg, 2.64 mmol, 1 eq.) in DMSO (13 mL) were added sarcosine ethyl ester hydrochloride (609 mg, 3.96 mmol, 1.5 eq.) and Et₃N (921 μL, 2.5 eq). The reaction mixture was stirred at 80° C. for 1 h, more sarcosine (203 mg, 1.32 mmol, 0.5 eq) was added, and the reaction mixture was stirred for an additional hour at 80° C. The solution was diluted with EtOAc (100 mL), and washed with aqueous saturated NaHCO₃ (30 mL) and brine. The organic phase was dried over MgSO₄ and concentrated. The crude material was purified by flash chromatography using 50% EtOAc in hexanes to afford 578 mg (74% yield) of the desired aniline 4d.

Step 5:

The aniline 4d was converted to the corresponding indole 4e using sodium ethoxide in ethanol as described in Example 3, step 6.

Step 6:

The nitro derivative 4e was reduced to the corresponding aniline 4f using tin chloride di-hydrate in ethanol as described in Example 3, step 7.

Example 5

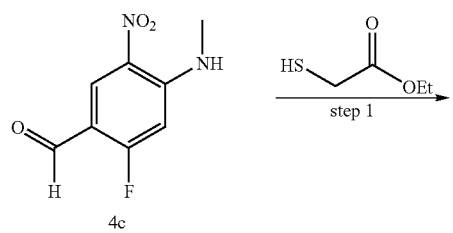

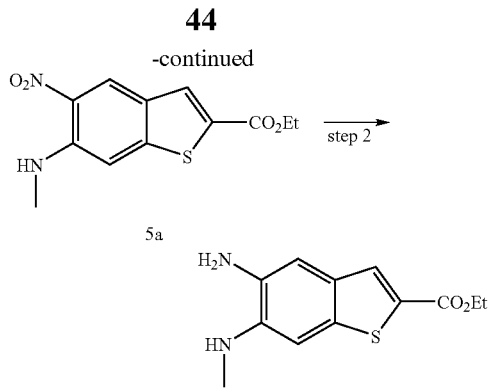

Step 1:

Compound 4c (Example 4, step 3) (200 mg, ~1 mmol)) was dissolved in DMSO (5 mL), Et₃N (281 µL, 2 mmol) and ethyl-2-mercaptoacetate (122 µL, 1.1 mmol) was added. The reaction mixture was stirred at RT for 48 h, then was diluted with EtOAc (100 mL) and the organic layer was washed with H₂O (2×25 mL) and brine, dried (MgSO₄) and concentrated. The residue was purified by flash column chromatography (5% to 10% EtOAc in hexane) to give the pure derivative 5a as a reddish-brown solid. (239 mg).

Step 2:

The nitro derivative 5a was reduced to the corresponding aniline 5b using SnCl₂-2H₂O in ethanol as described in Example 2, step 3.

Example 6

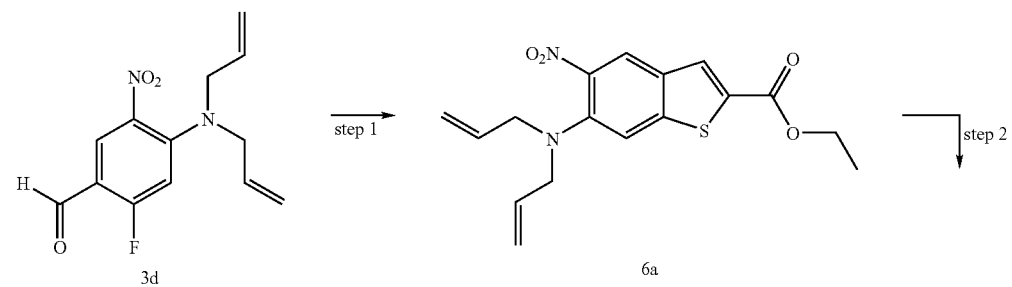

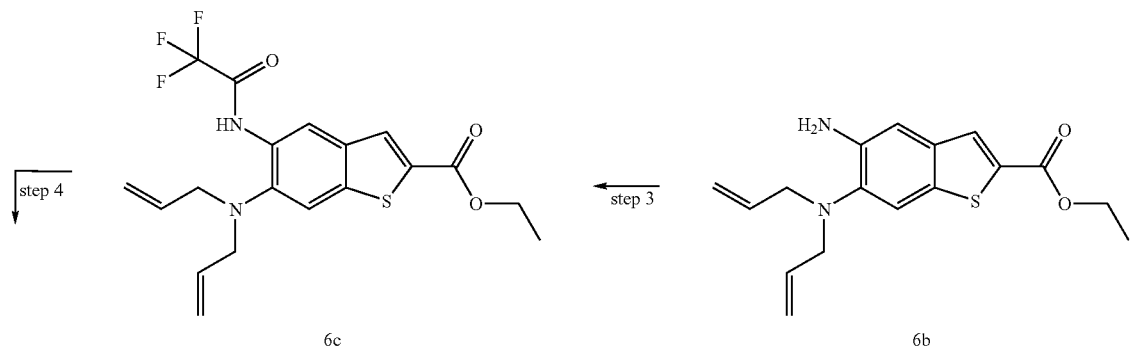

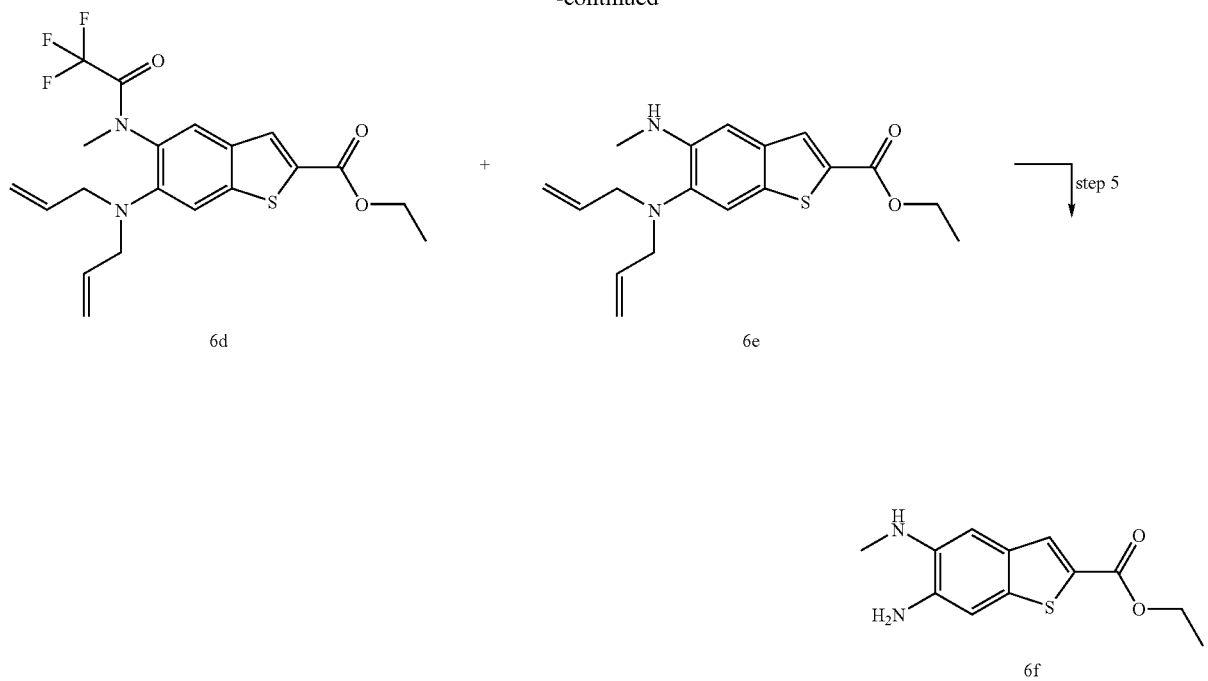

Step 1:

Conversion of the fluoro aldehyde derivative 3d (Example 3, step 4) to the thiophene 6a was achieved using the method described in Example 5, step 1.

Step 2:

The nitro derivative 6a was reduced to the corresponding aniline 6b using $SnCl_2 \cdot 2H_2O$ in ethanol as described in Example 2, step 3.

Step 3:

The aniline derivative 6b was converted to the corresponding trifluoroacetate analog 6c using trifluoroacetic anhydride in $CH_2Cl_2$ as described in Example 3, step 8.

Step 4:

To a cooled (0° C.) solution of the crude trifluoroacetate derivative 6c (2.28 g, ~5.5 mmol, 1 eq) in DMF (30 mL) was added NaH (60% disp. in mineral oil, 265 mg, 6.63 mmol, 1.2 eq). The reaction mixture was stirred at 0° C. for 10 min then warmed to RT for 15 min and again cooled to 0° C. MeI (516 μL, 8.29 mmol, 1.5 eq) was added and the solution was stirred 6 h at RT; more NaH (60% disp. in mineral oil, 265 mg, 6.63 mmol, 1.2 eq) was added after 2 h and 4 h of reaction. Water (15 mL) was added and the reaction mixture was diluted with EtOAc (200 mL). The organic phase was washed with $NaHCO_3$ and brine, then dried ($MgSO_4$) and concentrated. The crude material was purified using flash chromatography using a gradient of 5% to 20% of AcOEt in hexanes to afford compound 6d (1.91 g, 81% yield) and some of the deprotected analog 6e (363 mg, 19% yield). Derivative 6d was deprotected with $NaBH_4$ in MeOH using the procedure described in Example 3, step 10 and derivative 6e was used as such in the next step.

Step 5:

The di-allyl aniline 6e was deprotected to provide aniline 6f using polymethylhydrosiloxane, Pd tetrakis(triphenyl) phosphine and $ZnCl_2$ in THF as described in Example 3, step 11.

Example 7

Compound 7a was synthesized using the procedures of Example 4, steps 1-3, and Example 5, steps 1 and 2, except that in the procedure of Example 4, step 1, ammonia was used instead of methylamine.

Example 8

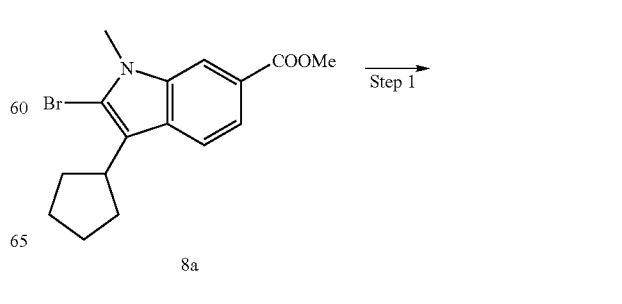

-continued

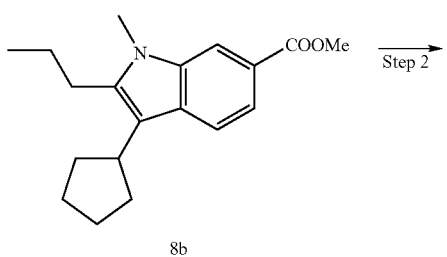

8b

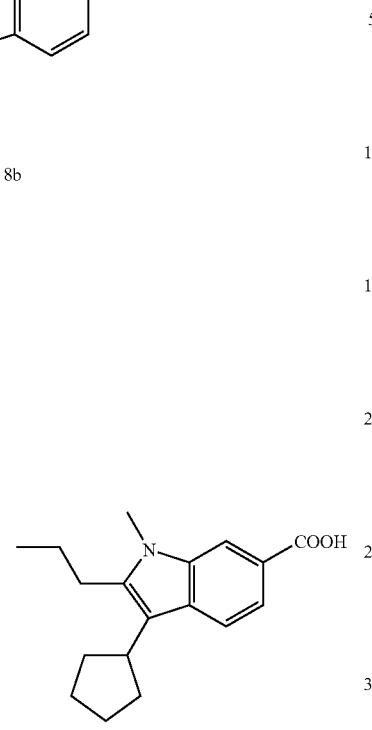

8c

Step 1:

The solution of the 2-bromoindole 8a (prepared as described in Example 12 of WO 03/010141) (2.51 g, 7.5 mmol) in anhydrous THF was cooled in a dry ice-acetone bath under argon and n-BuLi (2.5 M in hexane, 3.3 mL, 8.3 mmol) was added drop-wise, keeping the reaction temperature under −70° C. Upon completion of the addition, the mixture was stirred in the dry-ice bath for a further 15 minutes and 1-iodopropane (2.5 g, 15 mmol) was added drop-wise. The reaction mixture was allowed to warm to room temperature and stirred overnight, then was quenched with MeOH and diluted with 100 mL of ether and 50 mL of water. The organic layer was separated and washed with brine, then dried and concentrated. Column chromatography of the residue with 1% ethyl acetate in hexane gave 260 mg of compound 8b.

Step 2:

To a solution of compound 8b (260 mg, 0.86 mmol) in 1:1 THF/MeOH (10 mL) was added aqueous NaOH (5N, 0.9 mL, 4.3 mmol). The mixture was heated at 50° C. overnight, then cooled to room temperature and the solvents were evaporated. The residue was dissolved in 15 mL of water and washed twice with ether and once with hexane. The aqueous solution was acidified to pH 5 with acetic acid to give a white precipitate, which was filtered and dried under high vacuum to give compound 8c (180 mg).

Example 9

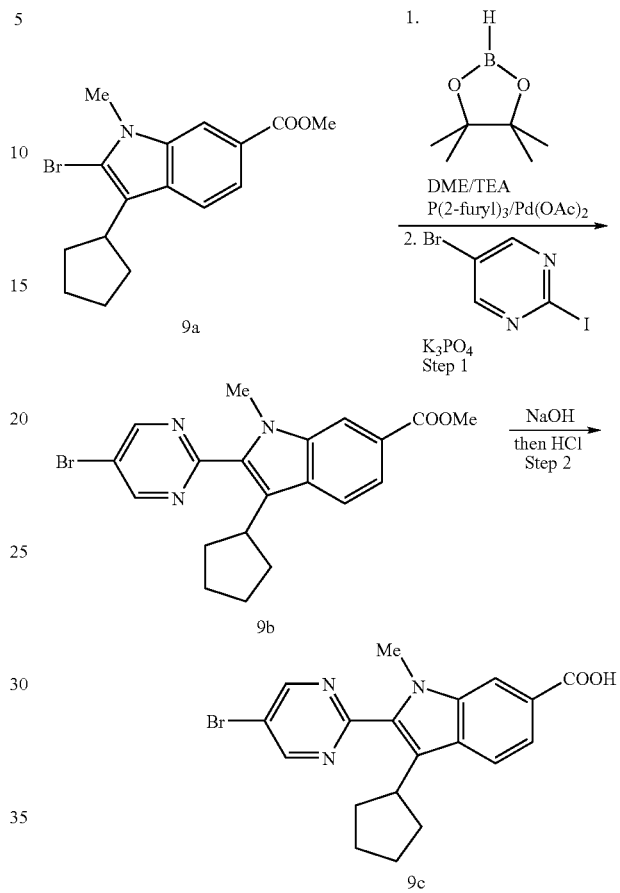

Step 1:

The bromoindole 9a (prepared as described in Example 12 of WO 03/010141) (3.0 g, 8.9 mmol, 1 equiv.) was dissolved in anhydrous DME (20 mL) and to this solution was added tri-(2-furyl)phosphine (260 mg, 1.1 mmol, 0.12 equiv.), triethylamine (3.0 mL, 21.5 mmol, 2.4 equiv.) and Pd(OAc)$_2$ (65 mg, 0.28 mmol, 0.03 equiv.). The mixture was purged by bubbling Ar through it for 10 min and pinacolborane (4,4,5,5-tetramethyl-1,3,2-dioxaborolane; 3.0 mL, 20 mmol, 2.2 equiv.) was added by syringe. The resulting dark brown mixture was stirred at 68° C. for 16 h under an argon atmosphere. The reaction mixture was then cooled to RT and the 5-bromo-2-iodopyrimidine (3.0 g, 10.5 mmol, 1.18 equiv.) was added as a solid, followed by careful, slow addition of a cooled suspension of K$_3$PO$_4$ (10.5 g, 47.1 mmol, 5.4 equiv.) in water (7 mL). Alternatively, the addition of K$_3$PO$_4$ may precede the addition of 5-bromo-2-iodopyrimidine. The dark brown reaction mixture was then heated at 80° C. under argon for 24 h. The reaction mixture was cooled to RT and poured into 10% aqueous NaCl (100 mL). The brown suspension was extracted with EtOAc (150 mL). The extract was washed with water (2×50 mL) and brine (100 mL), dried and concentrated to a volume of 50 mL. Cooling 2 h in the refrigerator gave a beige precipitate that was collected by filtration, washed with a small amount of EtOAc and dried. The filtrate was concentrated under vacuum and the residue was slurried in acetone (20 mL), heated to boiling and cooled in the fridge overnight. The solid was collected by filtration and the combined solids were further purified by chromatography using $CHCl_3$ as solvent to give the desired indole ester 9b as a beige solid in 77% yield.

Step 2:

The ester 9b (300 mg, 0.72 mmol) was suspended in DMSO (10 mL) and the suspension warmed gently to dissolve the solid. The slightly cloudy yellow solution was cooled and stirred while 2.5 N NaOH (2.0 mL, 5.0 mmol, 8.6 equiv.) was added and stirring was continued for 4 h at RT. The mixture was slowly poured into 0.5 N HCl (200 mL). The yellow precipitate was collected by filtration, washed with water and dried to give compound 9c (273 mg, 94% yield, 100% homogeneity).

Example 10

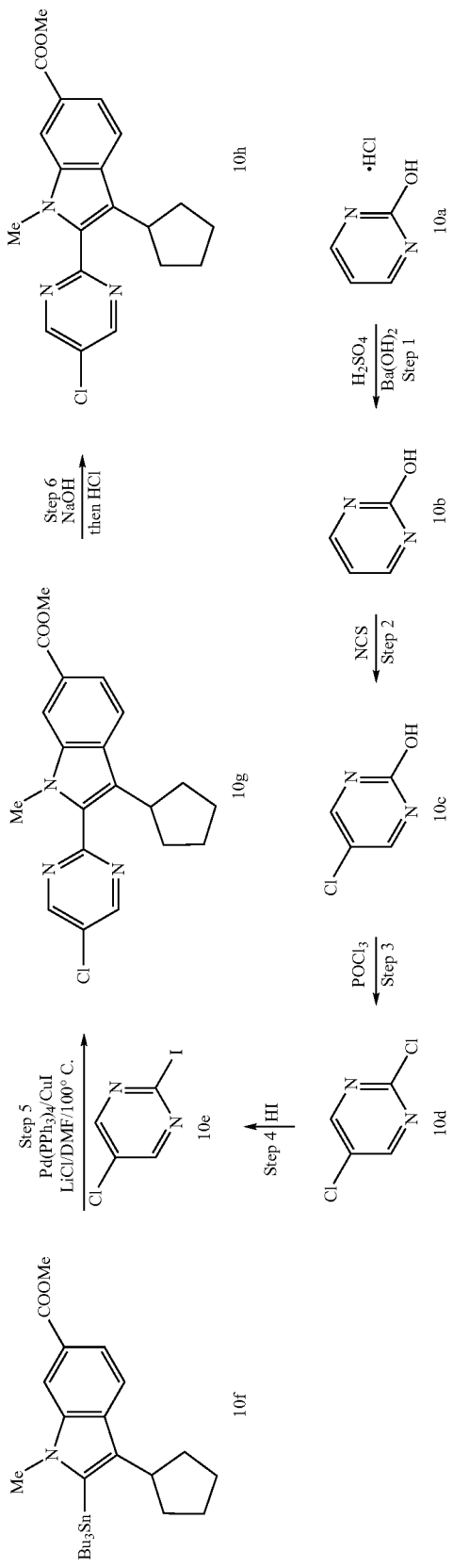

Step 1:

2-Hydroxypyrimidine hydrochloride 10a (100 g, 0.754 mole) was dissolved in water (180 mL) and conc. $H_2SO_4$ (42 mL, 0.788 mole) was added dropwise with vigorous stirring. After stirring for an additional 30 min, water was removed under reduced pressure at 70° C. and the orange residue dried under high vacuum to leave a residue (146 g). The residue was transferred into a 4 L flask and water (500 mL) was added. A suspension of $Ba(OH)_2$ (129 g, 0.752 mole) in water (1200 mL) was added and the cloudy suspension stirred for 30 min. The mixture was filtered through Celite™ and the water removed under reduced pressure to provide 10b as a bright yellow solid (66.4 g)

Step 2:

2-Hydroxypyrimidine 10b from step 1 (42 g, 0.44 mole) was added to AcOH (500 mL) and the mixture heated to 120° C. N-Chlorosuccinimide (67 g, 0.5 mole, 1.15 equivalent) was added cautiously (15 min) in small amounts to the hot solution. Stirring was continued for an additional 5 min and the reaction mixture cooled to RT. The material was concentrated under reduced pressure and the residue was stirred overnight with $CH_2Cl_2$ (200 mL). The suspended solid was removed by filtration and the filtrate evaporated under reduced pressure to give 10c as a beige solid (17.3 g)

Step 3:

The 5-chloro-2-hydroxypyrimidine 10c from step 2 (8.0 g, 0.06 mole) was placed in a dry 500 mL flask under an Ar atmosphere, and $POCl_3$ (79.4 mL) was added followed by N,N-dimethylaniline (2.6 g). The mixture was heated to 120° C. and stirred for 1 h. The dark brown mixture was concentrated under reduced pressure at 50° C. The residue was quenched carefully with ice water and the precipitated material was extracted with pentane (3×200 mL). The extract was washed with water and aqueous $NaHCO_3$ solution, and dried ($Na_2SO_4$). Volatiles were removed under reduced pressure with no external heating to prevent sublimation of the volatile dichloropyrimidine, to provide the desired product 10d as a white solid (6 g).

Step 4:

A flask was charged with 57% HI (48 mL) and cooled to 0° C. in an ice-salt mixture. The dichloropyrimidine 10d from step 3 (6 g) was added and the mixture stirred for 4 h. The yellow suspension was treated carefully with $K_2CO_3$ (32 g) in water (60 mL) and the pale yellow solid was collected by filtration. The solid was washed with water and dried to give compound 10e (8 g).

Step 5:

The 2-iodo-5-chloropyrimidine 10e from step 4 was cross-coupled to the stannylindole derivative 10f (prepared using a procedure similar to that described in example 5 of WO 03/010140 starting from the 2-bromoindole analog of example 12 of WO 03/010140) using the conditions of the Stille reaction as described in example 6 of WO 03/010140, to give compound 10g.

Step 6:

The intermediate indole ester 10g from step 5 was saponified with NaOH using a similar procedure to that described in step 2 in example 9 to give compound 10h.

Example 11

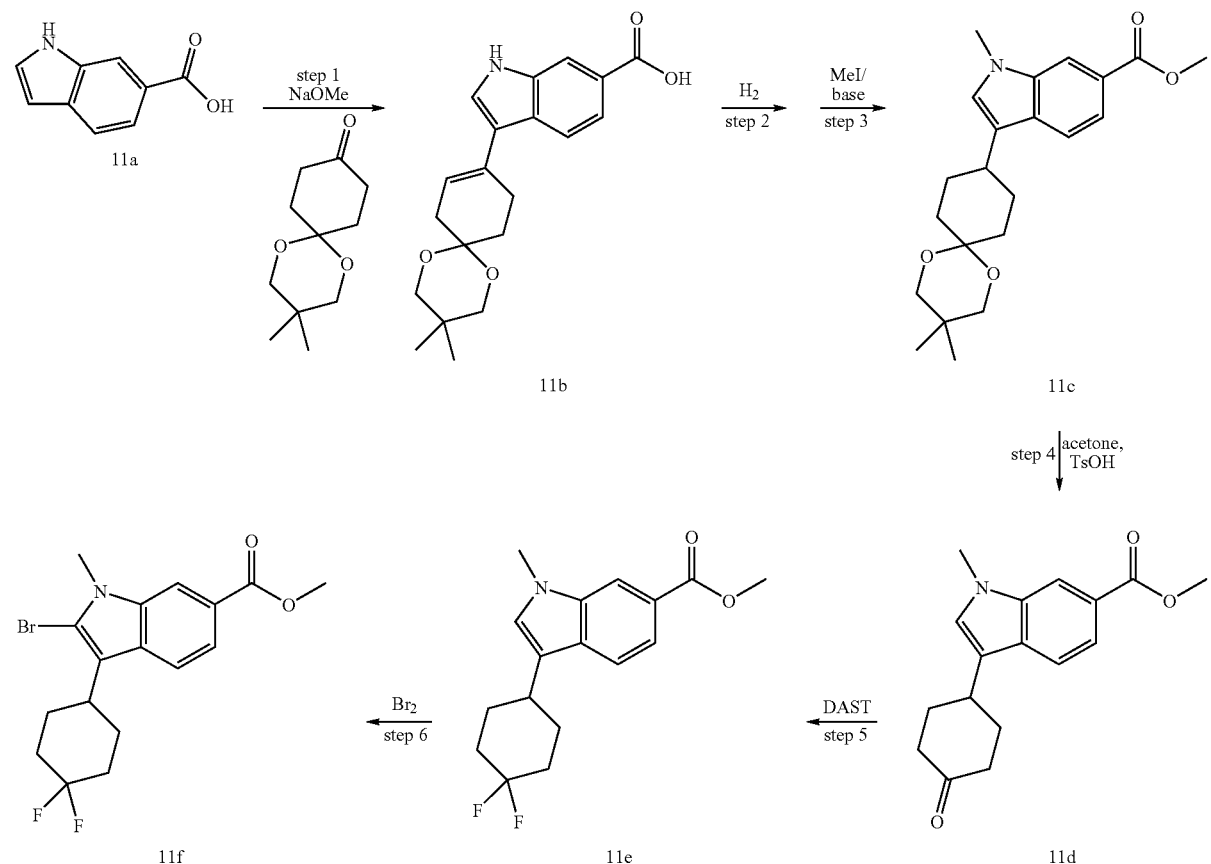

Step 1:

Indole 6-carboxylic acid 11a (10.0 g, 62 mmol) was dissolved in dry MeOH (200 mL) and 1,4-cyclohexanedione-mono-2,2-dimethyltrimethylene ketal (16.4 g, 81 mmol, 1.3 equivalent) was added. NaOMe (0.25 M in MeOH, 110 mL) was added and the mixture was refluxed for 48 h. The reaction mixture was then diluted with water (200 mL) and the MeOH removed under reduced pressure. Additional water (200 mL) was added to the residue and the mixture was stirred at 45° C. for 30 min to dissolve most solids. The solution was filtered to remove some insoluble material and the filtrate was acidified with formic acid to neutral pH (~10 mL). The precipitated solid was collected by filtration, washed with water (500 mL) and hexane (200 mL) and dried in vacuum to give the desired alkylated indole 11b as an off-white solid (23 g).

Steps 2 and 3:

The indole 11b from Step 1 (35.5 g) was suspended in a mixture of THF (300 mL) and MeOH (300 mL) and hydrogenated over 20% Pd(OH)$_2$/C (0.76 g) at 55 psi for 5 h. Additional catalyst was added (0.56 g) and hydrogenation resumed overnight. A third portion of catalyst (0.36 g) had to be added to complete the reaction (3-4 h). The catalyst was then removed by filtration and rinsed with 1:1 MeOH-THF (1.3 L), and the filtrate was evaporated under reduced pressure.

The residue from step 2 (34.3 g, 0.1 mol) was dissolved in dry NMP (300 mL) and K$_2$CO$_3$ (30.4 g, 0.22 mole, 2.2 equivalents) was added. Dimethyl carbonate (42 mL, 0.5 mol, 5 equivalents) was added and the mixture heated to 140° C. overnight. The black mixture was cooled to room temperature and then in an ice bath, and the reaction was quenched by dropwise addition of water (250 mL), maintaining an internal temperature<10° C. H$_3$PO$_4$ was then added dropwise in the cold to acidify the mixture to pH 4 (~40 mL). After stirring for an additional 1 h in the cold, the brown solid was collected by filtration, washed with water (~500 mL) and then hexane (3×30 mL). The material was purified by flash chromatography on silica gel using 5% to 40% EtOAc in hexane as eluent. The desired product 11c was obtained as a white solid (23 g).

Step 4:

The ketal 11c from Step 3 (17 g, 46 mmol) was dissolved in acetone (1.5 L) and para-toluenesulfonic acid (0.87 g) was added. The yellow solution was stirred overnight at room temperature and then refluxed for 10 h to complete the hydrolysis. Volatiles were removed under reduced pressure and the residue purified by flash chromatography on silica gel using 0% to 30% EtOAc in hexane. The desired ketone 11d was obtained as a white solid (11.5 g).

Step 5:

The ketone 11d from Step 4 (5.75 g, 20.2 mmol) was dissolved in dry DCM (115 mL) in a 200 mL pressure tube. The system was purged with argon and DAST (9.05 mL, 68.5 mmol, 3.4 equivalents) was added. The tube was sealed and heated to 50° C. for 50 h. After cooling in an ice bath, the reaction was quenched by dropwise addition of NaHCO$_3$ solution (~1 L) and the product was extracted with EtOAc (1 L). The extract was washed with water (500 mL) and brine (300 mL) and dried (Na$_2$SO$_4$). Removal of solvent gave a residue that was purified by flash chromatography on silica gel using 0% to 40% EtOAc in hexane. The product 11e was obtained as a white solid after trituration with hexane (12.2 g for two runs).

Step 6:

The indole 11e from Step 5 (10.00 g, 33 mmol) was dissolved in a mixture of THF (100 mL) and CHCl$_3$ (100 mL). The mixture was cooled in an ice-salt bath to 0° C. and pyridinium tribromide (14.26 g, 45 mmol, 1.37 equivalent) was added. After stirring for 3 h in the cold, the reaction mixture was quenched by addition of water (50 mL) and solvents removed under reduced pressure. The residue was partitioned between EtOAc (200 mL) and aqueous NaHCO$_3$ (200 mL). The organic phase was washed with water (2×100 mL) and brine (100 mL) and the aqueous phase back-extracted with another portion of EtOAc (3×50 mL). The combined extracts were dried (Na$_2$SO$_4$) and concentrated to give a yellow solid that was purified by flash chromatography on silica gel using 0% to 10% EtOAc in hexane. A second column using 1-3% EtOAc in hexane followed by DCM was required to further purify the product. The material (11 g) was then triturated twice with 10% ether in hexane (600 mL). The desired bromoindole 11f (7.9 g) was obtained as a white solid.

2-Bromo-3-(4,4-difluorocyclohexyl)-1-methyl-1H-indole-6-carboxylic acid methyl ester 11f may be converted to carboxylic acid intermediates of formula II, wherein $R^1$ is methyl, $R^2$ is defined as hereinbefore and $R^3$ is 3,3-difluorocyclohexyl, using procedures described in WO 03/010141. These intermediates may be converted to compounds of general formula I using procedures illustrated in Scheme 1 above and described in the Examples herein.

Example 12

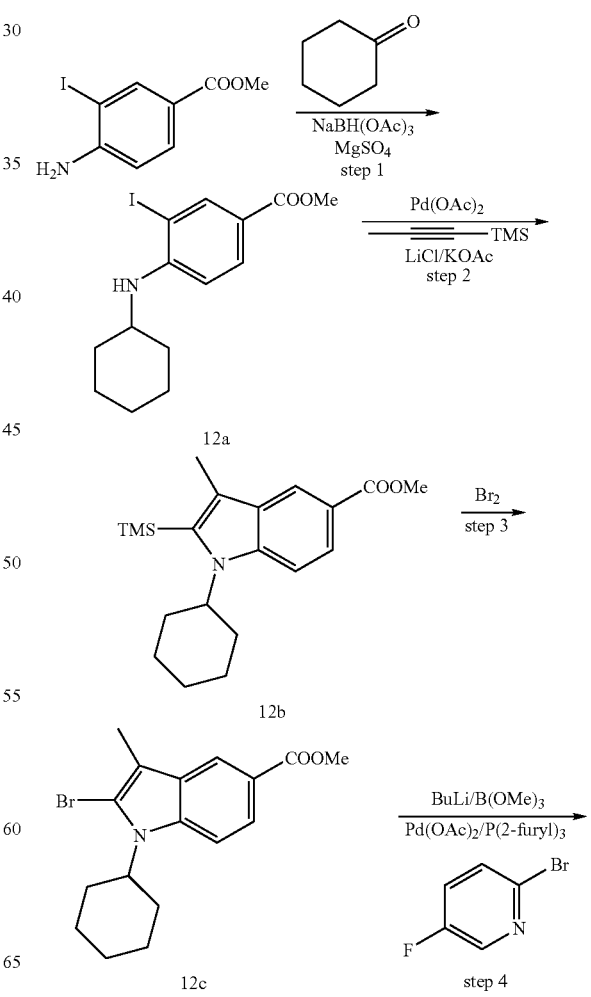

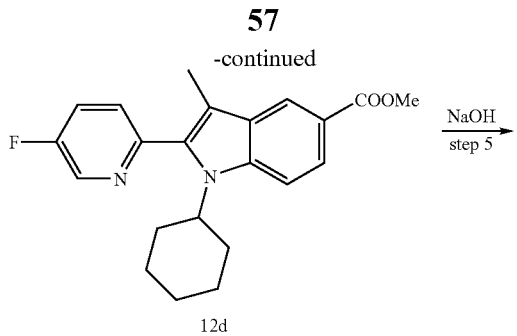

12d

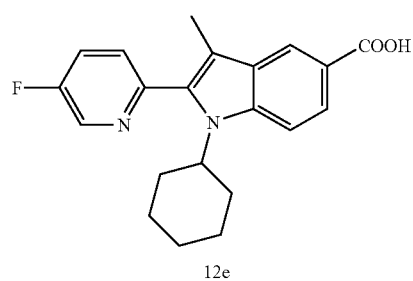

12e

Step 1:

Methyl 4-amino-3-iodobenzoate (43.75 g, 157.9 mmol) was dissolved in AcOH (900 mL) and anhydrous MgSO$_4$ (190 g) was added. Cyclohexanone (93 g, 0.95 mol, 6 equivalents) was added dropwise over 45 min to the stirred suspension. The resulting mixture was then stirred for an additional 2.5 h at RT. Sodium triacetoxyborohydride (117 g, 0.55 mol, 3.5 equivalents) was added in 8 portions over 20 min and the reaction mixture was stirred overnight at RT. Solids were then removed by filtration and washed with EtOAc, and saturated aqueous NaHCO$_3$ (1.1 L) was added dropwise to the filtrate, until the pH of the aqueous phase was 5. EtOAc (800 mL) was added and the product extracted. The aqueous phase was extracted again with EtOAc (2×300 mL) and the combined extracts were washed with saturated NaHCO$_3$ and brine, and dried (Na$_2$SO$_4$). The solvent was removed under reduced pressure and the residue purified by flash chromatography using 3% EtOAc in hexane as eluent. The desired product 12a was obtained as a yellow oil (60.95 g).

Step 2:

A dry 3-neck flask was equipped with a reflux condenser and purged with Ar. The iodoarene 12a from step 1 (51.8 g, 0.144 mole) was added to the flask followed by anhydrous DMF (1 L), LiCl (7.19 g, 0.17 mole), KOAc (33.31 g, 0.34 mole) and 1-trimethylsilyl-1-propyne (57.15 g, 0.51 mole). The red suspension was degassed by passing Ar gas through the mixture for 30 min and Pd(OAc)$_2$ (1.91 g, 8.5 mmol) was added. The mixture was heated to 100° C. and stirred at that temperature overnight, at which point a clear dark red solution was obtained. The reaction mixture was cooled to RT and saturated NH$_4$Cl (1 L) was added. The mixture was then extracted with EtOAc (1 L+2×500 mL) and the combined organic extracts washed with brine (4×600 mL). After drying (Na$_2$SO$_4$), volatiles were removed under reduced pressure and the residue was purified by flash chromatography using hexane and then 9:1 to 9:3 hexane-EtOAc as eluents. The fractions containing the product (40 g) were crystallized from hot hexane (10+3 mL) to give the desired 2-(trimethylsilyl) indole 12b as a white solid (37.6 g, 69% yield).

Step 3:

The 2-silylindole 12b from step 2 (26.50 g, 77 mmol) was dissolved in CH$_2$Cl$_2$ (600 mL) and the solution cooled in an ice-water bath. A solution of bromine (11.10 g, 69 mmol, 0.9 equivalent) in CH$_2$Cl$_2$ (70 mL) was added dropwise over 1.5 h, keeping the internal temperature close to 0° C. After completion, the light amber solution was stirred for an additional 30 min in the cold. Volatiles were then removed under reduced pressure and the solid purple residue was triturated with CH$_2$Cl$_2$ (5 mL) and hexane (20 mL). The light pink solid was collected by filtration and dried to give compound 12c (23.22 g, 86% yield).

Step 4:

The 2-bromoindole 12c from step 3 (4.99 g, 14.23 mmol) was placed in a dry 250 mL flask equipped with a reflux condenser and the system was purged with argon gas. Anhydrous THF (25 mL) was added and the yellow solution cooled to −78° C. in a dry-ice acetone bath. n-BuLi (2.5 M in hexane, 6.0 mL, 14.94 mmol, 1.05 equivalent) was added dropwise over 30 min and the dark yellow solution was stirred at −78° C. for an additional 1 h. Trimethylborate (1.77 g, 17.1 mmol, 1.2 equivalent) was added dropwise over 10 min and the mixture stirred for 1 h at −78° C. The dry ice bath was then replaced with an ice-water bath and stirring continued at 0° C. for 1 h and then at RT for 45 min. Additional anhydrous THF (25 mL) was added followed by P(para-tolyl)$_3$ (0.26 g, 0.85 mmol, 0.06 equivalent) and 2-bromo-5-fluoropyridine (2.52 g, 14.3 mmol, 1.0 equivalent). The red solution was degassed by bubbling argon gas through the mixture for 45 min. Anhydrous K$_2$CO$_3$ (3.93 g, 28.5 mmol, 2.0 equivalents), Pd(OAc)$_2$ (32 mg, 0.14 mmol, 0.01 equivalent) and MeOH (16.5 mL) were added and the mixture was refluxed overnight under Ar. The reaction mixture was then cooled to RT and quenched by addition of ether (80 mL) and water (20 mL). The aqueous phase was separated and extracted a second time with ether (80 mL). The combined extracts were washed with water and brine and dried (Na$_2$SO$_4$). Solvents were removed under reduced pressure and the residue was purified by flash chromatography using 5% EtOAc in hexane as eluent. The desired indole derivative 12d was obtained as a white solid (3.84 g, 73% yield).

Step 5:

The methyl ester 12d from step 4 (3.84 g, 10.5 mmol) was dissolved in DMSO (30 mL) and 1 N NaOH (12.6 mL, 1.2 equivalent) was added dropwise over 15 min. The mixture was stirred for 1 h at which point additional DMSO (20 mL) was added to the thick suspension. After stirring for 5 h, the reaction was judged complete by TLC. Water (30 mL) was added and the resulting clear solution was washed with ether (30 mL) and hexane (2×30 mL). The aqueous phase was then acidified with AcOH to pH=4 and the precipitated solid collected by filtration. The material was washed with water and dried to constant weight under vacuum to give compound 12e (3.51 g, 95% yield).

Compound 12e may be converted to compounds of general formula I using procedures illustrated in Scheme 1 above and described in the Examples herein.

Example 13

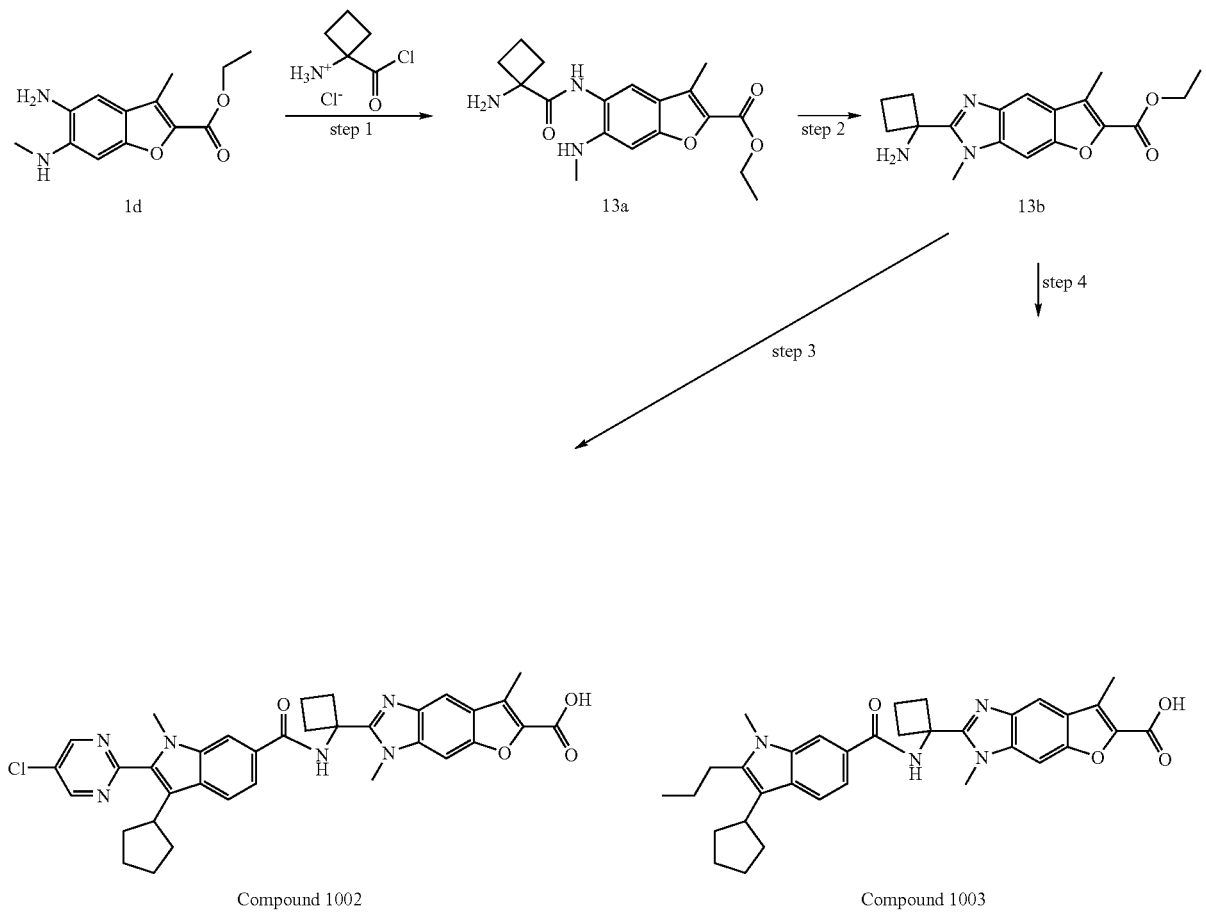

Step 1:
To a solution of compound 1d (Example 1) (0.050 g, 0.213 mmol) in CH$_2$Cl$_2$ (4.0 mL), was added pyridine (0.04 mL, 0.495 mmol), followed by the acid chloride of the cyclobutyl amino acid (prepared from 1-aminocyclobutanecarboxylic acid following an adaptation of the procedure described by E. S. Uffelman et al. (*Org. Lett.* 1999, 1, 1157)) (0.0436 g, 0.256 mmol). The reaction mixture was stirred at RT for 3 h, then diluted with EtOAc (25 mL) and washed with saturated NaHCO$_3$ (aq) and brine, dried over MgSO$_4$, filtered and concentrated. The crude compound 13a (0.052 g, ~74% yield) was used in the next step without purification.

Step 2:
A solution of 13a (0.0520 g, 0.151 mmol) in AcOH (2.00 mL) was stirred at RT for 1 h. The reaction was then cooled to 0° C. and diluted with EtOAc (10 mL) and a small amount of water (0.1 mL). Solid K$_2$CO$_3$ was slowly added to the mixture until the mixture was basic. The mixture was extracted with EtOAc (3×) and the organic layers were combined, washed with brine, dried over MgSO$_4$, filtered and concentrated. The crude material was purified by flash column chromatography using CH$_2$Cl$_2$/MeOH (20:1) as the eluent to obtain the desired product 13b (0.030 g, 61% yield).

Step 3:
To a solution of compound 13b (0.020 g, 0.061 mmol) and compound 10h (Example 10) (0.022 g, 0.061 mmol) in DMSO (1.0 mL) was added HATU (0.037 g, 0.098 mmol) and Et$_3$N (0.025 g, 0.18 mmol). The mixture was stirred at RT for 16 h, then DMSO (0.50 mL) and NaOH (5N, 0.10 mL, 0.50 mmol) were added and the solution was stirred for 1 h at 50° C. The solution was then cooled to RT, acidified with TFA and purified by preparative HPLC(ODS-AQ reverse phase column, Water/CH$_3$CN) to give 6.65 mg (17% yield) of Compound 1002, Table 1 as an off-white solid.

ES-MS m/z: ES+: 637.3 (M+H); $^1$H NMR (DMSO-d$_6$) δ: 1.57-1.72 (br, 2.3H), 1.84-1.94 (br, 6H), 1.95-2.03 (br, 1H), 2.11-2.20 (br, 1H), 2.64 (s, 3H), 2.67-2.68 (br, 1H), 2.73-2.85 (br, 2H), 3.02-3.12 (br, 2H), 3.65-3.74 (br, 3H), 3.87 (s, 4H), 3.88 (s, 3H), 7.60 (d, 1H, 8.41 Hz), 7.76 (d, 1H, 8.61 Hz), 7.89-8.00 (br, 1H), 8.06 (s, 1H), 8.13 (s, 1H), 9.14 (s, 2H).

Step 4:
Coupling of compound 13b (0.020 g, 0.061 mmol) to compound 8c (Example 8) (0.017 g, 0.061 mmol), following the same procedure as in step 3 above, gave after HPLC purification 27 mg (79% yield) of Compound 1003, Table 1 as a pale beige amorphous solid.

ES-MS m/z: ES+: 567.3 (M+H), ES−: 565.3 (M−H); $^1$H NMR (DMSO-d$_6$) δ: 0.94 (t, 3H, 7.43 Hz), 1.21-1.25 (br, 1H), 1.54 (sx, 2H, 7.24 Hz), 1.66-1.76 (br, 2H), 1.81-1.93 (br, 5H), 1.95-2.04 (br, 1H), 2.12-2.24 (br, 1H), 2.65 (s, 3H), 2.73-2.84 (br, 4H), 3.03-3.13 (br, 2H), 3.15-3.23 (br, 1H), 3.70 (s, 3H), 3.90 (s, 3H), 7.48-7.56 (br, 2H), 7.97 (s, 1H), 8.10 (s, 1H), 9.38-9.47 (br, 1H), 13.40-13.65 (br, 1H).

Example 14

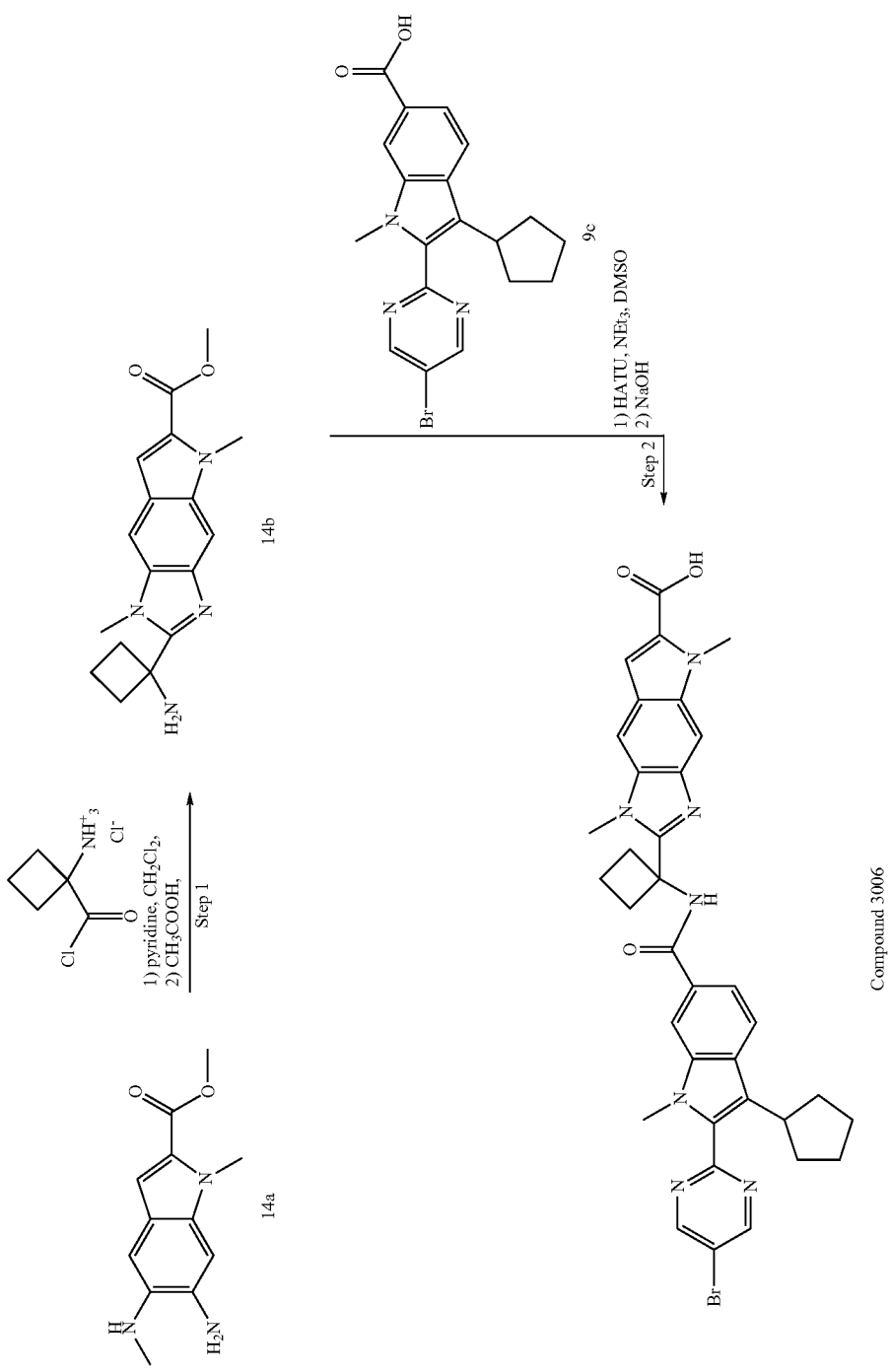

Step 1:

To a solution of compound 14a (prepared using the method of Example 3 but using sarcosine methyl ester in step 5 instead of sarcosine ethyl ester) (120 mg, 0.51 mmol, 1.0 eq.) in $CH_2Cl_2$ (9.0 mL) was added pyridine (83.2 uL, 1.03 mmol, 2.0 eq.), followed by portion-wise addition of the acid chloride (prepared from 1-aminocyclobutanecarboxylic acid following an adaptation of the procedure described by E. S. Uffelman et al. (*Org. Lett.* 1999, 1, 1157)) (140 mg, 0.82 mmol, 1.6 eq.). The reaction mixture was allowed to stir at RT for 2 h, then was immediately diluted with EtOAc (20 mL). The organic phase was washed with sat. aq. $NaHCO_3$ (20 mL) and brine (20 mL) then dried over $MgSO_4$, filtered and concentrated to give a brown residue (120 mg) The residue was dissolved in AcOH (3.00 mL) and the mixture was stirred at 80° C. for 1 h. Solid $K_2CO_3$ was slowly added to the mixture, until the solution became basic (pH>8). The mixture was extracted with EtOAc (3×15 mL) and washed with saturated aqueous $NaHCO_3$. The organic layers were combined, washed with brine (20 mL), dried over $MgSO_4$, filtered and concentrated. The crude material was purified by flash column chromatography using an elution gradient (from 100% EtOAc to 10% MeOH in EtOAc) to obtain the tricyclic fragment 14b (57 mg, 0.18 mmol, 50% yield).

Step 2:

To a solution of compound 14b (29 mg, 0.093 mmol, 1 eq.) and compound 9c (Example 9) (0.022 g, 0.061 mmol, 1.0 eq.) in DMSO (1.5 mL) was added HATU (53 mg, 0.14 mmol, 1.5 eq.) and $Et_3N$ (45 uL, 0.35 mmol, 3.5 eq.). The mixture was stirred at RT for 18 h, NaOH (2.5N, 0.19 mL, 0.47 mmol, 5 eq.) was added and the solution was heated gently to 40° C. for 2 h. The solution was then cooled to RT, acidified with TFA and purified by preparative HPLC(ODS-AQ reverse phase column, $H_2O/CH_3CN$) to give 13.7 mg (19% yield) of Compound 3006, Table 3, as an off-white powder.

ES-MS m/z: ES+: 680.3, 682.3 (M+H); $^1$H NMR (DMSO-$d_6$) δ: 1.64 (br m, 2H), 1.84-1.94 (br m, 6H), 1.99-2.1 (br, 1H), 2.20-2.30 (br m, 1H), 2.81-2.89 (br m, 1H), 3.10-3.17 (br m, 2H), 3.69 (quint, 2H, 9 Hz), 3.86 (s, 3H), 3.96 (s, 3H), 4.16 (s, 3H), 7.43 (s, 1H), 7.60 (d, 1H, 8.4 Hz), 7.77 (d, 1H, 8.6 Hz), 7.87 (s, 1H), 8.13 (s, 21-1), 9.19 (s, 2H), 9.72 (s, 1H), 13.24 (br s, 1H).

Example 15

Inhibition of NS5B RNA Dependent RNA Polymerase Activity

Representative compounds of the invention were tested for inhibitory activity against the hepatitis C virus RNA dependent polymerase (NS5B), according to the protocol described in WO 03/010141.

Example 16

Specificity of NS5B RNA Dependent RNA Polymerase Inhibition

Representative compounds of the invention were tested for inhibitory activity against polio virus RNA dependent RNA polymerase in the format that is described for the HCV polymerase, with the exception that poliovirus polymerase was used in place of the HCV NS5B polymerase, as is described in WO 03/010141.

Example 17

Cell-based Luciferase Reporter HCV RNA Replication Assay

Representative compounds of the invention were tested for activity as inhibitors of hepatitis C virus RNA replication in cells expressing a stable subgenomic HCV replicon, using the assay described in WO 2005/028501.

Tables of Compounds

The following tables list compounds representative of the invention. Representative compounds listed in Tables 1 to 5 below were tested in the NS5B RNA dependent RNA polymerase assay described in Example 15 and in the cell-based HCV RNA replication assay described in Example 17, and were found to have $IC_{50}$ and $EC_{50}$ values of less than 5 μM. Retention times ($t_R$) for each compound were measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE 1

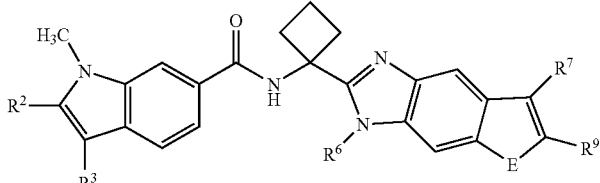

wherein $R^2$, $R^3$, $R^6$, $R^7$, E and $R^9$ are given in the table.

| Cpd. # | $R^2$ | $R^3$ | $R^6$ | $R^7$ | E | $R^9$ | $t_R$ (min) | MS $(M + H)^+$ |
|---|---|---|---|---|---|---|---|---|
| 1001 | 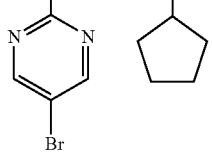 | | $CH_3$ | $CH_3$ | O | COOH | 5.6 | 681.1 |

TABLE 1-continued
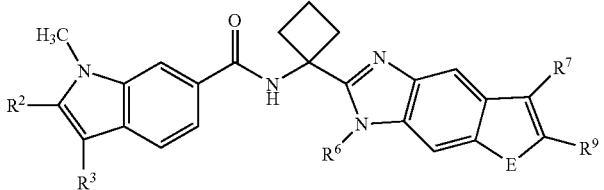
wherein R², R³, R⁶, R⁷, E and R⁹ are given in the table.
| Cpd. # | R² | R³ | R⁶ | R⁷ | E | R⁹ | $t_R$ (min) | MS (M + H)⁺ |
|---|---|---|---|---|---|---|---|---|
| 1002 | 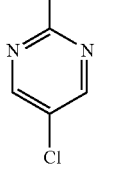 | 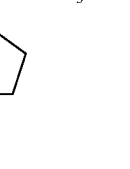 | CH₃ | CH₃ | O | COOH | 5.6 | 637.3 |
| 1003 | 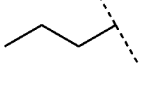 | 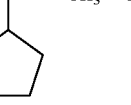 | CH₃ | CH₃ | O | COOH | 5.9 | 567.3 |
| 1004 | 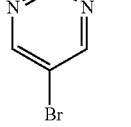 |  | CH₃ | H | S | COOH | 5.8 | 683.2 |
| 1005 | 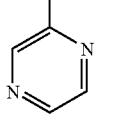 | 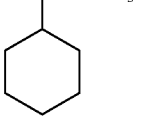 | CH₃ | H | S | COOH | 5.2 | 619.3 |
| 1006 | 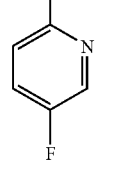 | 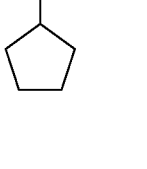 | CH₃ | H | S | COOH | 5.4 | 622.3 |
| 1007 | 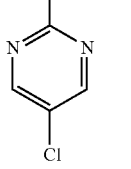 | 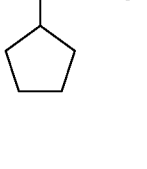 | CH₃ | H | S | COOH | 5.8 | 639.3 |
| 1008 | 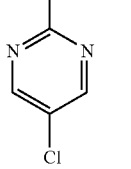 | 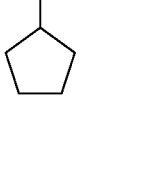 | H | H | S | COOH | 6.4 | 625.3 |

TABLE 1-continued

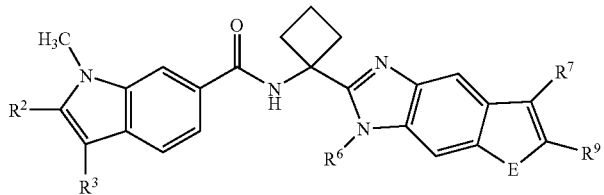

wherein R², R³, R⁶, R⁷, E and R⁹ are given in the table.

| Cpd. # | R² | R³ | R⁶ | R⁷ | E | R⁹ | $t_R$ (min) | MS $(M+H)^+$ |
|---|---|---|---|---|---|---|---|---|
| 1009 | 5-bromopyrimidin-2-yl | cyclopentyl | CH₃ | H | N—CH₃ | COOH | 6.7 | 682.2 |
| 1010 | 5-fluoropyridin-2-yl | cyclopentyl | CH₃ | H | N—CH₃ | COOH | 6.2 | 619.3 |
| 1011 | furan-3-yl | cyclopentyl | CH₃ | H | N—CH₃ | COOH | 6.5 | 590.2 |
| 1012 | propyl | cyclopentyl | CH₃ | H | N—CH₃ | COOH | 6.8 | 566.2 |
| 1013 | pyrazin-2-yl | 4,4-difluorocyclohexyl | CH₃ | H | S | COOH | 5.1 | 655.2 |
| 1014 | 5-bromopyrimidin-2-yl | 4,4-difluorocyclohexyl | CH₃ | H | S | COOH | 6.0 | 733.1 |
| 1015 | H | cyclopentyl | CH₃ | CH₃ | O | COOH | 5.9 | 525.2 |

TABLE 1-continued
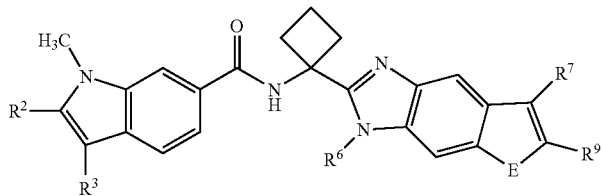
wherein R², R³, R⁶, R⁷, E and R⁹ are given in the table.
| Cpd. # | R² | R³ | R⁶ | R⁷ | E | R⁹ | $t_R$ (min) | MS $(M+H)^+$ |
|---|---|---|---|---|---|---|---|---|
| 1016 | 4-Cl-phenyl | cyclopentyl | CH₃ | CH₃ | O | COOH | 7.7 | 635.2 |
| 1017 | sec-butyl | cyclopentyl | CH₃ | CH₃ | O | CONH₂ | 6.5 | 566.2 |
| 1018 | 4-Cl-phenyl | 4,4-difluorocyclohexyl | CH₃ | H | S | COOH | | |
| 1019 | 4-Cl-phenyl | cyclopentyl | CH₃ | CH₃ | O | CONH₂ | | |
| 1020 | 4-Cl-phenyl | cyclopentyl | CH₃ | CH₃ | O | CONHCH₃ | | |

TABLE 2
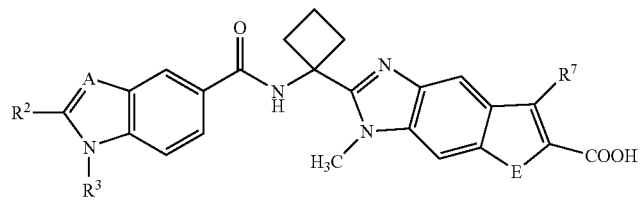
wherein A, R², R³, R⁷ and E are given in the table.
| Cpd. # | A | R² | R³ | R⁷ | E | $t_R$ (min) | MS $(M+H)^+$ |
|---|---|---|---|---|---|---|---|
| 2001 | C—CH₃ | 5-fluoropyridin-2-yl | cyclopentyl | CH₃ | O | 5.2 | 620.3 |
| 2002 | C—CH₃ | 5-fluoropyridin-2-yl | cyclohexyl | H | S | 5.7 | 636.3 |
| 2003 | C—CH₃ | 5-fluoropyridin-2-yl | cyclopentyl | H | N—CH₃ | 6.1 | 619.2 |
| 2004 | N | furan-3-yl | cyclohexyl | CH₃ | O | | |
| 2005 | N | pyridin-2-yl | cyclohexyl | CH₃ | S | | |
| 2006 | N | 3-fluoro-4-(4'-chlorobiphenyl-2-ylmethoxy)-... -(2-oxopyrrolidin-1-yl)phenyl | cyclohexyl | H | N—CH₃ | | |

TABLE 3
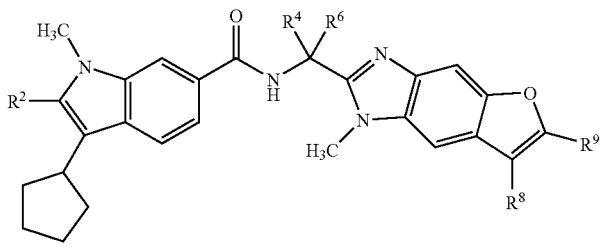
wherein R², R⁴, R⁵, D, R⁸ and R⁹ are given in the table.
| Cpd. # | R² | R⁴ R⁶ | D | R⁸ | R⁹ | $t_R$ (min) | MS $(M+H)^+$ |
|---|---|---|---|---|---|---|---|
| 3001 | propyl | cyclobutyl | O | CH₃ | COOH | 5.9 | 567.3 |
| 3002 | 5-Br-pyrimidin-2-yl | cyclobutyl | O | CH₃ | COOH | 5.8 | 681.2 |
| 3003 | 5-Cl-pyrimidin-2-yl | cyclobutyl | O | CH₃ | COOH | 5.7 | 637.3 |
| 3004 | 5-Cl-pyrimidin-2-yl | cyclobutyl | S | H | COOH | 6.6 | 639.2 |
| 3005 | 5-Br-pyrimidin-2-yl | cyclobutyl | S | H | COOH | 6.7 | 685.1 |
| 3006 | 5-Br-pyrimidin-2-yl | cyclobutyl | N—CH₃ | H | COOH | 6.7 | 680.3 |

TABLE 3-continued

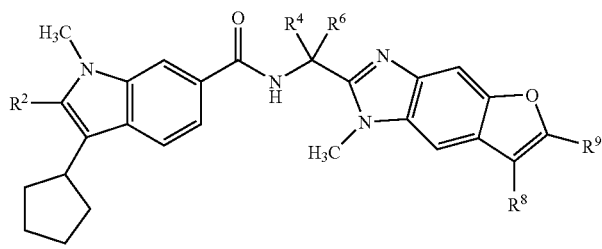

wherein $R^2$, $R^4$, $R^5$, D, $R^8$ and $R^9$ are given in the table.

| Cpd. # | $R^2$ | $\begin{array}{c}R^4\ R^6\\ \diagdown\diagup\end{array}$ | D | $R^8$ | $R^9$ | $t_R$ (min) | MS $(M + H)^+$ |
|---|---|---|---|---|---|---|---|
| 3007 | 5-fluoropyridin-2-yl | cyclobutylidene | N—CH₃ | H | COOH | 6.2 | 619.3 |
| 3008 | n-propyl | cyclobutylidene | N—CH₃ | H | COOH | 6.8 | 566.3 |
| 3009 | 4-chlorophenyl | cyclobutylidene | O | CH₃ | COOH | | |
| 3010 | 4-chlorophenyl | C(CH₃)₂ | O | CH₃ | COOH | | |
| 3011 | 4-chlorophenyl | cyclobutylidene | O | CH₃ | CONH₂ | | |
| 3012 | 4-chlorophenyl | N-methyl-azaspiro | O | CH₃ | CONH₂ | | |

TABLE 3-continued
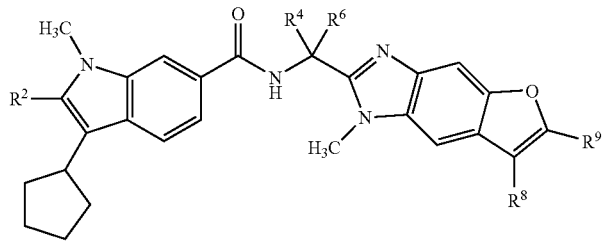
wherein $R^2$, $R^4$, $R^5$, D, $R^8$ and $R^9$ are given in the table.
| Cpd. # | $R^2$ | $R^4 \quad R^6$ | D | $R^8$ | $R^9$ | $t_R$ (min) | MS $(M + H)^+$ |
|---|---|---|---|---|---|---|---|
| 3013 | 5-Cl-pyridin-2-yl | cyclobutyl | N—CH$_3$ | H | COOH | | |
| 3014 | 5-Cl-pyridin-2-yl | C(CH$_3$)$_2$ | N—CH$_3$ | H | COOH | | |
| 3015 | 4-OMe-phenyl | cyclobutyl | N—CH$_3$ | H | COOH | | |
| 3016 | 4-Cl-phenyl | cyclobutyl | S | CH$_3$ | COOH | | |

TABLE 4
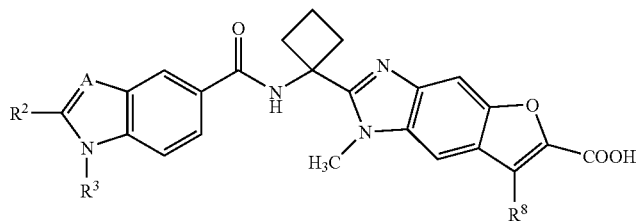
where A, R², R³, R⁸ and D are given in the table.
| Cpd. # | A | R² | R³ | D | R⁸ | $t_R$ (min) | MS (M + H)⁺ |
|---|---|---|---|---|---|---|---|
| 4001 | C—CH₃ | 5-fluoropyridin-2-yl | cyclopentyl | O | CH₃ | 5.3 | 620.3 |
| 4002 | C—CH₃ | 5-fluoropyridin-2-yl | cyclopentyl | N—CH₃ | H | 6.1 | 619.2 |
| 4003 | C—CH₃ | 5-fluoropyridin-2-yl | cyclopentyl | S | CH₃ | | |
| 4004 | N | furan-3-yl | cyclohexyl | O | CH₃ | | |
| 4005 | N | pyridin-2-yl | cyclohexyl | N—CH₃ | H | | |
| 4006 | N | 3-fluoro-4-(2-morpholino-5-(2-oxopyrrolidin-1-yl)benzyloxy)phenyl | cyclohexyl | S | H | | |

TABLE 5

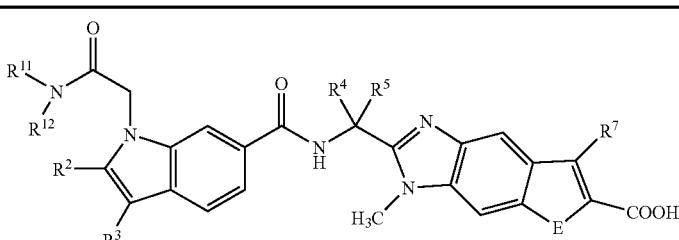

The invention claimed is:
1. A compound represented by formula (I):

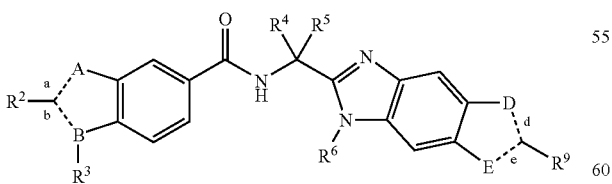

wherein:
either A is N or CR$^1$ and B is N, wherein bond a is a double bond and bond b is a single bond; or
  A is NR$^1$ and B is C, wherein bond a is a single bond and bond b is a double bond;

R$^1$ is H, (C$_{1-6}$)alkyl or a group of formula —CH$_2$C(=O)N(R$^{11}$)R$^{12}$;
  wherein R$^{11}$ is selected from H, —O—(C$_{1-6}$)alkyl, —SO$_2$—(C$_{1-6}$)alkyl, (C$_{1-6}$)alkyl, (C$_{3-7}$)cycloalkyl, (C$_{3-7}$)cycloalkyl-(C$_{1-4}$)alkyl-, (C$_{2-6}$)alkenyl, (C$_{2-6}$)alkynyl, aryl, Het, aryl-(C$_{1-4}$)alkyl- and Het-(C$_{1-4}$)alkyl-; wherein each of the (C$_{1-6}$)alkyl, (C$_{3-7}$)cycloalkyl, (C$_{3-7}$)cycloalkyl-(C$_{1-4}$)alkyl-, (C$_{2-6}$)alkenyl, (C$_{2-6}$)alkynyl, aryl, Het, aryl-(C$_{1-4}$)alkyl- and Het-(C$_{1-4}$)alkyl- is optionally substituted with R$^{15}$; and
  R$^{12}$ is selected from H, (C$_{1-6}$)alkyl, (C$_{3-7}$)cycloalkyl and (C$_{3-7}$)cycloalkyl-(C$_{1-4}$)alkyl-; wherein each of the (C$_{1-6}$)alkyl, (C$_{3-7}$)cycloalkyl and (C$_{3-7}$)cycloalkyl-(C$_{1-4}$)alkyl- is optionally substituted with one or more substituents each independently selected from —OH, halo, —COOH, —COO(C$_{1-6}$)alkyl, (C$_{1-6}$)alkyl, —O—(C$_{1-6}$)alkyl, —NH$_2$, —NH(C$_{1-6}$)alkyl and —N((C$_{1-6}$)alkyl)$_2$; or the groups $R^{11}$ and $R^{12}$ may be covalently bonded together along with the N to which they are attached to form a 4-, 5-, 6- or 7-membered saturated, unsaturated or aromatic N-containing heterocycle or a 8-, 9-, 10- or 11-membered saturated, unsaturated or aromatic N-containing bicyclic heteropolycycle, each of the heterocycle and heteropolycycle optionally containing from 1 to 3 additional heteroatoms selected from O, N, and S and each of the heterocycle and heteropolycycle being optionally substituted with $R^{15}$;

wherein $R^{15}$ is one to four substituents each independently selected from halo, oxo, $(C_{1-6})$alkyl, $(C_{1-6})$haloalkyl, —CO$(C_{1-6})$alkyl, —COOH, —COO$(C_{1-6})$alkyl, —CONH$_2$, —CONH$(C_{1-6})$alkyl, —CON$((C_{1-6})$alkyl$)_2$, —OH, —SH, —NH$_2$, —NH$(C_{1-6})$alkyl, —N$((C_{1-6})$alkyl$)_2$, —NHCO$(C_{1-6})$alkyl, —N$((C_{1-6})$alkyl)-CO$(C_{1-6})$alkyl, —NHCO—O$(C_{1-6})$alkyl, —N$((C_{1-6})$alkyl)-CO—O$(C_{1-6})$alkyl, —O—$(C_{1-6})$alkyl, —S—$(C_{1-6})$alkyl, —SO—$(C_{1-6})$alkyl, —SO$_2$—$(C_{1-6})$alkyl, nitro, cyano, azido, aryl, aryl-$(C_{1-6})$alkyl-, Het and Het-$(C_{1-6})$alkyl-;

wherein the $(C_{1-6})$alkyl is optionally substituted with —OH, —O—$(C_{1-6})$alkyl, —COOH, —COO$(C_{1-6})$alkyl, —CONH$_2$, —CONH$(C_{1-6})$alkyl, —CON$((C_{1-6})$alkyl$)_2$, —NH$_2$, —NH$(C_{1-6})$alkyl or —N$((C_{1-6})$alkyl$)_2$; and wherein the Het is optionally substituted with $(C_{1-6})$alkyl, $(C_{3-7})$cycloalkyl or $(C_{3-7})$cycloalkyl-$(C_{1-4})$alkyl-;

$R^2$ is selected from H, $(C_{1-6})$alkyl, $(C_{2-6})$alkenyl, $(C_{3-7})$cycloalkyl, aryl and Het; wherein the aryl and Het are each optionally substituted with $R^{21}$;

wherein $R^{21}$ is one, two or three substituents each independently selected from —OH, —SH, —CN, —NH$_2$, —NH$(C_{1-6})$alkyl, —N$((C_{1-6})$alkyl$)_2$, halo, $(C_{1-6})$alkyl, $(C_{1-6})$haloalkyl, $(C_{3-6})$cycloalkyl, —O—$(C_{1-6})$alkyl, —O—$(C_{1-6})$haloalkyl, —S—$(C_{1-6})$alkyl, —S—$(C_{1-6})$haloalkyl, —SO—$(C_{1-6})$alkyl-, SO—$(C_{1-6})$haloalkyl, —SO$_2$—$(C_{1-6})$alkyl, —SO$_2$—$(C_{1-6})$haloalkyl, aryl, Het, —CONH$_2$, —CONH$(C_{1-6})$alkyl and —CON$((C_{1-6})$alkyl$)_2$; wherein the —O—$(C_{1-6})$alkyl is optionally substituted with Het or aryl;

wherein each of the Het and aryl is optionally substituted with one to four substituents each independently selected from halo, aryl, Het, —N$(R^{210})R^{211}$, —N$(R^{210})$—C$(=O)$—$(C_{1-6})$alkyl and —C$(=O)$—N$(R^{210})R^{211}$;

wherein the aryl and Het are each optionally substituted with one to four substituents each independently selected from $(C_{1-6})$alkyl, halo, —N$(R^{210})_2$, —N$(R^{210})$—C$(=O)$—$(C_{1-6})$alkyl and —C$(=O)$—N$(R^{210})_2$;

$R^{210}$ is selected independently in each instance from H and $(C_{1-6})$alkyl; and $R^{211}$ is selected independently in each instance from H, $(C_{1-6})$alkyl, $(C_{3-7})$cycloalkyl and aryl; or $R^{210}$ and $R^{211}$ are linked, together with the N to which they are attached, to form a 5- or 6-membered saturated or unsaturated heterocycle, wherein said heterocycle is optionally substituted with one or two substituents each independently selected from $(C_{1-6})$alkyl and oxo;

$R^3$ is $(C_{5-6})$cycloalkyl, optionally substituted with from one to four halo substituents;

$R^4$ and $R^5$ are covalently bonded together along with the carbon atom to which they are attached to form $(C_{3-7})$cycloalkyl, $R^6$ is H or $(C_{1-6})$alkyl;

D is CR$^7$ and E is NR$^8$, wherein bond d is a double bond and bond e is a single bond; or D is NR$^7$ and E is CR$^8$, wherein bond d is a single bond and bond e is a double bond; wherein $R^7$ and $R^8$ are each independently selected from H, $(C_{1-6})$alkyl and halo; and $R^9$ is —COOH, —CONH$_2$, —CONH$(C_{1-6})$alkyl, —CON$((C_{1-6})$alkyl$)_2$, tetrazolyl, —CONHSO$_2$R$^{90}$, or —CONHSO$_2$N$(R^{91})R^{90}$, wherein R$^{90}$ is selected from $(C_{1-6})$alkyl, $(C_{3-7})$cycloalkyl, $(C_{3-7})$cycloalkyl-$(C_{1-4})$alkyl-, aryl, aryl-$(C_{1-4})$alkyl, Het, and Het-$(C_{1-4})$alkyl; and R$^{91}$ is selected from H and $(C_{1-6})$alkyl;

wherein Het is defined as a 4- to 7-membered heterocycle having 1 to 4 heteroatoms each independently selected from O, N and S, which may be saturated, unsaturated or aromatic, and which is optionally fused to at least one other cycle to form a 7 to 14-membered heteropolycycle having wherever possible 1 to 5 heteroatoms, each independently selected from O, N and S, the heteropolycycle being saturated, unsaturated or aromatic;

or a salt thereof or ester thereof.

2. A compound according to claim 1 represented by a formula selected from the following:

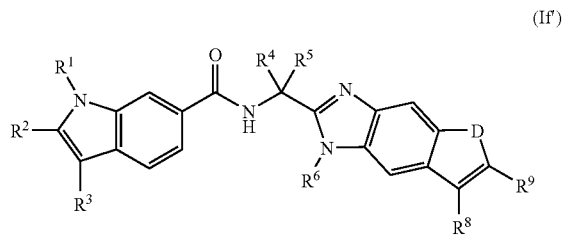

(If')

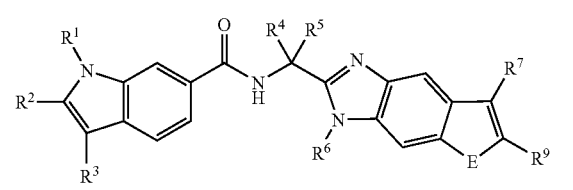

(Ig')

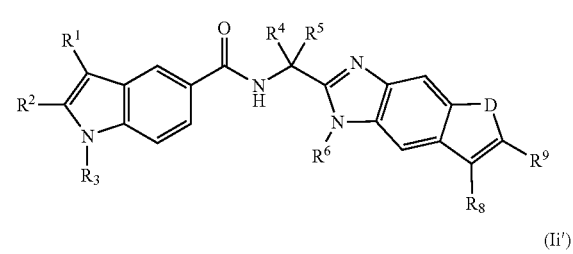

(Ih')

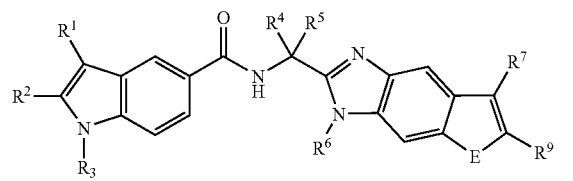

(Ii')

-continued

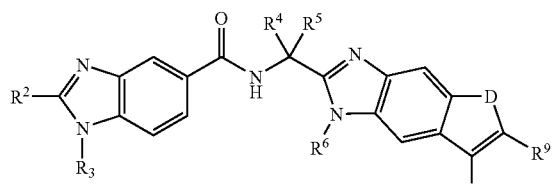
(Ij')

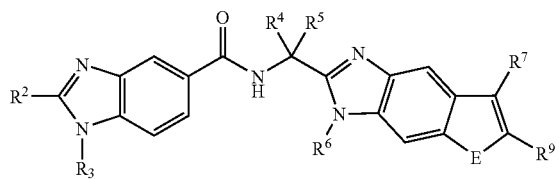
(Ik')

wherein D, E, $R^1$, $R^2$, $R^3$, $R^4$, $R^5$, $R^6$, $R^7$, $R^8$ and $R^9$ are defined as in claim 1.

3. A compound according to claim 1 wherein $R^1$ is selected from H and $(C_{1-6})$alkyl.

4. A compound according to claim 1 wherein $R^1$ is a group of formula —$CH_2C(=O)N(R^{11})R^{12}$;

wherein $R^{11}$ is selected from H, $(C_{1-6})$alkyl, $(C_{3-7})$cycloalkyl, $(C_{3-7})$cycloalkyl-$(C_{1-4})$alkyl-, aryl, Het, aryl-$(C_{1-4})$alkyl- and Het-$(C_{1-4})$alkyl-; wherein Het is a 5- or 6-membered saturated, unsaturated or aromatic heterocycle containing 1 or 2 heteroatoms each independently selected from N, O and S, or Het is a 9- or 10-membered saturated, unsaturated or aromatic bicyclic heteropolycycle containing 1 or 2 heteroatoms each independently selected from N, O and S;

each of the $(C_{1-6})$alkyl, $(C_{3-7})$cycloalkyl, $(C_{3-7})$cycloalkyl-$(C_{1-4})$alkyl-, aryl, Het, aryl-$(C_{1-4})$alkyl- and Het-$(C_{1-4})$alkyl- being optionally substituted with $R^{15}$; and $R^{12}$ is selected from H, $(C_{1-6})$alkyl, $(C_{3-7})$cycloalkyl and $(C_{3-7})$cycloalkyl-$(C_{1-4})$alkyl-;

wherein each of the $(C_{1-6})$alkyl, $(C_{3-7})$cycloalkyl and $(C_{3-7})$cycloalkyl-$(C_{1-4})$alkyl- is optionally substituted with one or more substituents each independently selected from —OH, halo, —COOH, —COO$(C_{1-6})$alkyl, $(C_{1-6})$alkyl, —O—$(C_{1-6})$alkyl, —$NH_2$, —NH$(C_{1-6})$alkyl and —N$((C_{1-6})$alkyl$)_2$; or the groups $R^{11}$ and $R^{12}$ may be covalently bonded together along with the N to which they are attached to form a 5-, 6- or 7-membered saturated, unsaturated or aromatic N-containing heterocycle or a 8-, 9-, 10- or 11-membered saturated, unsaturated or aromatic N-containing bicyclic heteropolycycle, each of the heterocycle and heteropolycycle optionally containing from 1 to 3 additional heteroatoms each independently selected from O, N, and S and each of the heterocycle and heteropolycycle being optionally substituted with $R^{15}$;

wherein $R^{15}$ is defined as in claim 1.

5. A compound according to claim 4 wherein $R^{15}$ is one to three substituents each independently selected from fluorine, chlorine, bromine, methyl, ethyl, propyl, —COOH, —COO$(C_{1-3})$alkyl, —$CONH_2$, —CONH$(C_{1-3})$alkyl, —CON$((C_{1-3})$alkyl$)_2$, —OH, —$NH_2$, —NH$(C_{1-3})$alkyl, —N$((C_{1-3})$alkyl$)_2$, —O—$(C_{1-3})$alkyl, nitro, cyano, azido, phenyl, phenylmethyl,

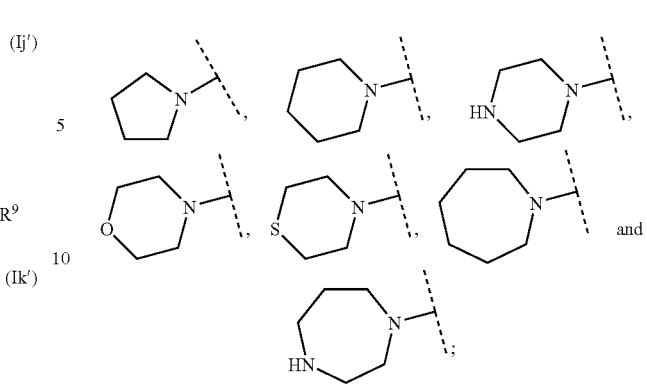

wherein each of the methyl, ethyl and propyl are optionally substituted with —OH, —O—$(C_{1-3})$alkyl, —COOH, —COO$(C_{1-3})$alkyl, —$CONH_2$, —CONH$(C_{1-3})$alkyl, —CON$((C_{1-3})$alkyl$)_2$, —$NH_2$, —NH$(C_{1-3})$alkyl or —N$((C_{1-3})$alkyl$)_2$; and wherein each of the

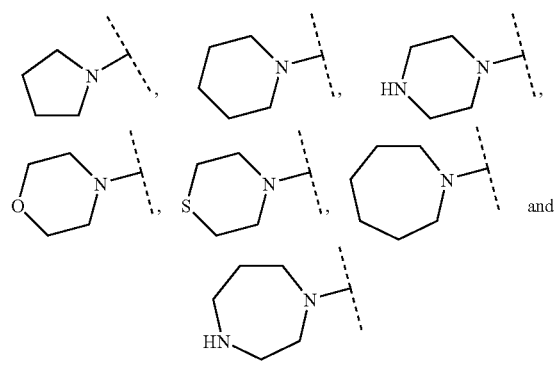

are optionally substituted with $(C_{1-3})$alkyl.

6. A compound according to claim 1 wherein $R^2$ is H, $(C_{1-6})$alkyl, $(C_{2-6})$alkenyl or $(C_{3-7})$cycloalkyl.

7. A compound according to claim 1 wherein $R^2$ is aryl or Het, wherein Het is a 5- or 6-membered aromatic heterocycle having 1 to 4 heteroatoms each independently selected from O, N and S;

wherein the aryl and Het are unsubstituted or substituted with $R^{21}$, wherein $R^{21}$ is defined as in claim 1.

8. A compound according to claim 7 wherein $R^{21}$ is one, two or three substituents each independently selected from $(C_{1-3})$alkyl, $(C_{1-3})$haloalkyl, $(C_{3-6})$cycloalkyl, —CN, —$NH_2$, —NH$(C_{1-3})$alkyl, —N$((C_{1-3})$alkyl$)_2$, halo, —O—$(C_{1-3})$alkyl, —O—$(C_{1-3})$haloalkyl, —S—$(C_{1-3})$alkyl, —S—$(C_{1-3})$haloalkyl, —SO—$(C_{1-3})$alkyl-, SO—$(C_{1-3})$haloalkyl, —$SO_2$—$(C_{1-3})$alkyl and —$SO_2$—$(C_{1-3})$haloalkyl.

9. A compound according to claim 7 wherein $R^2$ is phenyl substituted with $R^{21}$ and $R^{21}$ is —O—$(C_{1-6})$alkyl substituted with phenyl wherein the phenyl is optionally substituted with one to four substituents each independently selected from halo, phenyl, Het, —N$(R^{210})R^{211}$, —N$(R^{210})$—C$(=O)$—$(C_{1-6})$alkyl and —C$(=O)$—N$(R^{210})^{R211}$; wherein the Het is a 5- or 6-membered monocyclic saturated heterocycle; and wherein the phenyl and Het are each optionally substituted with one to four substituents each independently selected from $(C_{1-6})$alkyl, halo, —N$(R^{210})_2$, —N$(R^{210})$—C$(=O)$—$(C_{1-6})$alkyl and —C$(=O)$—N$(R^{210})_2$;

$R^{210}$ is selected independently in each instance from H and $(C_{1-6})$alkyl; and $R^{211}$ is selected independently in each instance from H, $(C_{1-6})$alkyl, $(C_{3-7})$cycloalkyl and aryl; or $R^{210}$ and $R^{211}$ are linked, together with the N to which they are attached, to form a 5- or 6-membered saturated or unsaturated heterocycle, wherein said heterocycle is optionally substituted with one or two substituents each independently selected from $(C_{1-6})$alkyl and oxo;

and $R^{21}$ is additionally optionally one or two substituents each independently selected from $(C_{1-3})$alkyl, $(C_{1-3})$haloalkyl, $(C_{3-6})$cycloalkyl, —CN, —NH$_2$, —NH$(C_{1-3})$alkyl, —N$((C_{1-3})$alkyl$)_2$, halo, —O—$(C_{1-3})$alkyl, —S—$(C_{1-3})$alkyl, —S—$(C_{1-3})$haloalkyl, —SO—$(C_{1-3})$alkyl-, SO—$(C_{1-3})$haloalkyl, —SO$_2$—$(C_{1-3})$alkyl and —SO$_2$—$(C_{1-3})$haloalkyl.

10. A compound according to claim 1 wherein $R^3$ is cyclopentyl or cyclohexyl, each being optionally substituted with one or two fluoro substituents.

11. A compound according to claim 1 wherein $R^4$ and $R^5$ are covalently bonded together along with the carbon atom to which they are attached to form $(C_{3-6})$cycloalkyl.

12. A compound according to claim 1 wherein $R^6$ is H, methyl or ethyl.

13. A compound according to claim 1 wherein $R^7$ is H or $(C_{1-6})$alkyl.

14. A compound according to claim 1 wherein $R^8$ is H or $(C_{1-6})$alkyl.

15. A compound according to claim 1 wherein D is $CR^7$ and E is $NR^8$ or D is $NR^7$ and E is $CR^8$, and at least one of $R^7$ and $R^8$ is H.

16. A compound according to claim 1 wherein $R^9$ is —COOH.

17. A compound according to claim 1, or a pharmaceutically acceptable salt or ester thereof; as a medicament.

18. A pharmaceutical composition comprising a therapeutically effective amount of a compound according to claim 1, or a pharmaceutically acceptable salt or ester thereof; and one or more pharmaceutically acceptable carriers.

19. The pharmaceutical composition according to claim 18 additionally comprising at least one other antiviral agent.

20. A method of treating a hepatitis C viral infection in a mammal having the infection, the method comprising administering to the mammal a therapeutically effective amount of a compound according to claim 1 a pharmaceutically acceptable salt or ester thereof, or a composition thereof.

21. A method of treating a hepatitis C viral infection in a mammal having the infection, the method comprising administering to the mammal a therapeutically effective amount of a combination of a compound according to claim 1 or a pharmaceutically acceptable salt or ester thereof, and at least one other antiviral agent; or a composition thereof.

22. An article of manufacture comprising a composition effective to treat a hepatitis C viral infection; and packaging material comprising a label which indicates that the composition can be used to treat infection by the hepatitis C virus; wherein the composition comprises a compound according to claim 1 or a pharmaceutically acceptable salt or ester thereof.

23. A method of inhibiting the replication of hepatitis C virus comprising exposing the virus to an effective amount of the compound according to claim 1, or a salt or ester thereof, under conditions where replication of hepatitis C virus is inhibited.

* * * * *